(12) United States Patent
Stamford et al.

(10) Patent No.: US 6,444,687 B1
(45) Date of Patent: Sep. 3, 2002

(54) SUBSTITUTED IMIDAZOLE NEUROPEPTIDE Y Y5 RECEPTOR ANTAGONISTS

(75) Inventors: Andrew W. Stamford, Chatham Township; Craig D. Boyle, Branchburg; Ying Huang, East Brunswick, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/737,141

(22) Filed: Dec. 14, 2000

Related U.S. Application Data

(60) Provisional application No. 60/171,223, filed on Dec. 16, 1999.

(51) Int. Cl.[7] .................. A61K 31/4545; A61K 31/454; C07D 401/14; C07D 401/04; A61P 3/00
(52) U.S. Cl. .................... 514/318; 514/326; 514/333; 514/341; 514/252.14; 514/253.09; 514/254.02; 514/254.05; 544/295; 544/360; 544/367; 544/370; 546/194; 546/210; 546/256; 546/274.1
(58) Field of Search ............................... 546/194, 210; 514/318, 326

(56) References Cited

U.S. PATENT DOCUMENTS

| | | | |
|---|---|---|---|
| 3,657,441 A | 4/1972 | Jensen et al. | 424/273 |
| 4,642,311 A | 2/1987 | Baldwin et al. | 514/316 |

FOREIGN PATENT DOCUMENTS

| | | | |
|---|---|---|---|
| EP | 074 130 | | 3/1983 |
| EP | 131 973 | | 1/1985 |
| EP | 257 897 | | 3/1988 |
| EP | 353 606 | | 2/1990 |
| EP | 627 499 | | 12/1994 |
| EP | 712 847 | | 5/1996 |
| WO | 98/24785 | | 6/1998 |
| WO | 99/01128 | | 1/1999 |
| WO | WO 99/31089 | * | 6/1999 |
| WO | 99/48873 | | 9/1999 |
| WO | 00/64880 | | 11/2000 |
| WO | 00/66578 | | 11/2000 |

OTHER PUBLICATIONS

Chen et al, *Tet. Lett.*, 37, 30 (1996), p. 5233–5234.
Browne, *Aust. J. Chem.*, 28 (1975), p. 2543–3213.
Tanaka et al, *Chem. Pharm. Bull.*, 40, 12 (1992), p. 3206–3213.

* cited by examiner

*Primary Examiner*—Evelyn Mei Huang
(74) *Attorney, Agent, or Firm*—Anita W. Magatti

(57) ABSTRACT

Compounds of the formula I

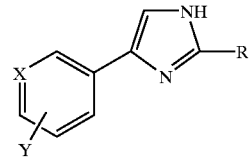

or a pharmaceutically acceptable salt, solvate or N-oxide thereof, wherein X is =CH— or =N—;

Y is H, halogen, trihaloalkyl, alkyl, alkenyl, cycloalkyl, cycloalkyl, SH, —S-alkyl, or —CN.

R is alkyl, —CF$_3$, cycloalkyl, heterocycloalkyl, heterocycloalkyl-alkyl, heteroarylalky or adamantyl, or optionally substituted phenyl, phenoxyalkyl, phenylthioalkyl, pyridyl, thienyl, thiazolyl, pyrazinyl, 1,2,5,6-tetrahydropyridine or

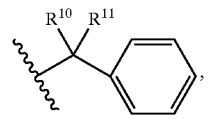

wherein R$^{10}$ and R$^{11}$ are hydrogen, alkyl or together form a cycloalkyl, are disclosed, as well as pharmaceutical compositions and methods of using said compounds in the treatment of eating disorders and diabetes.

7 Claims, No Drawings

SUBSTITUTED IMIDAZOLE NEUROPEPTIDE Y Y5 RECEPTOR ANTAGONISTS

CROSS REFERENCE TO RELATED APPLICATIONS

This application claims the benefit of U.S. Provisional Application No. 60/171,223, filed Dec. 16, 1999.

BACKGROUND OF THE INVENTION

The present invention relates to selective 4-(phenyl or pyridyl)imidazole derivative neuropeptide Y Y5 receptor antagonists useful in the treatment of eating disorders, pharmaceutical compositions containing the compounds, and methods of treatment using the compounds.

Neuropeptide Y is a 36 amino acid peptide that is widely distributed in the central and peripheral nervous systems. This peptide mediates a number of physiological effects through its various receptor subtypes. Studies in animals have shown that neuropeptide Y is a powerful stimulus of food intake, and it has been demonstrated that activation of neuropeptide Y Y5 receptors results in hyperphagia and decreased thermogenesis. Therefore compounds that antagonize neuropeptide Y at the Y5 receptor subtype represent an approach to the treatment of eating disorders such as obesity and hyperphagia, and diabetes.

Substituted imidazoles are used in various pharmaceutical and non-pharmaceutical applications. WO 99/01128 discloses substituted diarylimidazoles as NPY Y5 receptor antagonists.

SUMMARY OF THE INVENTION

The present invention relates to compounds represented by the structural formula I:

I or a pharmaceutically acceptable salt, solvate or N-oxide thereof, wherein

X is =CH— or =N—;

Y is 1 to 3 substituents independently selected from the group consisting of H, halogen, trihaloalkyl, $C_1$–$C_6$ alkyl, $C_1$–$C_6$ alkenyl, $C_3$–$C_7$-cycloalkyl, $C_1$–$C_6$ alkyl substituted by $C_3$–$C_7$-cycloalkyl, —OH, —O($C_1$–$C_6$) alkyl, —SH, —S($C_1$–$C_6$)alkyl, or —CN.

R is $R^1$-phenyl, $R^1$-pyridyl, adamantyl, —$(CH_2)_n$—O—($R^9$-phenyl), —$(CH_2)_n$—S—($R^9$-phenyl), —$CF_3$, $C_1$–$C_6$alkyl, $C_3$–$C_7$-cycloalkyl, or heterocycloalkyl selected from the group consisting of 4 to 6 membered rings comprising 3 to 5 carbon ring members and 1 to 3 ring members selected from the group consisting of —$NR^8$—, —O— and —S—, heterocycloalkyl($C_1$–$C_6$) alkyl wherein heterocycloalkyl is as defined above, heteroaryl($C_1$–$C_6$)alkyl,

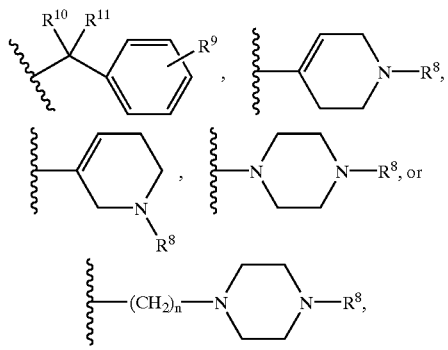

provided that when R is $R^1$-phenyl, $R^1$-pyridyl, adamantyl, —$(CH_2)_n$—O—($R^9$-phenyl), —$(CH_2)_n$—S—($R^9$-phenyl), —$CF_3$, $C_1$–$C_6$alkyl, or $C_3$–$C_7$-cycloalkyl, Y is 3-$CF_3$;

n is 0, 1, 2 or 3;

$R^1$ is 1–3 substituents independently selected from the group consisting of hydroxy($C_1$–$C_6$)alkyl; $NO_2$; —CHO, —C(O)O($C_1$–$C_6$)alkyl; —C(O)$NR^4R^5$; —$(CH_2)_pNR^4R^5$; —$(CH_2)_pNR^4R^6$; —$NR^4SO_2R^7$; —NHCOH; —$NR^4COR^5$; —NHC(O)$NR^4R^5$; aryl; and heteroaryl;

p is 0, 1, 2 or 3;

$R^4$ is hydrogen or $C_1$–$C_6$ alkyl;

$R^5$ is $C_1$–$C_6$ alkyl, aryl or heteroaryl; provided $R^4$ and $R^5$ are not both $C_1$–$C_6$ alkyl, and provided that when $R^4$ is hydrogen, $R^5$ is not $C_1$–$C_6$ alkyl; or $R^4$ and $R^5$ together are $C_3$–$C_6$ alkylene and together with the nitrogen to which they are attached form a 4–7 membered ring; or $R^4$ and $R^5$, together with the nitrogen to which they are attached, form a 5, 6 or 7-membered ring, wherein 1 or 2 ring members are independently selected from the group consisting of —O—, —S— and —$NR^{12}$—;

$R^6$ is $C_3$–$C_7$ cycloalkyl, benzyl, diphenylmethyl or

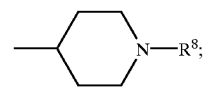

or $R^4$ and $R^6$, together with the nitrogen to which they are attached form a group of the formula

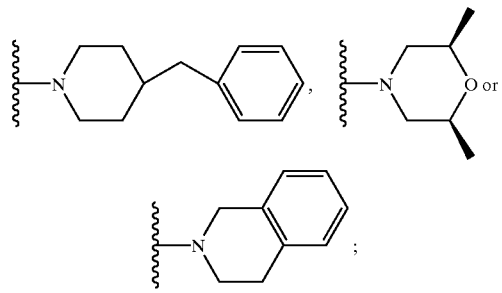

$R^7$ is $C_1$–$C_6$ alkyl, $C_3$–$C_7$ cycloalkyl, benzyl, aryl, or heteroaryl;

$R^8$ is hydrogen, $C_1$–$C_6$ alkyl, —C(O)—($C_1$–$C_6$ alkyl), —C(O)—($C_3$–$C_7$ cycloalkyl), —C(O)-aryl, —C(O)-heteroaryl, —$SO_2$—$R^7$, aryl, heteroaryl, —$CONR^4R^5$ or —C(O)—O—($C_1$–$C_6$)alkyl;

$R^9$ is 1 to 3 substituents independently selected from the group consisting of hydrogen, $C_1$–$C_6$ alkyl, $C_1$–$C_6$ alkoxy, halogeno and —$CF_3$;

$R^{10}$ and $R^{11}$ are independently selected from the group consisting of hydrogen and $C_1$–$C_6$ alkyl, or $R^{10}$ and $R^{11}$, together with the carbon to which they are attached, form a $C_3$–$C_7$ ring; and $R^{12}$ is hydrogen, $C_1$–$C_6$ alkyl, —C(O)—($C_1$–$C_6$ alkyl), —$SO_2$—$R^7$, $R^9$-phenyl, —$CONR^4R^5$, —C(O)—O—($C_1$–$C_6$)alkyl, —CHO, $C_3$–$C_7$ cycloalkyl, ($C_3$–$C_7$) cycloalkyl($C_1$–$C_6$)alkyl, benzyl, benzoyl, —C(O) ($C_3$–$C_7$)cycloalkyl, —C(O)($C_1$–$C_6$)alkylphenyl, pyridylmethyl, —C(O)pyridyl, —C(O)N(di-($C_1$–$C_6$) alkyl) or 4-tetrahydropyranyl.

One group of preferred compounds is that wherein R is as defined above; $R^1$ is 1–3 substituents selected from the group consisting of hydroxy($C_1$–$C_6$)alkyl, $NO_2$, —CHO, —C(O)O($C_1$–$C_6$)alkyl, —$(CH_2)_p NR^4R^5$, —$(CH_2)_p NR^4R^6$, —$NR^4SO_2R^7$, —NHCOH, —$NHCOR^5$, —$NR^4COR^5$—, $NHC(O)NR^4R^5$, aryl and heteroaryl; and p is 0, 1 or 2.

Another group of preferred compounds is that wherein R is adamantyl, —$(CH_2)_n$—O—($R^9$-phenyl), —$(CH_2)_n$—S—($R^9$-phenyl), —$CF_3$, $C_1$–$C_6$ alkyl, $C_3$–$C_7$-cycloalkyl, heteroaryl-($C_1$–$C_6$)alkyl, heterocycloalkyl-($C_1$–$C_6$)alkyl, or

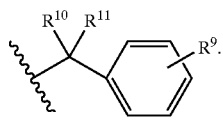

Another group of preferred compounds is that wherein R is heterocycloalkyl,

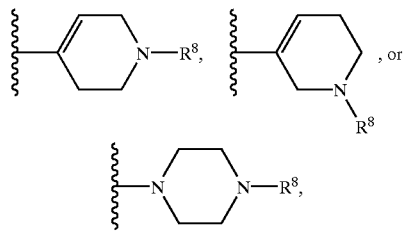

wherein heterocycloalkyl is defined as

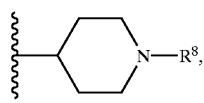

and $R^8$ is preferably C(O)—($C_1$–$C_6$ alkyl), —C(O)—($C_3$–$C_7$ cycloalkyl), —C(O)-aryl, —C(O)-heteroaryl, —$SO_2$—$R^7$, aryl, heteroaryl, and —$CONR^4R^5$.

In another group of preferred compounds of formula I, R is $R^1$-phenyl or $R^1$-pyridyl of the formula

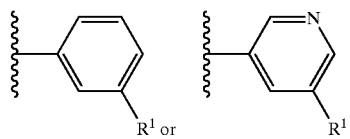

$R^1$ is preferably —$NR^4SO_2R^7$, wherein $R^4$ is H or straight or branched $C_1$–$C_6$ alkyl, and $R^7$ is straight or branched $C_1$–$C_6$ alkyl.

Preferred compounds of this invention include those of formula I wherein X is =CH—, Y is 3—$CF_3$, and R is selected from the group consisting of:

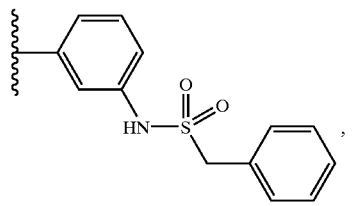

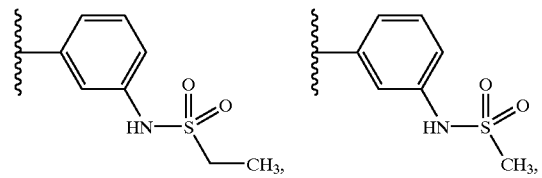

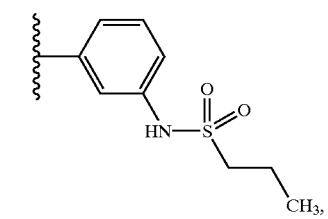

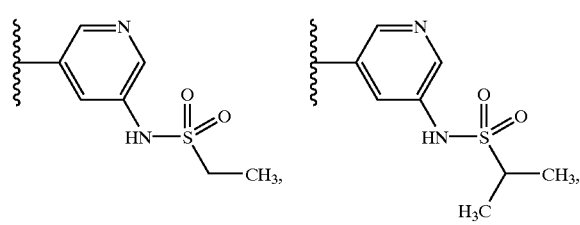

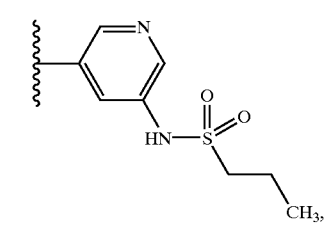

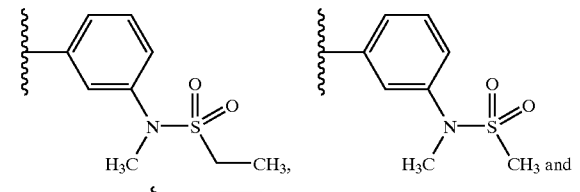

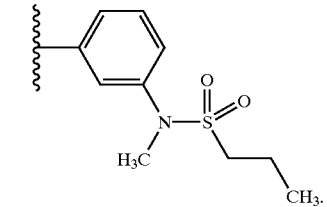

Another group of preferred compounds of this invention include those of formula 1 wherein X is =CH—, and R is selected from the group consisting of:

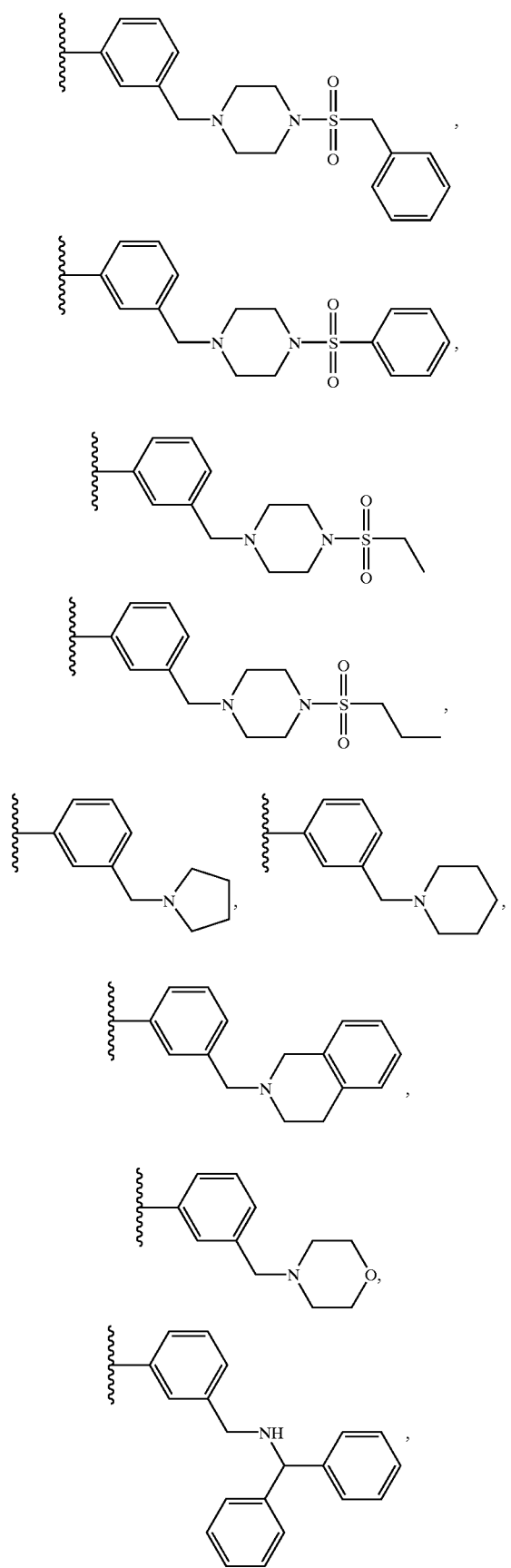
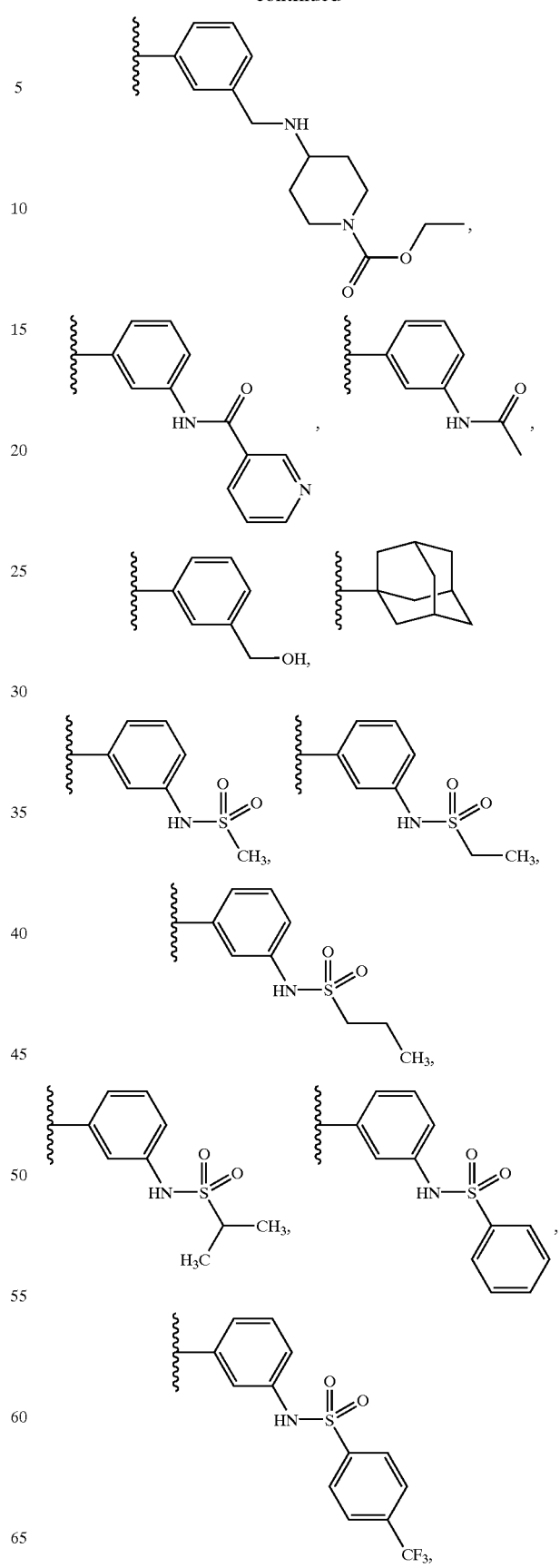

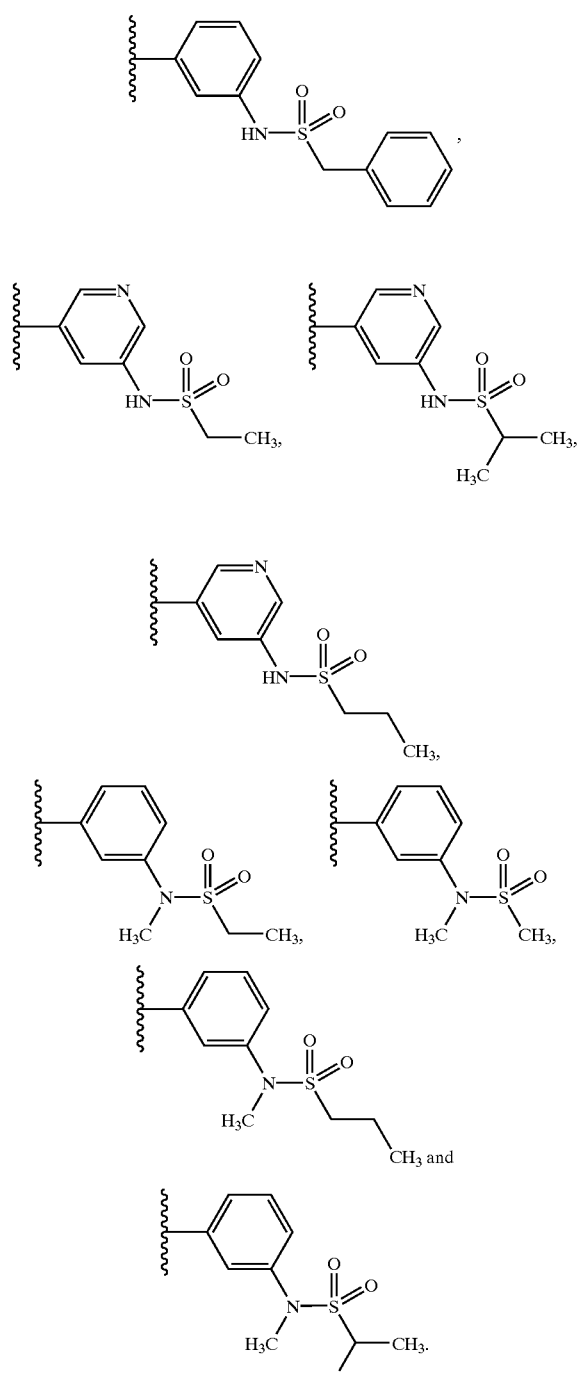
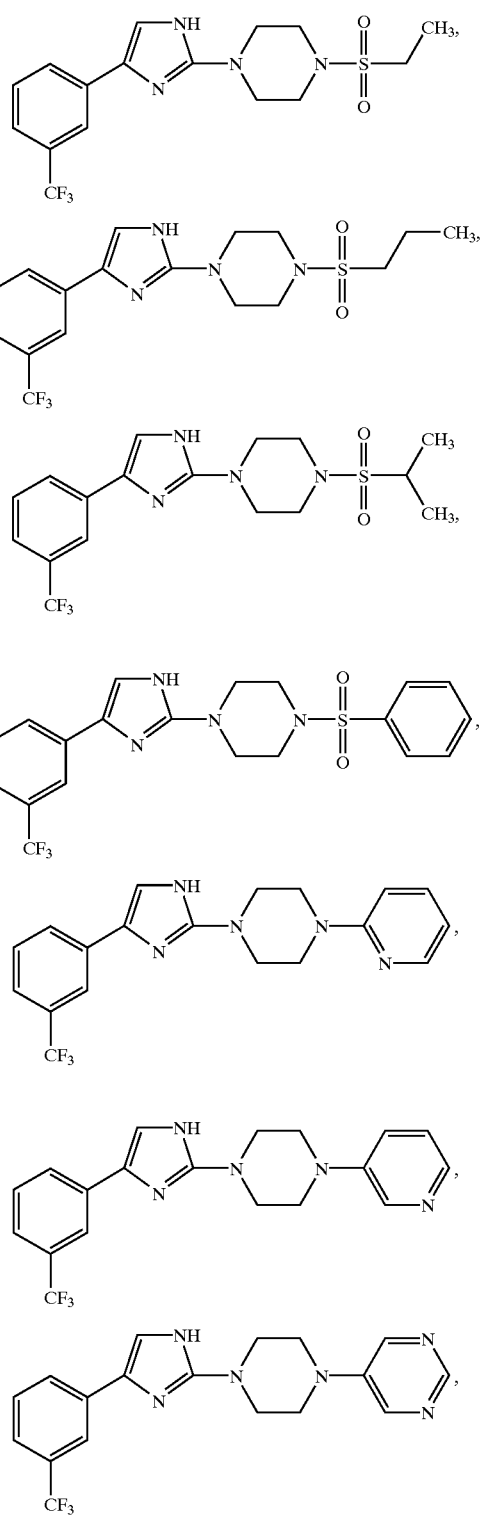
Still another group of preferred compounds of this invention include those selected from the group consisting of:

-continued
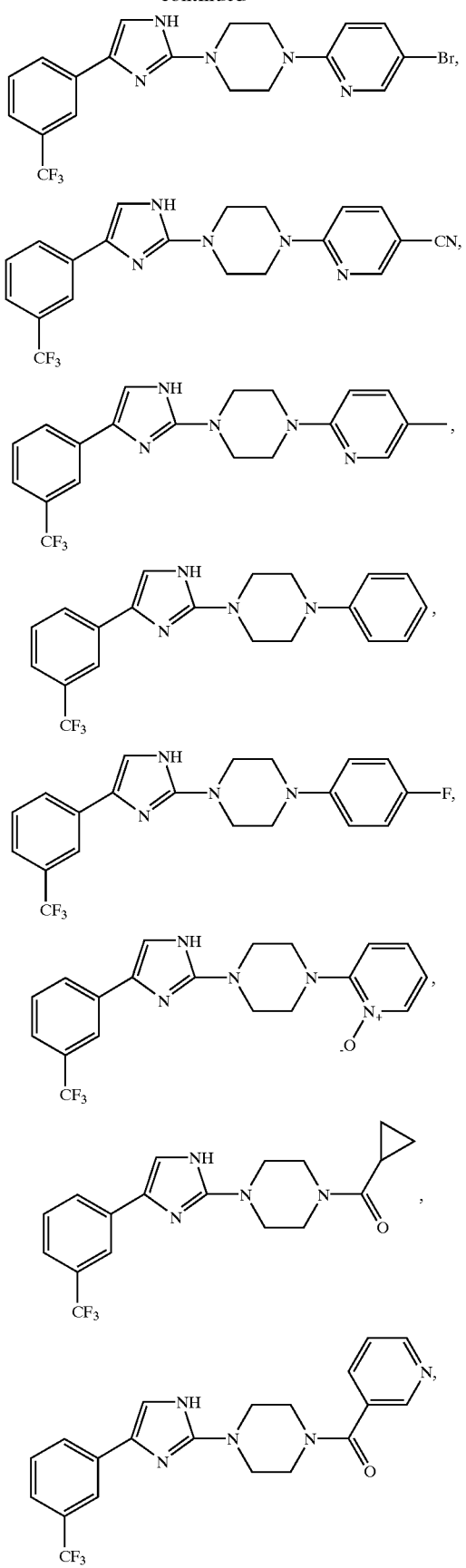
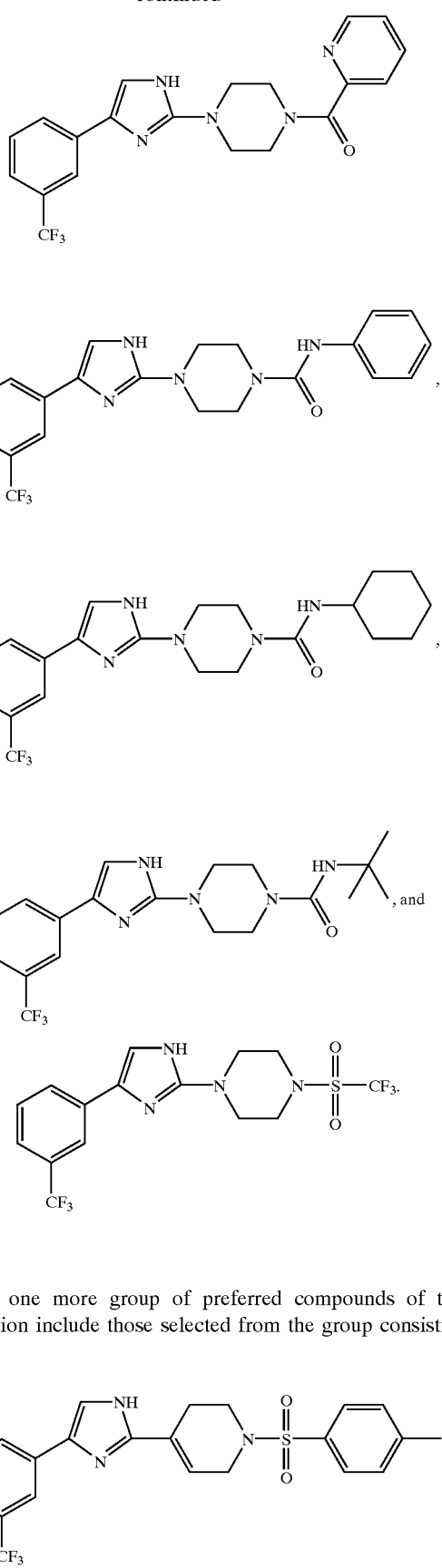
Yet one more group of preferred compounds of this invention include those selected from the group consisting of:
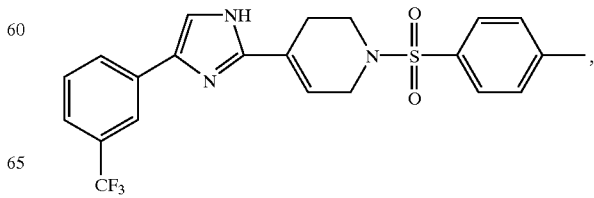

-continued

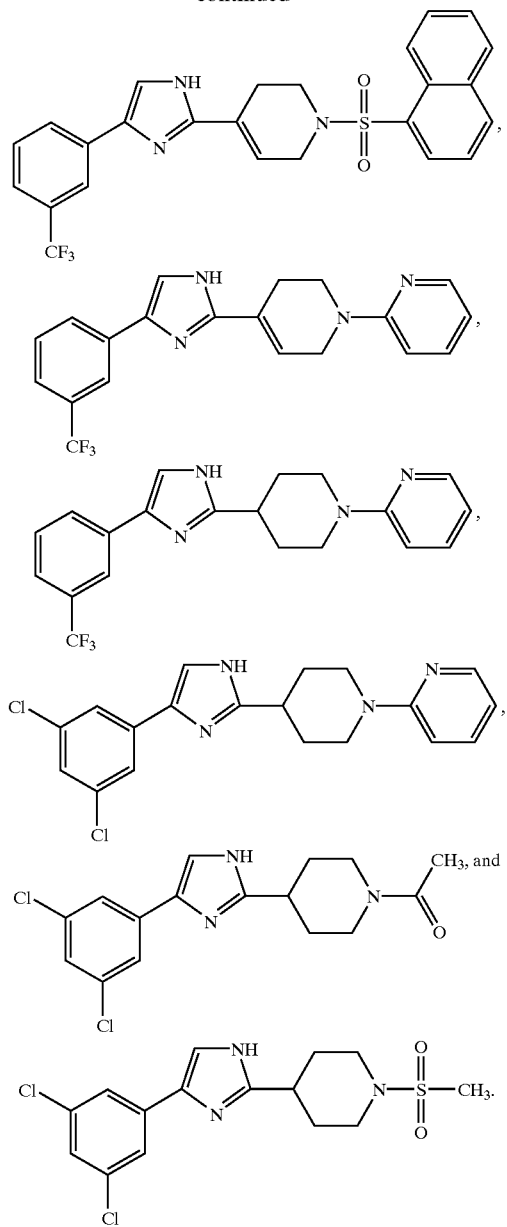

The present invention also relates to a method of treating eating disorders, such as obesity and hyperphagia, and diabetes comprising administering to a mammal in need of such treatment an effective amount of a compound of formula I.

Another aspect of the invention is a pharmaceutical composition for treating eating disorders and diabetes which comprises a compound of formula I in combination with a pharmaceutically acceptable carrier.

DETAILED DESCRIPTION

Except where stated otherwise, the following definitions apply throughout the present specification and claims. These definitions apply regardless of whether a term is used by itself or in combination with other terms. Hence the definition of "alkyl" applies to "alkyl" as well as the "alkyl" portions of "alkoxy", etc.

Alkyl represents a straight or branched saturated hydrocarbon chain having the designated number of carbon atoms.

If the number of carbon atoms is not specified, e.g., if the term lower alkyl is used, chain lengths of 1 to 6 carbons are intended.

Aryl-(including the aryl portion of arylalkyl and heteroarylalkyl)-represents a carbocyclic group containing from 6 to 15 carbon atoms and having at least one aromatic ring (e.g., aryl is a phenyl ring), with all available substitutable carbon atoms of the carbocyclic group being intended as possible points of attachment, said carbocyclic group being optionally substituted with one or more (e.g., 1 to 3) of halo, alkyl, hydroxy, alkoxy, phenoxy, $CF_3$, —C(O)N($R^{18}$)$_2$, —$SO_2R^{18}$, —$SO_2N(R^{18})_2$, amino, alkylamino, dialkylamino, —COOR or —$NO_2$, wherein $R^{18}$ represents H, alkyl, aryl, arylalkyl, heteroaryl or cycloalkyl and $R^{23}$ represents alkyl or aryl;

Cycloalkyl represents a saturated carbocyclic ring having 3 to 7 carbon atoms.

Halogeno represents fluoro, chloro, bromo or iodo.

As defined above, heterocycloalkyl represents 4 to 6 membered rings comprising 3 to 5 carbon ring members and 1 to 3 ring members selected from the group consisting of —$NR^{12}$—, —O— and —S—. Where a heterocycloalkyl ring comprises more than one heteroatom, no rings are formed where there are adjacent oxygen atoms, adjacent sulfur atoms, or three consecutive heteroatoms. Examples of heterocycloalkyl rings are piperazinyl, tetrahydrofuranyl, pyrrolidinyl, piperidinyl, morpholinyl and thiomorpholinyl.

Heteroaryl means a 5 or 6-membered aromatic ring comprising 1 to 3 heteroatoms independently selected from the group consisting of —O—, —S— and —N═, provided that the rings do not include adjacent oxygen and/or sulfur atoms. Examples of heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. The heteroaryl rings are attached to the rest of the molecule through a ring carbon atom. All positional isomers are contemplated, e.g., 2-pyridyl, 3-pyridyl and 4-pyridyl. The substituted heteroaryl groups specifically identified in the definition of R, e.g. $R^2$-pyridyl and $R^3$-thiazolyl, can be substituted at any available ring carbon atom.

When a variable appears more than once in the structural formula, for example $R^1$, the identity of each variable appearing more than once may be independently selected from the definition for that variable.

Compounds of the invention are tautomeric with respect to the 4- and 5-positions of the imidazoyl ring, i.e., the following structural formulae are equivalent:

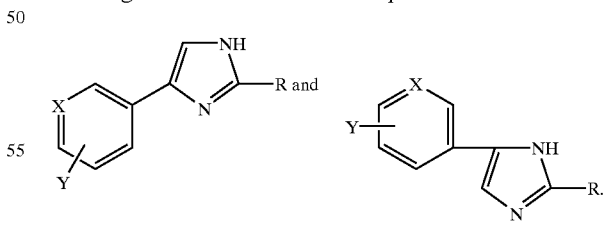

N-oxides can form on a tertiary nitrogen present in an R substituent (e.g., R is 3-pyridyl N-oxide) or when X is ═N—, in the Y substituted ring.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compounds of formula I may be produced by processes known to those skilled in the art as shown in the following reaction schemes and in the preparations and examples below.

Scheme 1:

Compounds of formula 1a or 1b wherein X is —CH═ and R is $R^1$-phenyl or $R^1$-pyridyl, respectively, can be prepared by the following procedure wherein the imidazolyl ring is formed during the reaction:

followed by deprotection of the resultant intermediate of formula IV, as shown in the following typical reaction scheme, wherein SEM is (2-trimethylsilyl)ethoxymethyl:

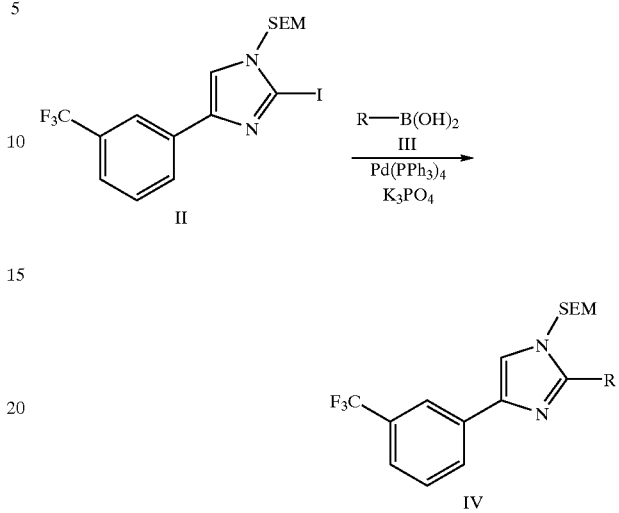

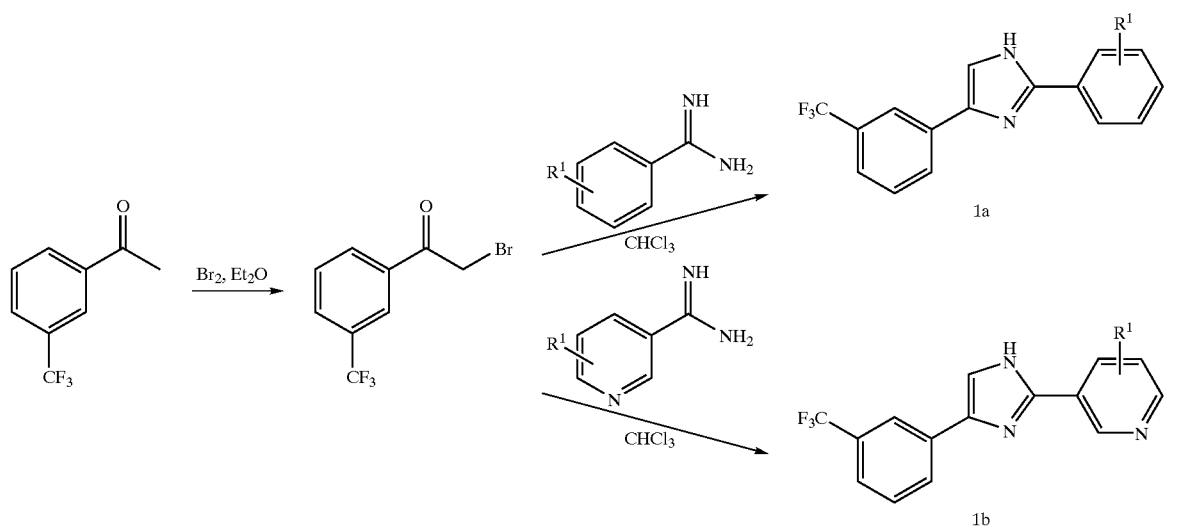

CF$_3$-substituted acetophenone is brominated, then reacted with a phenyl- or pyridyl-substituted amidine to obtain compounds of formula 1a or 1b. Compounds prepared by this method can be converted to other compounds of formula I by treating the $R^1$ substituent using methods well known in the art to obtain other $R^1$ substituents, e.g., an ester can be converted to an acid, an acid can be condensed with an amine, a nitro group can be reduced to an amine, and an amine can be sulfonated. When necessary, the NH moiety of the imidazolyl ring is protected with a group such as (2-trimethylsilyl)ethoxymethyl prior to reaction.

Scheme 2:

Compounds of formula 1c wherein X is ═CH— can be prepared by reacting an N-protected (CF$_3$-phenyl)-substituted imidazole of formula II with an R-containing reagent, for example an R-boronic acid of formula III, -continued Scheme 3:

Compounds of formula 1 d wherein R is a substituted 1,2,5,6-tetrahydropyridyl of the formula

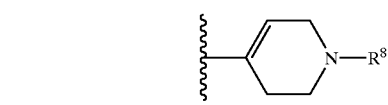

can be prepared by reacting an N-protected (CF$_3$-phenyl)-substituted imidazole with an N-protected 4-piperidone, followed by dehydration of the resultant intermediate of formula VII, as shown in the following typical reaction-scheme wherein R$^8$ is —SO$_2$—R$^7$:

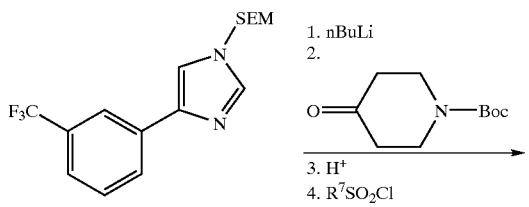

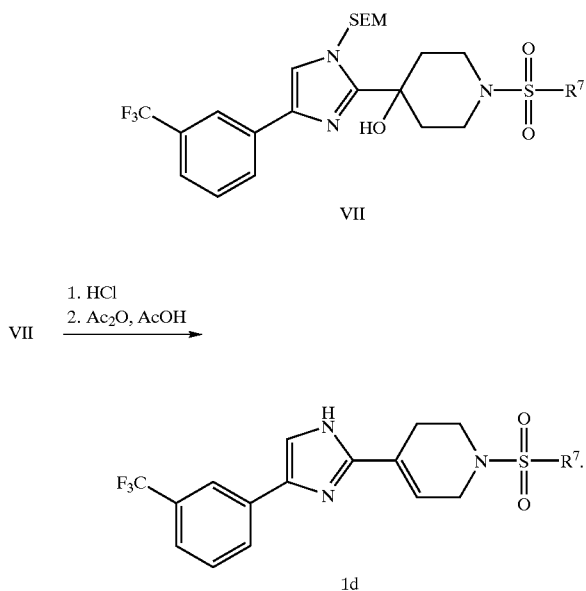

Alternatively, compounds of formula 1d wherein X is =CH— can be prepared by reacting an N-protected (CF$_3$-phenyl)-substituted imidazole with an N-protected 4-(trifluoromethanesulfonyloxy)-1,2,5,6-tetrahydropyridine of formula VIII, followed by deprotection of the resultant intermediate of formula IX.

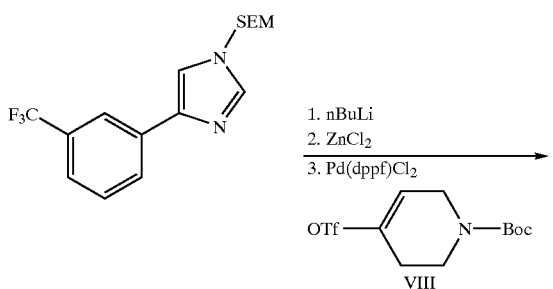

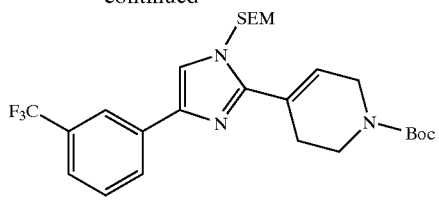

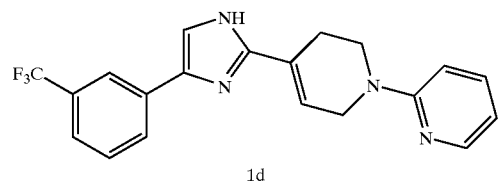

Compounds of formula 1d can be converted to compounds of formula I wherein R is N-substituted-4-piperidyl by reducing the compound of formula 1d, for example by hydrogenation.

Scheme 4:

Compounds of formula 1e wherein R is an N-R$^8$-substituted piperidinylmethyl can be prepared by reacting an N-protected (CF$_3$-phenyl)-substituted imidazole of formula II with an N-protected 4-methylenepiperidine. After deprotection of the piperidinyl moiety of the resultant intermediate of formula X, using procedures well known in the art, the piperidyl nitrogen on the intermediate of formula XI is substituted with R$^8$ and the protecting group on the imidazolyl nitrogen is removed:

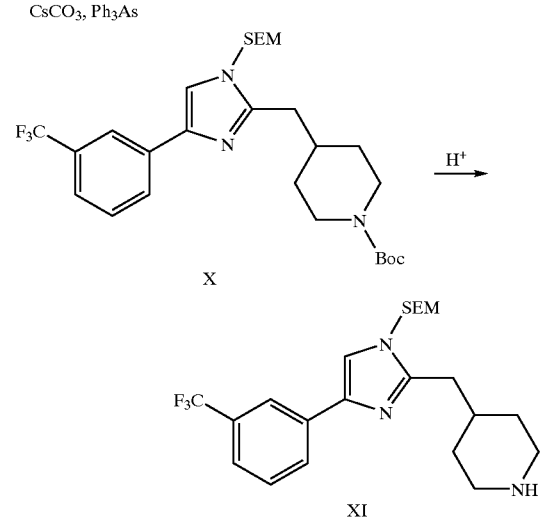

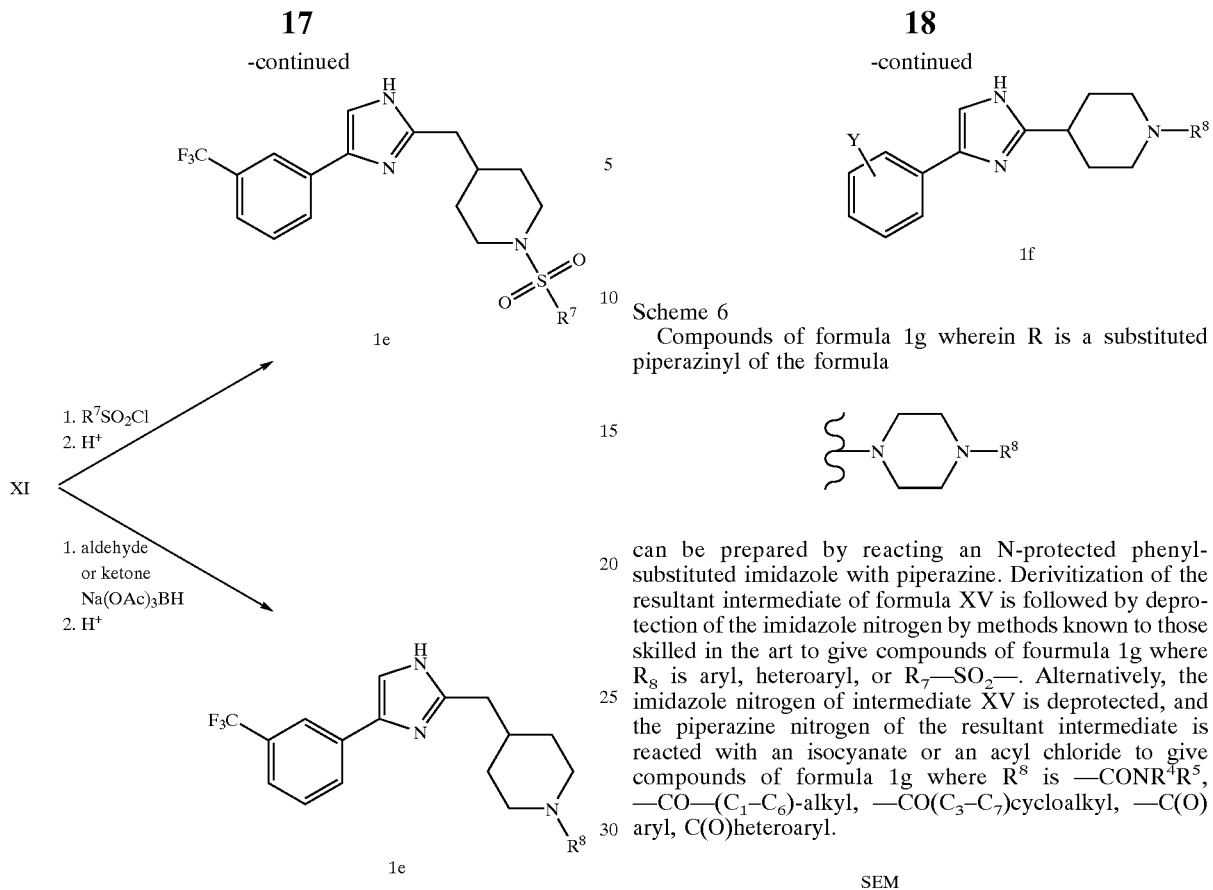

Scheme 6

Compounds of formula 1g wherein R is a substituted piperazinyl of the formula can be prepared by reacting an N-protected phenyl-substituted imidazole with piperazine. Derivitization of the resultant intermediate of formula XV is followed by deprotection of the imidazole nitrogen by methods known to those skilled in the art to give compounds of fourmula 1g where $R_8$ is aryl, heteroaryl, or $R_7$—$SO_2$—. Alternatively, the imidazole nitrogen of intermediate XV is deprotected, and the piperazine nitrogen of the resultant intermediate is reacted with an isocyanate or an acyl chloride to give compounds of formula 1g where $R^8$ is —$CONR^4R^5$, —CO—$(C_1$–$C_6)$-alkyl, —CO$(C_3$–$C_7)$cycloalkyl, —C(O)aryl, C(O)heteroaryl.

Scheme 5

A method of preparation of compounds of formula if wherein R is N-substituted-4-piperidyl is by reacting a 5- (or 4-) -bromo-2-(N-protected-4-piperidyl)imidazole of formula XII with an aryl boronic acid of formula XIII. After deprotection of the piperidinyl moiety of the resultant intermediate, using procedures well known in the art, the piperidyl nitrogen on the intermediate of formula XIV is substituted with $R^8$ and the protecting group on the imidazole nitrogen is removed.

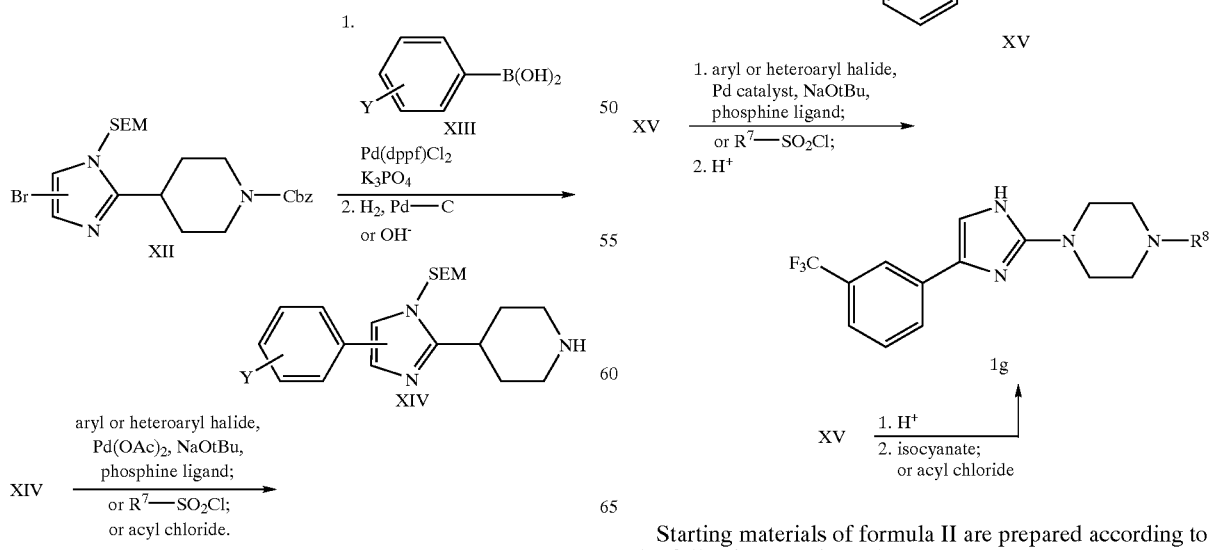

Starting materials of formula II are prepared according to the following reaction scheme:

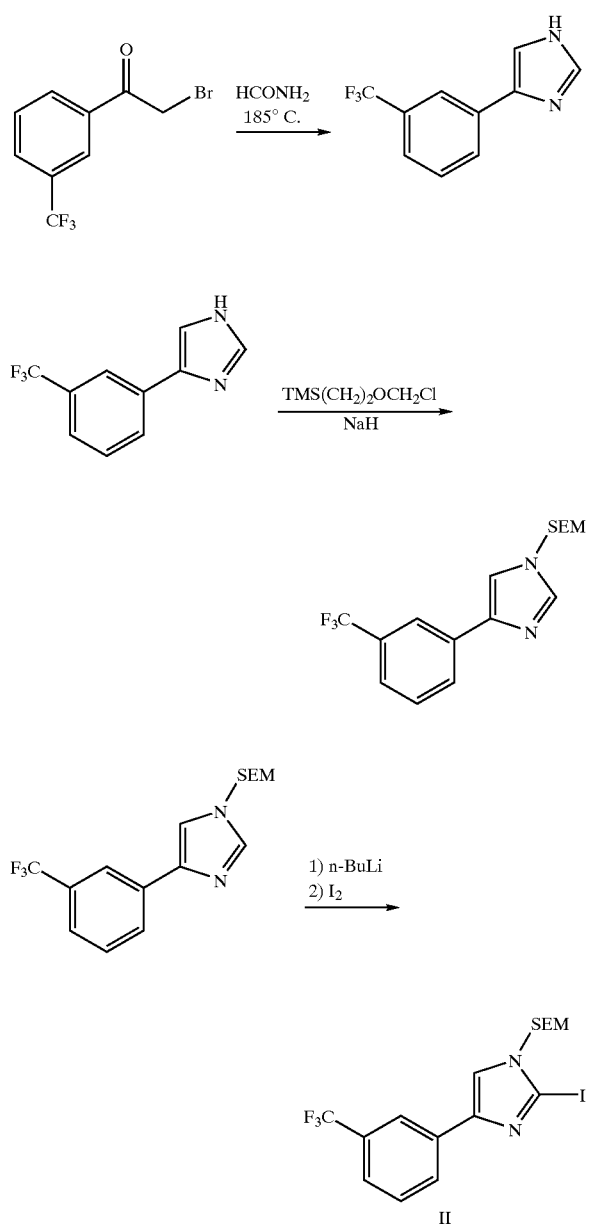

α-Bromo-(3-trifluoromethyl)acetophenone is condensed with formamide and a (2-trimethylsilyl)ethoxymethyl group is placed on the imidazole nitrogen. The 2-position of the imidazolyl group is iodinated to obtain the starting material of formula II.

Starting material of formula XII is prepared according to the following scheme;

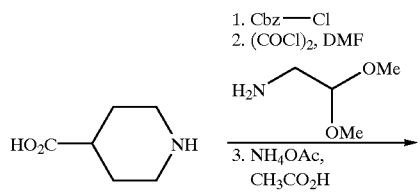

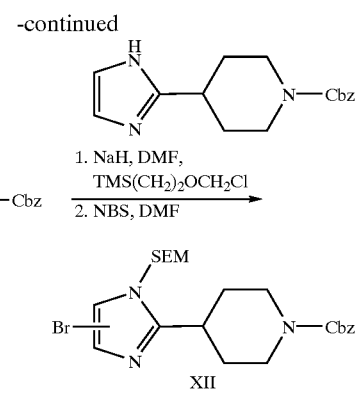

Isonipecotic acid is condensed with aminoacetaldehyde dimethyl acetal and the product is reacted with ammonium acetate to form an imidazole substituted at the 2-position by N-protected 4-piperidinyl. A (2-trimethylsilyl) ethoxyoxymethyl group is placed on the imidazole nitrogen and the resultant product is brominated to give a mixture of regioisomeric 4- and 5-bromoimidazoles of formula XII.

The pyridyl amidine shown in Scheme 1 is prepared by treating 3-cyanopyridine with an ammonia equivalent such as LHMDS or methylchloroaluminum amide.

Substituted amidines used in the method of Scheme 1 are known or can be prepared by known procedures.

The compounds of formula I exhibit selective neuropeptide Y Y5 antagonizing activity, which has been correlated with pharmaceutical activity for treating eating disorders, such as obesity and hyperphagia, and diabetes.

The compounds of formula I display pharmacological activity in test procedures designated to indicate neuropeptide Y Y5 receptor antagonist activity. The compounds are non-toxic at pharmaceutically therapeutic doses. Following are descriptions of the test procedures.

cAMP Assay

CHO cells expressing NPY $Y_5$ receptors were maintained in Ham's F-12 media (Gibco-BRL) supplemented with 10% FCS (ICN), 1% penicillin-streptomycin, 1% non-essential amino acids and 200 µg/ml Geneticin (GibcoBRL #11811-031) under a humidified 5% $CO_2$ atmosphere. Two days prior to assay, cells were released from T-175 tissue culture flasks using cell dissociation solution (1×; non-enzymatic [Sigma #C-5914]) and seeded into 96-well, flat-bottom tissue culture plates at a density of 15,000 to 20,000 cells per well. After approximately 48 hours, the cell monolayers were rinsed with Hank's balanced salt solution (HBSS) then preincubated with approximately 150 µl/well of assay buffer (HBSS supplemented with 4 mM $MgCl_2$, 10 mM HEPES, 0.2% BSA [HH]) containing 1 mM 3-isobutyl-1-methylxanthine ([IBMX] Sigma #I-5879) with or without the antagonist compound of interest at 37° C. After 20 minutes the 1 mM IBMX-HH assay buffer (± antagonist compound) was removed and replaced with assay buffer containing 1.5 µM forskolin (Sigma #F-6886) and various concentrations of NPY in the presence or absence of one concentration of the antagonist compound of interest. At the end of 10 minutes, the media were removed and the cell monolayers treated with 75 µl ethanol. The tissue culture plates were agitated on a platform shaker for 15 minutes, after which the plates were transferred to a warm water bath in order to evaporate the ethanol. Upon bringing all wells to dryness, the cell residues were resolubilized with 250 μl FlashPlate assay buffer. The amount of cAMP in each well was quantified using the [$^{125}$I]-cAMP FlashPlate kit (NEN #SMP-001) and according to the protocol provided by the manufacturer. Data were expressed as either pmol cAMP/ml or as percent of control. All data points were determined in triplicate and $EC_{50}$'s (nM) were calculated using a nonlinear (sigmoidal) regression equation (GraphPad Prism™). The $K_B$ of the antagonist compound was estimated using the following formula:

$$K_B=[B]/(1-\{[A']/[A]\})$$

where [A] is the $EC_{50}$ of the agonist (NPY) in the absence of antagonist,

[A'] is the $EC_{50}$ of the agonist (NPY) in the presence of antagonist, and [B] is the concentration of the antagonist.

NPY Receptor Binding Assay

Human NPY $Y_5$ receptors were expressed in CHO cells. Binding assays were performed in 50 mM HEPES, pH 7.2, 2.5 mM $CaCl_2$, 1 mM $MgCl_2$ and 0.1% BSA containing 5–10 μg of membrane protein and 0.1 nM $^{125}$I-peptide YY in a total volume of 200 μl. Non-specific binding was determined in the presence of 1 uM NPY. The reaction mixtures were incubated for 90 minutes at room temperature, then filtered through Millipore MAFC glass fiber filter plates which had been pre-soaked in 0.5% polyethyleneimine. The filters were washed with phosphate-buffered saline, and radioactivity was measured in a Packard TopCount scintillation counter.

For the compounds of this invention, a range of neuropeptide Y5 receptor binding activity from about 0.5 nM to about 1000 nM was observed. Compounds of this invention preferably have a binding activity in the range of about 0.5 nM to 500 nM, more preferably about 0.5 to 100 nM, and most preferably about 0.5 to 10 nM.

Neuropeptide Y Y5 receptor binding activity results for representative compounds of the invention are as follows:

| Ex. | r/h Y5 Ki nM |
|---|---|
| 1A | 3 |
| 1B | 52 |
| 2A | 315 |
| 3 | 17 |
| 5A | 1.4 |
| 6A | 2.1 |
| 10A | 63 |
| 19 | 1.7 |
| 21C | 2 |
| 26 | 1.4 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The invention disclosed herein is exemplified by the following preparations and examples which should not be construed to limit the scope of the disclosure. Alternative mechanistic pathways and analogous structures may be apparent to those skilled in the art.

In the preparations and examples, the following abbreviations are used: room temperature (R.T.), phenyl (Ph), acetyl (Ac), ether (Et$_2$O), ethyl acetate (EtOAc), dimethylformamide (DMF), tetrabutyl ammonium fluoride (TBAF), tetrahydrofuran (THF), ethanol (EtOH), lithium aluminum hydride (LAH), 4-(dimethylamino)pyridine (DMAP), preparative thin layer chromatography (PTLC), 1,1'-bis(diphenylphosphino)ferrocene (dppf), lithium hexamethyidisilazide (LHMDS) and-1-(3-dimethyl(aminopropyl)-3-ethyl-carbodiimide hydrochloride (EDCl).

PREPARATION 1

Preparation 1

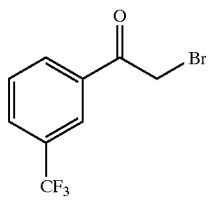

To a stirred solution of 3'-(trifluoromethyl)acetophenone (4.0 ml, 26 mmol) in Et$_2$O (26 ml) under N$_2$ was added bromine (1.4 ml, 26 mmol) dropwise over 1 h. The reaction was stirred at R.T. for 30 min., then poured slowly into sat'd NaHCO$_3$. The organic portion was washed with brine, dried (MgSO$_4$), filtered and concentrated. Purification by flash chromatography (2:3 CH$_2$Cl$_2$/hexanes) yielded Preparation 1 (4.3 g, 61%). $^1$H NMR (400 MHz, CDCl$_3$): δ 8.31 (s, 1H), 8.24 (d, 1H, J=7.8 Hz), 7.93 (d, 1H, J=7.8 Hz), 7.72 (t, 1H, J=7.8 Hz), 4.52 (s, 2H).

PREPARATION 2

Preparation 2

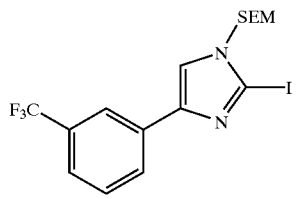

Step 1:

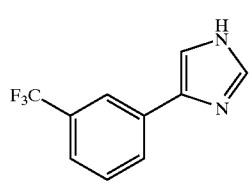

A solution of Preparation 1 (5.53 g, 20.7 mmol) in formamide (32 ml) was heated at 185° C. in a sealed pressure tube for 3 h. The reaction mixture was allowed to cool to R.T., then poured into aqueous sat'd NaHCO$_3$ solution (120 ml) and extracted with EtOAc (2×100 ml). The organic layer was washed with water (60 ml) and sat'd NaCl (60 ml), then dried (MgSO$_4$), filtered and concentrated. Purification of the residue by column chromatography (CH$_2$Cl$_2$, then gradient of increasing CH$_3$OH concentration to 5:95 CH$_3$OH/CH$_2$Cl$_2$) gave a white solid (3.83 g, 87%). $^1$H NMR (400 MHz, CDCl$_3$): δ 8.09 (bs, 1H), 8.01 (m, 1H), 7.90 (bs, 1H), 7.57 (m, 2H), 7.49 (bs, 1H). MS m/e 213 (M+H)$^+$.

Step 2:

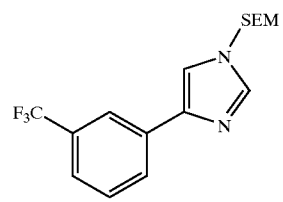

To a stirred, ice-cold solution of the product of Step 1 (0.70 g, 3.3 mmol) in THF (13 ml) under N$_2$ was added 95% NaH (0.10 g, 4.3 mmol). After 20 min., (2-trimethylsilyl)ethoxymethyl chloride (0.70 ml, 4.0 mmol) was added dropwise over 5 min. The reaction was warmed to R.T. After 2 h, Et$_2$O was added, and the whole washed with water, dried (MgSO$_4$), filtered and concentrated under vacuum. Purification by flash chromatography (20:80, then 40:60 EtOAc/hexanes) yielded the product (0.69 g, 61%). $^1$H NMR (400 MHz, CDCl$_3$): δ 8.11 (bs, 1H), 8.03 (m, 1H), 7.74 (d, 1H, J=1.3 Hz), 7.56 (m, 2H), 7.47 (d, 1H, J=1.3 Hz), 5.38 (s, 2H), 3.60 (t, 2H, J=8.2 Hz), 1.00 (t, 2H, J=8.2 Hz), 0.07 (s, 9H). HRMS: Calcd for C$_{16}$H$_{21}$N$_2$ OF$_3$Si (M+H)$^+$: 343.1454. Found: 343.1452.

Step 3:

A 1.6N solution of n-BuLi in hexanes (1.4 ml, 2.3 mmol) was added dropwise to a stirred −78° C. solution of the product of Step 2 (0.52 g, 1.5 mmol) in THF (15 ml) under N$_2$. Immediately after the addition was complete, a solution of iodine (0.58 g, 2.3 mmol) in THF (4.5 ml) was added dropwise over 10 min. After warming to R.T. over 1 h, the reaction was diluted with CH$_2$Cl$_2$ and water. The organic layer was washed with sat'd aqueous Na$_2$S$_2$O$_3$ and water, then dried (MgSO$_4$), filtered and concentrated under vacuum to give the title compound (0.71 g) which was used without further purification. $^1$H NMR (400 MHz, CDCl$_3$): δ 8.07 (bs, 1H), 7.99 (m, 1H), 7.56 (m, 3H), 5.34 (s, 2H), 3.65 (t, 2H, J=8.2 Hz), 1.02 (t, 2H, J=8.2 Hz), 0.07 (s, 9H). MS m/e 469 (M+H)$^+$.

PREPARATION 3

Preparation 3

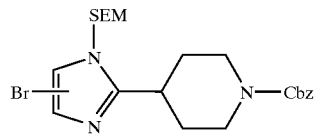

Step 1:

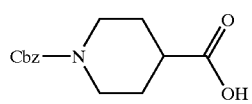

Isonipecotic acid (5.118 g, 39.63 mmol) and potassium carbonate (12.94 g, 93.63 mmol) were dissolved in water (52 ml). The solution was cooled in an ice-water bath and benzyl chloroformate (7.3 ml, 51 mmol) was added dropwise. The mixture was brought to R.T. and stirred for 16 h. The reaction was extracted with EtOAc (3×30 ml). The aqueous layer was acidified to pH 1–2 with conc. HCl (15 ml) and then extracted with CH$_2$Cl$_2$ (3×60 ml). The combined organic layer was dried (Na$_2$SO$_4$) and concentrated to give the product (10.306 g, 99%). $^1$H-NMR (400 MHz, CDCl$_3$) δ 7.32 (5H, m), 5.11 (2H, s), 4.09 (2H, m), 2.93 (2H, m), 2.50 (1H, m), 1.90 (2H, m), 1.67 (2H, m).

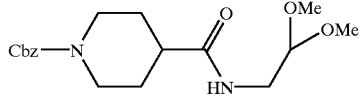

To a solution of the product of Step 1 (10.306 g, 39.186 mmol) in CH$_2$Cl$_2$ (100 ml) was added oxalyl chloride (5.138 g, 39.67 mmol) and drops of DMF. The solution was stirred at R.T. for 16 h. More CH$_2$Cl$_2$ (50 ml) was added and the solution was cooled in an ice-water bath. Triethylamine (11.99 g, 118.5 mmol) and aminoacetaldehyde dimethylacetal (4.183 g, 39.79 mmol) were added and the reaction was stirred at R.T. for 16 h. The mixture was washed with water (200 ml), saturated NH$_4$Cl (150 ml), 1N NaOH (200 ml), and brine (200 ml). The organic layer was dried (K$_2$CO$_3$), concentrated, and purified by a flash column (CH$_2$Cl$_2$, then gradient of increasing concentration of MeOH to 1.5:98.5 MeOH/CH$_2$Cl$_2$) to give the product (10.096 g, 74%). MS (ES) m/e 351 (M+H)$^+$.
Step 3:

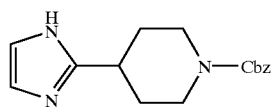

A solution of the product of Step 2 (5.09 g, 14.5 mmol) and ammonium acetate (32.0 g, 415 mmol) in glacial acetic acid (25 ml) was refluxed for 5 h. The volatiles were evaporated in vacuo and the residue was partitioned between CH$_2$Cl$_2$ (2×100 ml) and aqueous NH$_4$OH (80 ml). The organic layer was dried (MgSO$_4$), concentrated, and purified by a flash column (hexanes, then gradient of increasing EtOAc concentration to 100% EtOAc) to give the product (1.909 g, 46%). MS (ES) m/e 286 (M+H)$^+$.
Step 4:

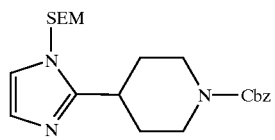

A mixture of the product of Step 3 (1.844 g, 6.471 mmol) and 60% sodium hydride dispersion in mineral oil (0.355 g, 8.875 mmol) in dry DMF (20 ml) was stirred for 1 h. (2-Trimethylsilyl)ethoxymethyl chloride (1.396 g, 7.643 mmol) was added and the mixture was stirred for 3 days. DMF was evaporated in vacuo and the residue was partitioned between EtOAc (100 ml) and water (3×100 ml). The organic layer was dried (MgSO$_4$), concentrated, and purified by a flash column (1:99 MeOH/CH$_2$Cl$_2$, then 2:98 MeOH/CH$_2$Cl$_2$) yielded the product (2.420 g, 90%). MS (ES) m/e 416 (M+H)$^+$.
Step 5:

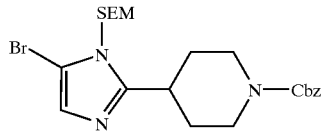

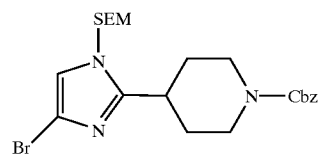

To an ice-cold solution of the product of Step 4 (1.601 g, 3.858 mmol) in DMF (15 ml) was added N-bromosuccinimide (0.383 g, 2.15 mmol). After 0.5 h another portion of N-bromosuccinimide (0.313 g, 1.76 mmol) was added. The solution was warmed to R.T. and stirred for 3 h. DMF was evaporated in vacuo and the residue was partitioned between EtOAc (200 ml) and 0.5N NaOH (80 ml). The organic layer was washed with water (100 ml) and dried over MgSO$_4$. Evaporation followed by flash chromatography (CH$_2$Cl$_2$, then gradient of increasing MeOH concentration to 1:99 MeOH/CH$_2$Cl$_2$) gave the product as a mixture of 4- and 5-bromo regioisomers. Major, more polar isomer (1.042 g, 54%), MS (ES) m/e 496 (M+H)$^+$. Minor regioisomer (0.339 g, 18%), MS (ES) m/e 496 (M+H)$^+$.

EXAMPLE 1

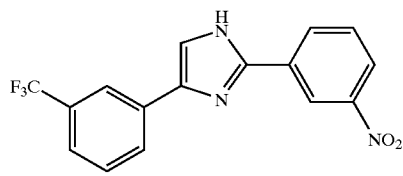

To a stirred solution of 3-nitrobenzamidine (5.4 g, 33 mmol) in DMF (80 ml) was added Na$_2$CO$_3$ (2.8 g, 26 mmol) followed by Preparation 1 (3.4 g, 13 mmol), and the mixture was heated at 80° C. for 5 h. The reaction mixture was diluted with EtOAc and washed several times with H$_2$O. The organic layer was dried (MgSO$_4$), filtered, and concentrated. Flash chromatography of the residue (1:99 CH$_3$OH/CH$_2$Cl$_2$) afforded the product (3.73 g, 86%). $^1$H NMR (400 MHz, CDCl$_3$) δ 8.74 (1H, bs), 8.41 (1H, d, J=7.7 Hz), 8.28 (1H, d, J=8.2 Hz), 8.14 (s, 1H), 8.07 (m, 1H), 7.70 (1H, t, J=7.9 Hz), 7.59 (m, 3H). HRMS (FAB): Calcd. for C$_{16}$H$_{10}$N$_3$O$_2$F$_3$ (M+H)$^+$: 334.0803. Found: 334.0815.

Using appropriate starting materials and essentially the same procedure, compounds of the following structure were prepared:

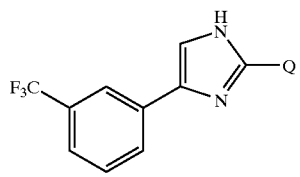
| Ex. | Q | MF | HRMS Calculated | HRMS Found |
|---|---|---|---|---|
| 1A | (adamantyl) | $C_{20}H_{21}N_2F_3$ | 347.1735 | 347.1738 |
| 1B | (3-methoxycarbonylphenyl) | $C_{18}H_{13}N_2O_2F_3$ | 347.1007 | 347.1012 |
| 1C | —CH$_3$ | $C_{11}H_9N_2F_3$ | 227.0796 | 227.0797 |
| 1D | (CH$_2$OPh) | $C_{17}H_{13}N_2OF_3$ | 319.1058 | 319.1055 |
| 1E | —C(CH$_3$)$_3$ | $C_{14}H_{15}N_2F_3$ | 269.1266 | 269.1261 |
| 1F | —CF$_3$ | $C_{11}H_6N_2F_6$ | 281.0513 | 281.0510 |
| 1G | (CH$_2$SPh) | $C_{17}H_{13}N_2SF_3$ | 335.0830 | 335.0829 |
| 1H | (CH$_2$O-2,4,6-trimethylphenyl) | $C_{20}H_{19}N_2OF_3$ | 361.1528 | 361.1531 |

The following compounds were prepared by condensation of the appropriate amidine and the product of Preparation 1 by essentially the same procedure, except that the requisite amidines were prepared from CH$_3$Al(Cl)NH$_2$ (the preparation of which is described in Example 7, Step 1) and the appropriate nitrile by the procedure described in Example 7, Step 2.

| Ex. | Q | Physical Data |
|---|---|---|
| 1I | cyclohexyl | HRMS: calc. 295.1422 found 295.1431 |
| 1J | cycloheptyl | MS: 309 (M + H)$^+$ |
| 1K | cyclopropyl | HRMS: calc. 253.0953 found 253.0944 |
| 1L | cyclobutyl | HRMS: calc. 267.1109 found 267.1100 |
| 1M | cyclopentyl | HRMS: calc. 281.1266 found 281.1266 |
| 1N | benzyl | HRMS: calc. 303.1109 found 303.1110 |
| 1O | 1-phenylcyclopropyl | MS: 329 (M + H)$^+$ |
| 1P | 1-phenylcyclobutyl | MS: 343 (M + H)$^+$ |
| 1Q | 1-phenylcyclohexyl | MS: 371 (M + H)$^+$ |
| 1R | 1-(4-methylphenyl)cyclopentyl | MS: 371 (M + H)$^+$ |
| 1S | 1-phenylethyl | MS: 317 (M + H)$^+$ |
| 1T | 2-phenylpropan-2-yl | MS: 331 (M + H)$^+$ |
| 1U | 4-pyridylmethyl | MS: 304 (M + H)$^+$ |

EXAMPLE 2

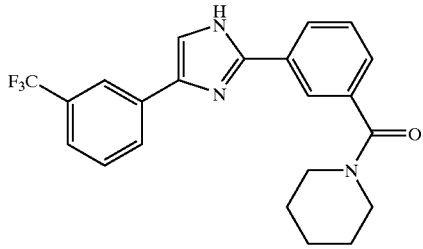

Step 1:

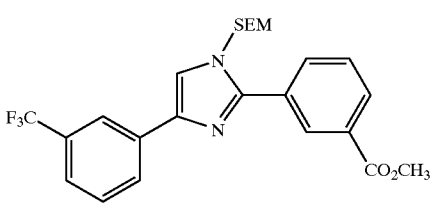

Using the procedure of Preparation 2, Step 2, reaction of the product of Example 1B (0.98 g, 2.8 mmol) with NaH and (2-trimethylsilyl)ethoxymethyl chloride afforded the product (1.1 g, 85%).

Step 2:

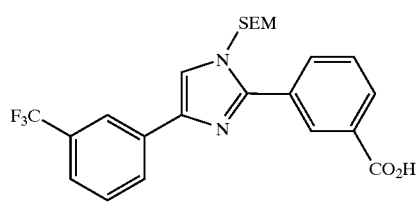

The product of Step 1 (1.1 g, 2.3 mmol) was dissolved in $CH_3OH$ (30 ml) and $H_2O$ (10 ml), then $LiOH \cdot H_2O$ (0.49 g, 12 mmol) was added. The reaction mixture was stirred for 15 h at R.T., acidified with 1 N HCl and extracted with $CH_2Cl_2$. The organic layer was evaporated to give the product (0.98 g, 92%), which was used in Step 3 without further purification. H NMR (400 MHz, $CDCl_3$): δ 8.67 (m, 1H), 8.16 (m, 4H), 7.65 (t, 1H, J=7.6 Hz), 7.57 (m, 3H), 5.41 (s, 2H), 3.70 (t, 2H, J=8.3 Hz), 1.04 (t, 2H, J=8.3 Hz), 0.06 (s, 9H). MS (Cl) m/e 463 $(M+H)^+$.

Step 3:

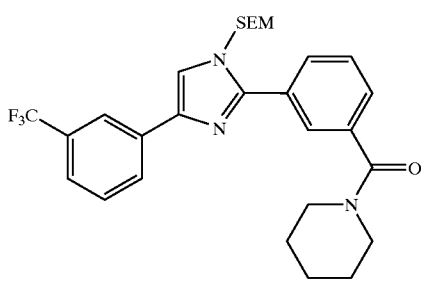

To a solution of the product of Step 2 (50 mg, 0.11 mmol), EDCl (31 mg, 0.16 mmol) and DMAP (14 mg, 0.11 mmol) in $CH_2Cl_2$ (1.0 ml) was added piperidine (10 μL, 0.13 mmol). The reaction was stirred at R.T. for 17 h, then more EDCl (17 mg, 0.090 mmol) and DMAP (7.0 mg, 0.055 mmol) were added. The reaction was stirred for an additional 48 h, washed with 1 N NaOH, extracted with $CH_2Cl_2$, dried ($MgSO_4$), filtered and concentrated under vacuum. Purification via PTLC (5:95 $CH_3OH/CH_2Cl_2$) yielded the product as a solid (41 mg, 70%). $^1$H NMR (400 MHz, $CDCl_3$): δ 8.16 (m, 1H), 8.07 (m, 1H), 7.95 (dd, 1H, J=1.6, 7.5 Hz), 7.90 (m, 1H), 7.62–7.51 (m, 5H), 5.35 (s, 2H), 3.78 (br s, 2H), 3.68 (t, 2H, J=8.2 Hz), 3.43 (br s, 2H), 1.59–1.74 (m, 6H), 1.01 (t, 2H, J=8.2 Hz), 0.06 (s, 9H). HRMS (FAB): Calc'd for $C_{28}H_{34}N_3O_2F_3Si$ $(M+H)+$ 530.2451. Found: 530.2440.

Step 4:

A solution of the product of Step 3 (41 mg, 0.080 mmol) in $CH_3OH$ (3.0 ml) and 6 N HCl (3.0 ml) was refluxed for 3 h. After cooling to R.T., the reaction was diluted with $CH_2Cl_2$, washed with 1 N NaOH, dried over $K_2CO_3$, filtered and concentrated under vacuum to give the crude product (25 mg, 79%), which was purified by PTLC (1:99 $CH_3OH/CH_2Cl_2$). $^1$H NMR (400 MHz, $CDCl_3$): δ 8.14 (bs, 1H), 8.01 (m, 2H), 7.85 (m, 1H), 7.54 (m, 2H), 7.49 (s, 1H), 7.36 (t, 1H, J=7.7 Hz), 7.22 (m, 1H), 3.82 (m, 2H), 3.41 (m, 2H), 1.76 (bs, 4H), 1.59 (m, 2H). MS (Cl) m/e 400 $(M+H)^+$.

Using appropriate starting materials and essentially the same procedure, the following compound was also prepared:

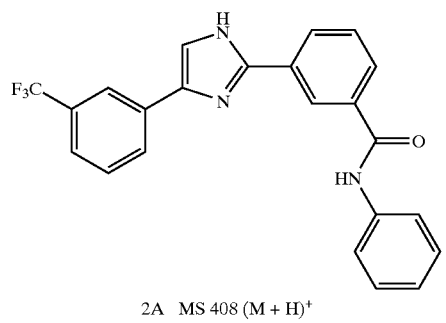

2A  MS 408 $(M + H)^+$

EXAMPLE 3

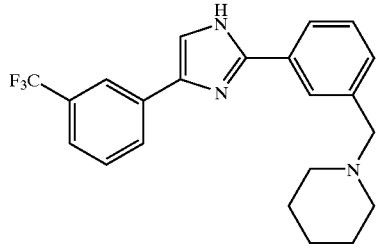

To a solution of Example 2 (20 mg, 0.050 mmol) in THF (1.8 ml) was added LAH (3.0 mg, 0.08 mmol). The reaction was stirred for 15 h at R.T., then more LAH (6.0 mg, 0.16 mmol) was added. The reaction was stirred for an additional 5 h, then 1 N NaOH was added. The mixture was extracted with $CH_2Cl_2$, dried over $K_2CO_3$, filtered and concentrated under vacuum. Purification by PTLC (5:95 $CH_3OH/CH_2Cl_2$) yielded the title compound (10 mg, 53%). $^1$H NMR (400 MHz, $CDCl_3$): δ 7.96–8.17 (m, 2H), 7.81–7.96 (m, 2H), 7.51 (m, 2H), 7.30–7.47 (m, 3H), 3.54 (s, 2H), 2.46 (bs, 4H), 1.63 (quintet, 4H, J=5.2 Hz), 1.49 (m, 2H). HRMS (FAB): Calc'd for $C_{22}H_{20}N_3F_3$ $(M+H)^+$: 386.1844. Found: 386.1836.

EXAMPLE 4

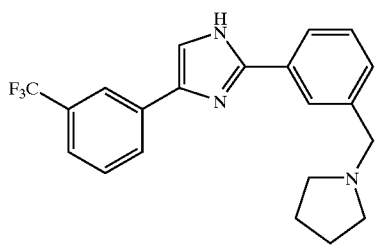

Step 1:

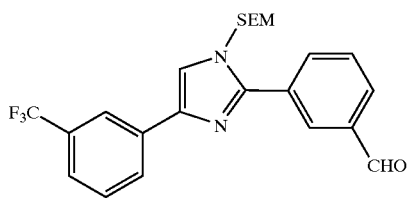

A mixture of Preparation 2 (661 mg, 1.41 mmol), 3-formylbenzeneboronic acid (433 mg, 2.88 mmol), Pd(dppf)Cl$_2$ (120 mg, 0.147 mmol), and K$_3$PO$_4$ (660 mg, 3.08 mmol) in 1,2-dimethoxyethane (11 ml) was purged with N$_2$, and heated at 95° C. overnight in a sealed vessel. The reaction mixture was allowed to cool, diluted with CH$_2$Cl$_2$ (60 ml), and filtered. The filtrate was washed with water (30 ml), dried (MgSO$_4$), filtered, and evaporated. Purification of the residue by flash chromatography (CH$_2$Cl$_2$, then 1:99 CH$_3$OH/CH$_2$Cl$_2$) afforded the product (492 mg, 78%). $^1$H NMR (400 MHz, CDCl$_3$): δ 10.09 (s, 1H), 8.39 (s, 1H), 8.2–7.9 (m, 4H), 7.67 (m, 1H), 7.52 (m, 3H), 5.33 (s, 2H), 3.66 (m, 2H), 0.98 (m, 2H), −0.02 (s, 9H).

Step 2:

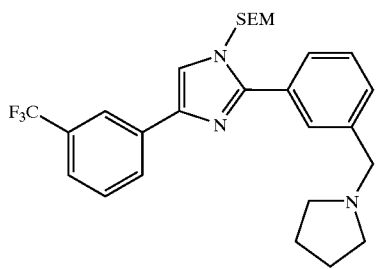

A mixture of the product of Step 1 (30 mg, 0.067 mmol), pyrrolidine (15 μl, 0.18 mmol), and sodium triacetoxyborohydride (22 mg, 0.10 mmol) in 1,2-dichloroethane (2 ml) was stirrred overnight. The mixture was partitioned between CH$_2$Cl$_2$ (35 ml) and 1N NaOH (10 ml). The organic layer was dried (MgSO$_4$), filtered and evaporated. Purification of the residue by PTLC (5:95 CH$_3$OH/CH$_2$Cl$_2$) gave the product (31 mg, 93%). $^1$H NMR (400 MHz, CDCl$_3$): δ 8.09 (s, 1H), 8.02 (m, 1H), 7.73 (m, 1H), 7.67 (m, 1H), 7.53–7.37 (m, 5H), 5.31 (s, 2H), 3.67 (s, 2H), 3.56 (m, 2H), 2.54 (bm, 4H), 1.78 (bm, 4H), 0.92 (m, 2H), −0.04 (s, 9H).

Step 3:

Reaction of the product of Step 2 (31 mg, 0.063 mmol) with aqueous HCl/CH$_3$OH using the procedure of Example 2, Step 4, afforded the product (19 mg, 81%). $^1$H NMR (400 MHz, CD$_3$OD): δ 8.13 (s, 1H), 8.03 (m, 1H), 7.92 (s, 1H), 7.86 (m, 1H), 7.65 (s, 1H), 7.60–7.40 (m, 4H), 3.72 (s, 2H), 2.60 (m, 4H), 1.82 (m, 4H). MS (Cl) m/e 372 (M+H)$^+$.

Using appropriate starting materials and essentially the same procedure, the following compounds were prepared:

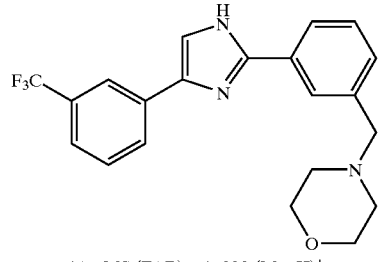

4A MS (FAB) m/e 388 (M + H)$^+$

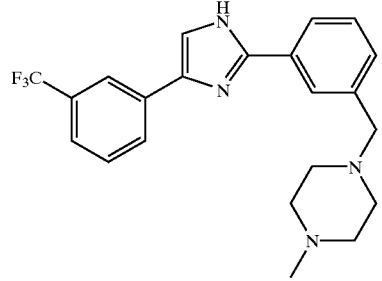

4B MS (FAB) m/e 401 (M + H)$^+$

Using appropriate amines, the following compounds were prepared from the product of Example 4, Step 1 by the procedure of Example 4, except that the order of the reductive amination and the cleavage of the (2-trimethylsilyl)-ethoxymethyl group (Steps 2 and 3) was reversed:

| Ex. | W | Data |
|---|---|---|
| 4C | —CH$_2$NH—⊲ | MS (Cl) 358 (M + H)$^+$ |
| 4D | —CH$_2$NHCH$_2$CH$_2$OH | MS FAB 362 (M + H)$^+$ |
| 4E | —CH$_2$NH(CH$_2$)$_2$N(CH$_3$)$_2$ | MS (Cl) 389 (M + H)$^+$ |
| 4F | —CH$_2$—N(piperazinyl)-C$_6$H$_4$-Cl | MS (FAB) 497 (M + H)$^+$ |
| 4G | —CH$_2$—N(piperidinyl with N-CH$_3$, CH$_3$) | MS (Cl) 429 (M + H)$^+$ |
| 4H | —CH$_2$NHCH$_2$-phenyl | MS (Cl) 408 (M + H)$^+$ |

-continued

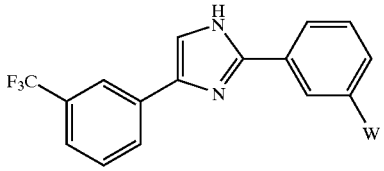

| Ex. | W | Data |
|---|---|---|
| 4I | 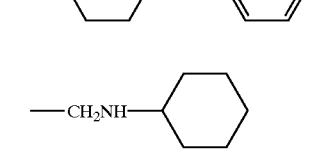 | MS (Cl) 476 (M + H)+ |
| 4J | —CH2NH—<cyclohexyl> | MS (FAB) 400 (M + H)+ |
| 4K | 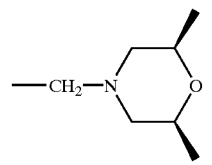 | MS (Cl) 416 (M + H)+ |
| 4L | 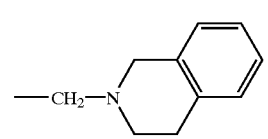 | MS (Cl) 434 (M + H)+ |
| 4M | 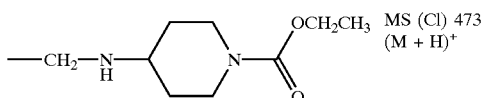 | MS (Cl) 473 (M + H)+ |
| 4N | 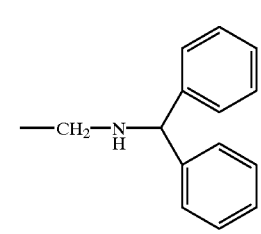 | MS (Cl) 484 (M + H)+ |

EXAMPLE 5

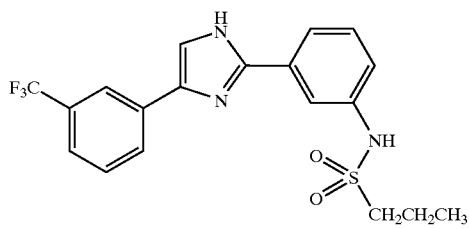

Step 1:

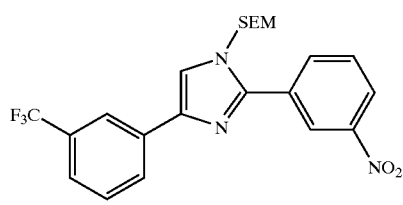

To a stirred, ice-cold solution of the product of Example 1 (3.70 g, 11.1 mmol) in THF (95 ml) was added NaH (0.32 g, 13 mmol). After 10 min., (2-trimethylsilyl)ethoxymethyl chloride (2.2 ml, 12 mmol) was added, and the reaction mixture was stirred at RT for 6 h. The reaction mixture was diluted with Et$_2$O, washed with H$_2$O and sat'd NaCl, dried (MgSO$_4$), filtered and evaporated. Flash chromatography (4:1 hexanes/EtOAc) afforded the product (4.08 g, 79%). $^1$H NMR (400 MHz, CDCl$_3$) δ 9.86 (1H, t, J=2.0 Hz), 8.35 (1H, m), 8.33 (1H, m), 8.14 (1H, m), 8.08 (1H, m), 7.72 (1H, t, J=8.0 Hz), 7.56 (3H, m), 5.38 (2H, s), 3.76 (2H, t, J=8.6 Hz), 1.08 (2H, t, J=8.6 Hz), 0.06 (9H, s). HRMS (FAB): Calcd. for C$_{22}$H$_{24}$N$_3$O$_3$F$_3$Si (M+H)$^+$: 464.1617. Found: 464.1629.

Step 2:

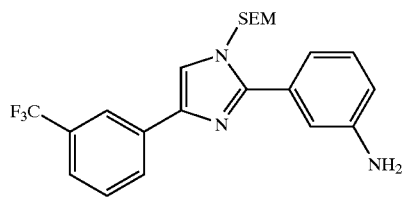

To a solution of the product of Step 1 (3.91 g, 8.40 mmol) in EtOH (100 ml) was added 10% Pd/C (0.4 g) and the mixture was purged with H$_2$. After 8 h under H$_2$ balloon pressure, the mixture was filtered through celite and the filter pad was washed with EtOH. The combined filtrate and washings were concentrated under vacuum to give the product (3.47 g, 95%) which was used in Step 3 without further purification. An analytical sample was isolated by PTLC (1:99 CH$_3$OH/CH$_2$Cl$_2$).

$^1$H NMR (400 MHz, CDCl$_3$) δ 8.15 (1H, s), 8.07 (1H, m), 7.53 (2H, m), 7.50 (1H, s), 7.29 (1H, m), 7.18 (2H, m), 6.81 (1H, m), 5.35 (2H, s), 3.63 (2H, t, J=8.2 Hz), 0.97 (2H, t, J=8.2 Hz), 0.04 (9H, s). MS (Cl) 434 (M+H)$^+$.

Step 3:

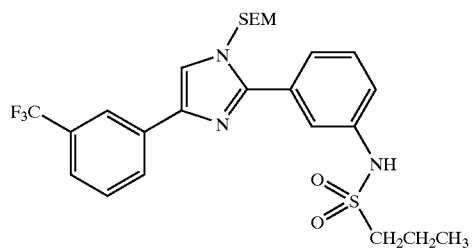

To solution of the product of Step 2 (123 mg, 0.29 mmol) in CH$_2$Cl$_2$ (5 ml) under N$_2$ was added pyridine (400 μl) and n-propylsulfonyl chloride (160 μl, 1.4 mmol). The reaction mixture was stirred at R.T. for 16 h, then partitioned between water and CH$_2$Cl$_2$. The organic layer was dried (K$_2$CO$_3$), filtered and concentrated. The residue was subjected to PTLC (2:98 CH$_3$OH/CH$_2$Cl$_2$) to afford the product (114 mg, 73%).

¹H NMR (400 MHz, CDCl₃) δ 8.15 (1H, s), 8.06 (1H, m), 7.78 (2H, m), 7.48–7.59 (3H, m), 7.41 (1H, m), 6.79 (1H, bs), 5.38 (2H, s), 3.69 (2H, t, J=8.2 Hz), 3.16 (2H, m), 1.92 (2H, m), 1.08 (3H, t, J=7.4 Hz), 1.02 (2H, t, J=8.2 Hz), 0.06 (9H, s). HRMS (FAB): Calcd. for C₂₅H₃₂N₃O₃SF₃Si (M+H)⁺: 540.1963 Found: 540.1937.

Step 4:

A mixture of the product of Step 3 (114 mg, 0.21 mmol), 5 N HCl (5 ml), and CH₃OH (5 ml) was refluxed for 3 h. The reaction mixture was allowed to cool, sat'd NaHCO₃ was cautiously added, and the whole was extracted with CH₂Cl₂. The organic layer was dried (MgSO₄), filtered, and evaporated. The residue was subjected to PTLC to afford the product (84 mg, 95%).

¹H NMR (400 MHz, CDCl₃) δ 8.07 (s, 1H), 7.96 (1H, d, J=7.3 Hz), 7.80 (1H, d, J=7.7 Hz), 7.76 (1H, m), 7.65–7.46 (3H, m), 7.38 (1H, t, J=7.9 Hz), 7.28 (1H, m), 3.15 (2H, m), 1.89 (2H, m), 1.03 (3H, t, J=7.4 Hz). HRMS (FAB): Calcd. for C₁₉H₁₈N₃O₂SF₃ (M+H)⁺: 410.1150 Found: 410.1160.

Using appropriate starting materials and essentially the same procedure, the following compounds were prepared:

| Ex. | W | Data |
|---|---|---|
| 5A | (CH3)SO2) | MS (FAB) 382 (M + H)⁺ |
| 5B | (CH3)SO2CH2CH3) | MS (FAB) 396 (M + H)⁺ |
| 5C | (CH3)SO2-C6H4-CF3) | MS (Cl) 512 (M + H)⁺ |
| 5D | (CH3)SO2CH2Ph) | MS (FAB) 458 (M + H)⁺ |
| 5E | (CH3)SO2CH(CH3)2) | MS (FAB) 410 (M + H)⁺ |
| 5F | (CH3)SO2Ph) | MS (FAB) 444 (M + H)⁺ |

EXAMPLE 6

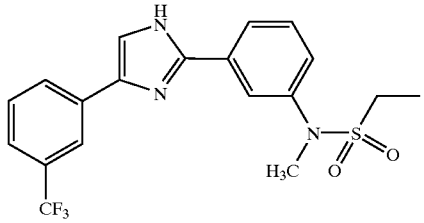

Step 1:

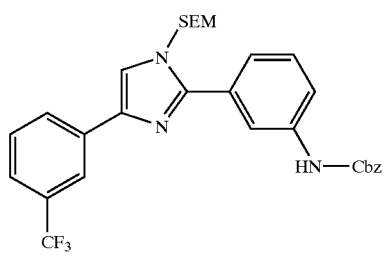

To a solution of the product of Example 5, Step 2 (581 mg, 1.34 mmol) and diisopropylamine (0.30 ml, 1.7 mmol) in CH₂Cl₂ (10 ml) at 0° C. was added benzyl chloroformate (0.22 ml, 1.5 mmol). The mixture was allowed to warm to R.T. and stirred for 60 h. The solution was diluted with CH₂Cl₂ (75 ml) and washed with 1 N HCl (25 ml) and 1 N NaOH (25 ml). The organic layer was dried (MgSO₄), filtered, and concentrated. Purification of the residue by column chromatograpy (CH₂Cl₂, then gradient of increasing concentration to 6:1000 CH₃OH/CH₂Cl₂ gave the product (732 mg, 96%). MS (ES) m/e 568 (M+H)⁺.

Step 2:

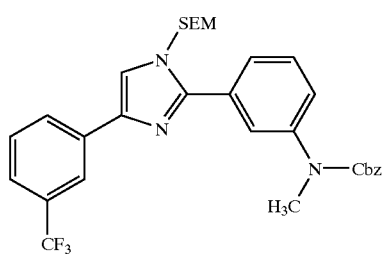

A mixture of the product of Step 1 (732 mg, 1.29 mmol) and 60% NaH in mineral oil (94 mg, 2.4 mmol) in anhydrous DMF (6 ml) was stirred for 1 h. CH₃I (0.15 ml, 2.4 mmol) was added and the stirring continued overnight. The mixture was diluted with CH₂Cl₂ (50 ml) and washed with water (2×40 ml). The organic layer was dried (MgSO₄), filtered, and concentrated. Purification of the residue by column chromatography (hexanes, then gradient of increasing concentration to 1:5 EtOAc/hexanes) afforded the product (723 mg, 97%). ¹H NMR (400 MHz, CDCl₃) δ 8.08 (s, 1H), 8.00 (m, 1H), 7.74 (s, 1H), 7.68 (d, 1H, J=8 Hz), 7.27–7.50 (m, 10H), 5.23 (s, 2H), 5.16 (s, 2H), 3.59 (t, 2H, J=8 Hz), 3.36 (s, 3H), 0.92 (t, 2H, J=8 Hz), −0.02 (s, 9H).

Step 3:

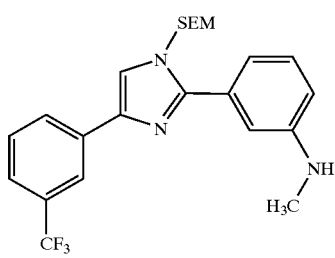

A mixture of the product of Step 2 (732 mg, 1.25 mmol) and 10% Pd/C (112 mg) in 200 proof EtOH (25 ml) was stirred under $H_2$ (1 atm) for 24 h. The mixture was filtered and the filtrate evaporated to dryness. Purification of the residue by column chromatography (hexanes, then gradient of increasing concentration to 1:9 EtOAc/hexanes) afforded the product (434 mg, 78%). $^1$H NMR (400 MHz, CDCl$_3$) δ 8.11 (s, 1H), 8.01 (m, 1H), 7.47 (m, 3H), 7.27 (m, 1H), 7.04 (m, 2H), 6.67 (m, 1H), 5.31 (s, 2H), 3.85 (b, 1H), 3.56 (t, 2H, J=8 Hz), 2.87 (s, 3H), 0.91 (t, 2H, J=8 Hz), −0.02 (s, 9H).

Step 4:

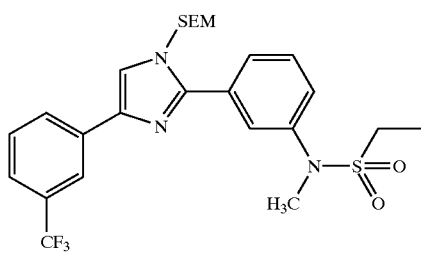

A solution of the product of Step 3 (49 mg, 0.11 mmol), CH$_3$CH$_2$SO$_2$Cl (78 mg, 0.61 mmol) and pyridine (0.24 ml, 3.0 mmol) in anhydrous CH$_2$Cl$_2$ (6 ml) was stirred for 7 days. The mixture was diluted with CH$_2$Cl$_2$ (45 ml) and washed with 1N NaOH (15 ml), water (20 ml) and saturated NH$_4$Cl (20 ml). The organic layer was dried (MgSO$_4$), filtered and concentrated. Purification of the residue by PTLC (1:99 CH$_3$OH/CH$_2$Cl$_2$) gave the product (51 mg, 86%). $^1$H NMR (400 MHz, CDCl$_3$) δ 8.11 (s, 1H), 8.02 (m, 1H), 7.88 (s, 1H), 7.80 (m, 1H), 7.50 (m, 5H), 5.32 (s, 2H), 3.66 (t, 2H, J=8 Hz), 3.41 (s, 3H), 3.09 (q, 2H, J=7.4 Hz), 1.39 (t, 3H, J=7.4 Hz), 0.97 (t, 2H, J=8 Hz), −0.01 (s, 9H).

Step 5:

A solution of the product of Step 4 (51 mg, 0.095 mmol) in CH$_3$OH (7 ml) and 5N HCl (5 ml) was heated to 90° C. for 4 h. After the mixture was cooled, it was partitioned between CH$_2$Cl$_2$ (50 ml) and aqueous NH$_4$OH (20 ml). The organic layer was dried (MgSO$_4$), filtered and concentrated. Purification of the residue by PTLC (1:66 CH$_3$OH/CH$_2$Cl$_2$) gave the product (38 mg, 98%). $^1$H NMR (400 MHz, CDCl$_3$) δ 8.02 (s, 1H), 7.91 (m, 2H), 7.72 (m,1H), 7.32–7.47 (m, 5H), 3.33 (s, 3H), 3.05 (q, 2H, J=7.4 Hz), 1.35 (t, 3H, J=7.4 Hz). MS (ES) m/e 410 (M+H)$^+$.

By using appropriate starting materials and essentially the same procedure, the following compounds were prepared:

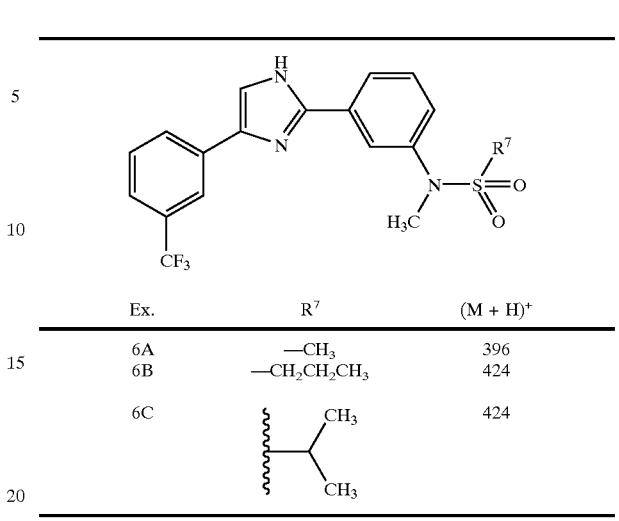

| Ex. | R$^7$ | (M + H)$^+$ |
|---|---|---|
| 6A | —CH$_3$ | 396 |
| 6B | —CH$_2$CH$_2$CH$_3$ | 424 |
| 6C | —CH(CH$_3$)$_2$ | 424 |

EXAMPLE 7

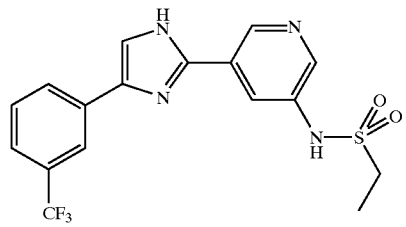

Step 1:

To a suspension of NH$_4$Cl (1.35 g, 25.2 mmol) in anhydrous toluene (15 ml) at 0° C. was added 2.0 M trimethylaluminum in toluene (12.6 ml, 25.2 mmol). After the addition was complete, the reaction mixture was allowed to warm to room temperature and stirred for 3 h. This reagent, CH$_3$Al(Cl)NH$_2$, was used directly in Step 2.

Step 2:

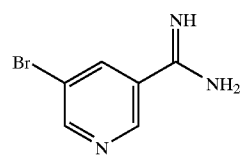

A mixture of the product of Step 1 (22.6 ml, 20.6 mmol) and 5-bromopyridine-3-carbonitrile (1.915 g, 10.46 mmol) in a sealed tube was heated to 95° C. overnight. The mixture was cooled and poured into a slurry of silica gel (40 g) in CHCl$_3$ (100 ml). This slurry was stirred for 1 h and the silica was filtered off. The filter cake was washed with CH$_3$OH (200 ml). Evaporation of the filtrate gave the product (2.65 g, 65%). $^1$H NMR (CD$_3$OD, 400 MHz): δ 9.00 (d, 1H, J=2.4 Hz), 8.91 (d, 1H, J=2 Hz), 8.45 (t, 1H, J=2.4 Hz). MS (Cl) m/e 200 (M+H)$^+$.

Step 3:

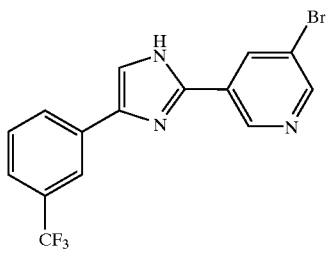

A mixture of the product of Step 2 (1.303 g, 6.6 mmol), Preparation 1 (1.199 g, 4.51 mmol), and Na$_2$CO$_3$ (1.15 g, 10.9 mmol) in acetone (20 ml) and DMF (20 ml) was refluxed for 5 h. The solvents were removed under vacuum and the residue was partitioned between water (50 ml) and CH$_2$Cl$_2$ (100 ml). The organic layer was washed with water (50 ml), dried (MgSO$_4$), filtered, and evaporated to dryness. The crude product was purified by column chromatography (gradient 0.5:99.5 CH$_3$OH/CH$_2$Cl$_2$ to 1.5:98.5 CH$_3$OH/CH$_2$Cl$_2$) to give a light-yellow solid (0.705 g, 42%). $^1$H NMR (CD$_3$OD, 400 MHz): 69.10 (d, 1H, J=1.6 Hz), 8.66 (d, 1H, J=2 Hz), 8.57 (t, 1H, J=2 Hz), 8.14 (s, 1H), 8.06 (d, 1H, J=6.8 Hz), 7.75 (s, 1H), 7.57 (m, 2H). MS (Cl) m/e 368 (M+H)$^+$.

Step 4:

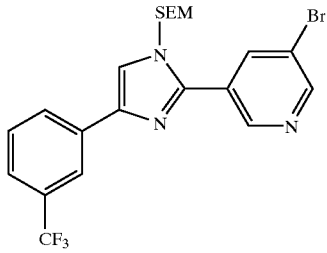

Using the procedure of Example 5, Step 1, reaction of the product of Step 3 (311 mg, 0.845 mmol) with NaH (60% disp., 43 mg, 1.1 mmol) and (2-trimethylsilyl)ethoxymethyl chloride (0.21 ml, 1.07 mmol) afforded the product (292 mg, 69%). $^1$H NMR (CDCl$_3$, 400 MHz): δ 9.05 (d, 1H, J=2 Hz), 8.74 (d, 1H, J=2 Hz), 8.42 (t, 1H, J=2 Hz), 8.08 (s, 1H), 8.01 (m, 1H), 7.51 (m, 3H), 5.31 (s, 2H), 3.68 (t, 2H, J=8 Hz), 0.99 (t, 2H, J=8 Hz), 0.02 (s, 9H).

Step 5:

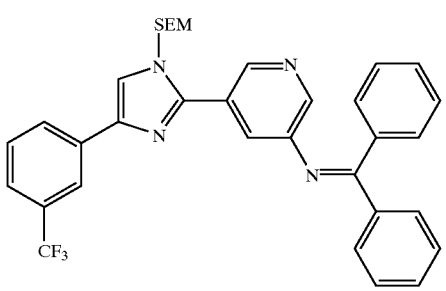

A mixture of the product of Step 4 (114 mg, 0.229 mmol), benzophenone imine (52 mg, 0.29 mmol), sodium t-butoxide (35 mg, 0.36 mmol), (R)-(+)-2,2'-bis(diphenylphosphino)-1,1'-binaphthyl (13 mg, 0.02 mmol), and tris(dibenzylideneacetone)dipalladium(0) (8 mg, 0.009 mmol) in anhydrous toluene (3 ml) was purged with N$_2$ for 5 min. The mixture was heated to 80° C. in a sealed tube for 18 h. The mixture was cooled, diluted with Et$_2$O (20 ml) and CH$_2$Cl$_2$ (20 ml), and filtered. After evaporation of the filtrate, the crude product was purified by PTLC (1.5:98.5 CH$_3$OH/CH$_2$Cl$_2$) to give an oil (127 mg, 93%). $^1$H NMR (CDCl$_3$, 400 MHz): δ 8.67 (s, 1H), 8.13 (d, 1H, J=1.6 Hz), 8.06 (s, 1H), 7.97 (m, 1H), 7.77 (m, 2H), 7.5–7.2 (m, 10H), 7.15 (m, 2H), 5.06 (s, 2H), 3.52 (t, 2H, J=8 Hz), 0.90 (t, 2H, J=8 Hz), 0.03 (s, 9H).

Step 6:

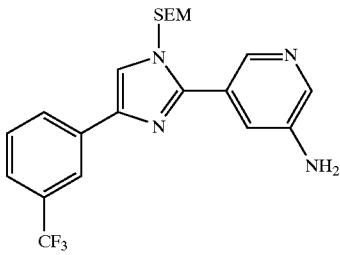

A solution of the product of Step 5 (127.4 mg, 0.213 mmol), sodium acetate (43 mg, 0.52 mmol), and H$_2$NOH.HCl (29 mg, 0.42 mmol) in CH$_3$OH (3 ml) was stirred for 40 min. The solution was partitioned between 0.1 M aqueous NaOH (30 ml) and CH$_2$Cl$_2$ (50 ml). The organic layer was dried (MgSO$_4$), filtered and evaporated to dryness. PTLC (2:98 CH$_3$OH/CH$_2$Cl$_2$) gave a solid (82 mg, 89%).

$^1$H NMR (CDCl$_3$, 400 MHz): δ 8.43 (d, 1H, J=2 Hz), 8.16 (d, 1H, J=2.8 Hz), 8.09 (s, 1H), 8.00 (m, 1H), 7.49 (m, 4H), 5.32 (s, 2H), 3.87 (bs, 2H), 3.62 (t, 2H, J=8 Hz), 0.95 (t, 2H, J=8 Hz), 0.00 (s, 9H).

Step 7:

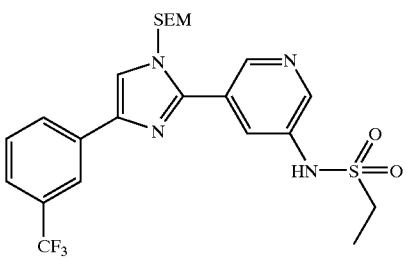

A solution of the product of Step 6 (37 mg, 0.085 mmol), ethane-sulfonyl chloride (13 mg, 0.10 mmol), and pyridine (0.1 ml, 1.2 mmol) in anhydrous CH$_2$Cl$_2$ (5 ml) was stirred overnight. The reaction mixture was diluted with CH$_2$Cl$_2$ (40 ml) and washed with water (20 ml). The organic layer was dried (MgSO$_4$) and evaporated to dryness. PTLC (5:95 CH$_3$OH/CH$_2$Cl$_2$) gave an oil (28 mg, 63%). $^1$H NMR (CDCl$_3$, 400 MHz): δ 8.89 (bs, 1H), 8.53 (bs, 1H), 8.14 (s, 1H), 8.05 (s, 1H), 7.99 (m, 2H), 7.48 (m, 3H), 5.30 (s, 2H), 3.64 (t, 2H, J=8.4 Hz), 3.20 (q, 2H, J=7.2 Hz), 1.39 (t, 3H, J=7.2 Hz), 0.97(t, 2H, J=8.4 Hz), 0.02 (s, 9H).

Step 8:

Reaction of the product of Step 7 (28 mg, 0.053 mmol) with 5 N aqueous HCl by the procedure of Example 5, Step 4, gave the product (10.5 mg, 49%). $^1$H NMR (CD$_3$OD, 400 MHz): δ 8.70 (bs, 1H), 8.43 (bs, 1H), 8.00 (t, 1H, J=2 Hz), 7.94 (s, 1H), 7.86 (m, 1H), 7.45 (m, 2H), 7.40 (s, 1H), 3.10 (q, 2H, J=7.2 Hz), 1.31 (t, 3H, J=7.2 Hz). MS (Cl) m/e 397 (M+H)$^+$.

Using appropriate starting materials and essentially the same procedure, the following compounds were prepared:

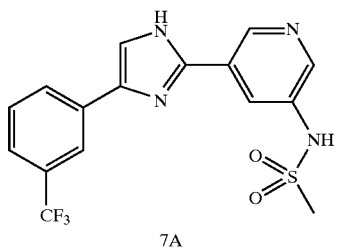

7A

¹H NMR (CD₃OD, 400 MHz): δ 8.90 (bs, 1H), 8.45 (bs, 1H), 8.29 (s, 1H), 8.15 (s, 1H), 8.07 (d, 1H, J=7.6 z), (bs, 1H, 7.6 (m, 2H), 3.13 (s, 3H). MS (ES) m/e 383.1 (M+H)⁺.

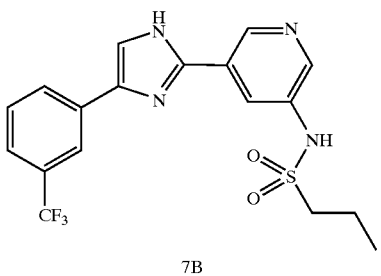

7B

1H NMR (CD₃OD, 400 MHz): δ 8.84 (bs, 1H), 8.42 (bs, 1H), 8.26 (m, 1H), 8.14 (s, 1H), 8.05 (d, 1H, J=6.4 Hz), 7.75 (bs, 1H), 7.59 (m, 2H), 3.23 (m, 2H), 1.86 (m, 2H), 1.05 (t, 3H, J=7.2 Hz). MS (ES) m/e 411.1 (M+H)⁺.

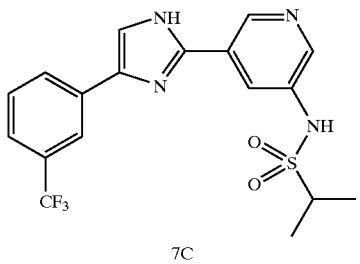

7C

¹H NMR (CD₃OD, 400 MHz): δ 8.83 (bs, 1H), 8.45 (bs, 1H), 8.28 (m, 1H), 8.14 (s, 1H), 8.06 (d, 1H, J=7.6 Hz), 7.75 (bs, 1H), 7.59 (m, 2H), 3.43 (sept, 1H, J=6.8 Hz), 1.40 (d, 6H, J=6.8 Hz). MS (ES) m/e 411.1 (M+H)⁺.

EXAMPLE 8

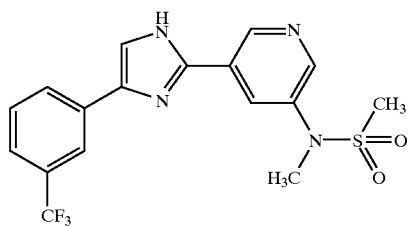

Step 1:

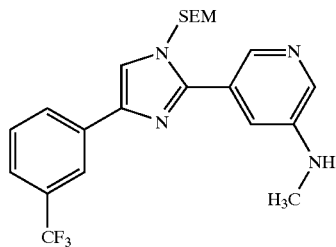

A mixture of the product of Example 7, Step 4 (146 mg, 0.29 mmol), palladium acetate (16 mg, 0.07 mmol), (S)-(−)-2,2'-bis(diphenylphosphino)-1,1'-binaphthyl (67 mg, 0.11 mmol), and Cs₂CO₃ (320 mg, 0.98 mmol) in toluene (3 ml) was purged with N₂ for 10 min. CH₃NH₂ (2 M in THF, 4 ml) was added, and the reaction mixture was heated at 80° C. in a sealed tube for 16 h. The reaction mixture was allowed to cool, diluted with CH₂Cl₂ (60 ml), and filtered. The filtrate was washed with H₂O (20 ml), dried (MgSO₄), filtered and concentrated. The residue was subjected to PTLC (5:95 CH₃OH/CH₂Cl₂) to give the product (47 mg, 36%). ¹H NMR (CDCl₃, 400 MHz): δ 8.33 (1H, s), 8.10 (2H, m), 8.00 (1H, m), 7.48 (3H, m), 7.36 (1H, s), 5.31 (2H, s), 4.11 (1H, bs), 3.59 (2H, t, J=8 Hz), 2.91 (3H, s), 0.93 (2H, t, J=8 Hz), −0.02 (9H, s).

Step 2:

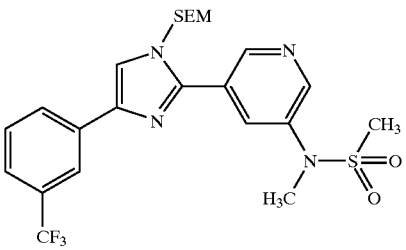

A mixture of the product of Step 1 (16 mg, 0.04 mmol), CH₃SO₂Cl (24 mg, 0.21 mmol), and pyridine (0.07 ml, 0.9 mmol) in CH₂Cl₂ (2.5 ml) was stirred for 4 days. The reaction mixture was diluted with CH₂Cl₂ (30 ml), washed with 1 N NaOH (10 ml) and H₂O (20 ml), dried (MgSO₄), filtered and concentrated. PTLC of the residue (5:95 CH₃OH/CH₂Cl₂) gave the product (16 mg, 75%).

¹H NMR (CDCl₃, 400 MHz): δ 9.04 (1H, s), 8.72 (1H, s), 8.27 (1H, m), 8.08 (1H, s), 8.02 (1H, m), 7.52 (3H, m), 5.32 (2H, s), 3.68 (2H, t, J=8 Hz), 3.42 (3H, s), 2.93 (3H, s), 0.98 (2H, t, J=8 Hz), 0.00 (9H, s).

Step 3:

Reaction of the product of Step 2 (16 mg, 0.03 mmol) with 5N HCl by the procedure of Example 5, Step 4 gave the product (11 mg, 93%).

¹H NMR (CD₃OD, 400 MHz): δ 9.02 (1H, s), 8.65 (1H, m), 8.45 (1H, m), 8.15 (1H, s), 8.06 (1H, d, J=8 Hz), 7.77 (1H, s), 7.57 (2H, m), 3.43 (3H, s), 3.02 (3H, s). MS (ES) m/e 397 (M+H)⁺.

EXAMPLE 9

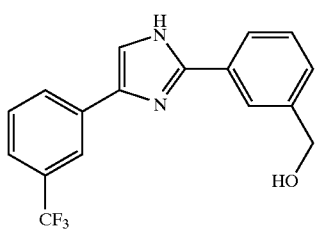

THF (1.8 ml) was added to LAH (2.5 mg, 0.066 mmol) under $N_2$ at 0° C. The product of Example 1B (20 mg, 0.058 mmol) was dissolved in THF (1.4 ml) and added dropwise over 5 min. to the LAH/THF slurry. After 0.5 h, more LAH (3.8 mg, 0.10 mmol) was added and the reaction was stirred at 0° C. for 1.25 h. 10% NaOH (0.1 ml) and EtOAc (2.0 ml) was added to the reaction, followed by $MgSO_4$. The mixture was stirred, filtered and concentrated under vacuum to give the product (16 mg, 88%) as a white solid. $^1$H NMR ($CD_3OD$, 400 MHz): δ 8.15 (bs, 1H), 8.05 (m, 1H), 7.96 (s, 1H), 7.86 (m, 1H), 7.72–7.39 (m, 5H), 4.70 (s, 2H). HRMS (FAB): Calcd for $C_{17}H_{13}N_2OF_3$ $(M+H)^+$: 319.1058. Found: 319.1059.

EXAMPLE 10

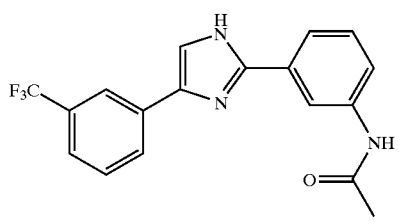

Step 1:

A solution of the product of Example 5, Step 2 (68 mg, 0.16 mmol), acetic anhydride (26 μl, 0.28 mmol) and pyridine (0.13 ml, 1.55 mmol) in $CH_2Cl_2$ (4 ml) was stirred for 3 days. The reaction mixture was diluted with $CH_2Cl_2$ (40 ml) and washed with aq. $NH_4Cl$ (2×20 ml). The organic layer was dried ($MgSO_4$), filtered and evaporated. Purification of the residue by PTLC (3:97 $CH_3OH/CH_2Cl_2$) gave the product (62 mg, 84%).

$^1$H NMR (400 MHz, $CDCl_3$): δ 8.09 (s, 1H), 8.00 (m, 2H), 7.85 (s, 1H), 7.77 (m, 1H), 7.49 (m, 3H), 7.40 (m, 1H), 5.33 (s, 2H), 3.61 (t, 2H, J=8 Hz), 2.65 (bs, 1H), 2.11 (s, 3H), 0.94 (t, 2H, J=8 Hz), 0.01 (s, 9H).

Step 2:

The product of Step 1 (62 mg, 0.13 mmol) and 1.0M TBAF in THF (3.0 ml, 3.0 mmol) was stirred at R.T. until no starting material remained. The reaction mixture was diluted with $CH_2Cl_2$ and washed with water several times, dried ($K_2CO_3$), filtered and evaporated. PTLC (2:98 $CH_3OH/CH_2Cl_2$) gave the product (37 mg, 78%). $^1$H NMR (400 MHz, $CDCl_3$): δ 8.01 (s, 1H), 7.98 (s, 1H), 7.89 (s, 1H), 7.85 (d, 1H, J=7.2 Hz), 7.55 (d, 1H, J=8.0 Hz), 7.42 (m, 2H), 7.32 (s, 1H), 7.29 (d, 1H, J=8.4 Hz), 7.19 (t, 1H, J=7.6 Hz), 2.10 (s, 3H). MS (FAB) m/e 364 $(M+H)^+$.

Using appropriate starting materials and essentially the same procedure, the following compounds were prepared:

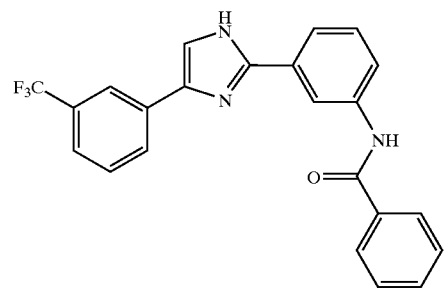

10A MS (Cl) m/e 408 $(M + H)^+$.

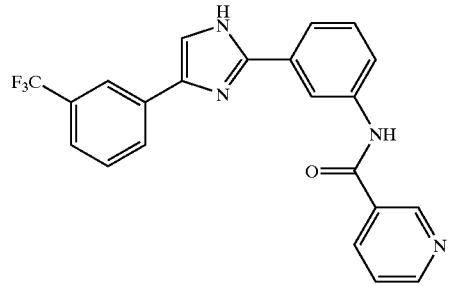

10B MS (Cl) m/e 409 $(M + H)^+$.

EXAMPLE 11

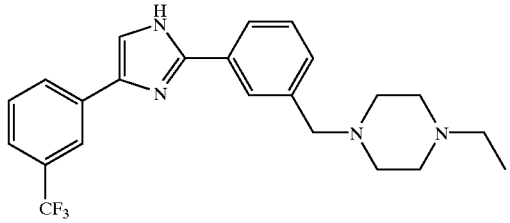

Step 1:

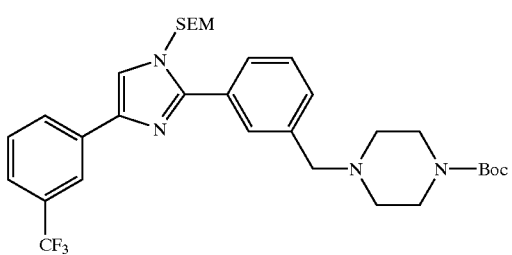

A mixture of the product of Example 4, Step 1 (759 mg, 1.70 mmol), tert-butyl 1-piperazine carboxylate (356 mg, 1.91 mmol), and sodium triacetoxyborohydride (565 mg, 2.67 mmol) in dichloroethane (9 ml) was stirred at R.T. overnight. The mixture was diluted with $CH_2Cl_2$ (100 ml) and washed with 1N aqueous NaOH (20 ml). The organic layer was dried ($MgSO_4$), filtered, and evaporated. Purification of the residue by flash chromatography (gradient; $CH_2Cl_2$ to 1.5:98.5 $CH_3OH/CH_2Cl_2$) afforded the product (902 mg, 86%). $^1$H NMR (400 MHz, $CDCl_3$) δ 8.09 (1H, s), 8.00 (1H, m), 7.76 (1H, bs), 7.69 (1H, m), 7.23–7.48 (5H, m), 5.29 (2H, s), 3.58 (4H, m), 3.42 (4H, bm), 2.40 (4H, bm), 1.43 (9H, s), 0.92 (2H, t, J=8 Hz), −0.02 (9H, s). MS m/e 617 $(M+H)^+$.

Step 2:

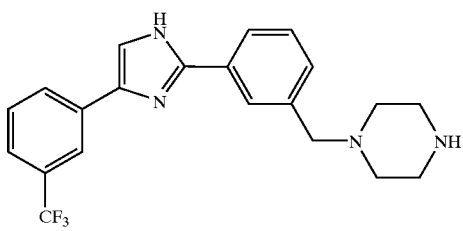

A solution of the product of Step 1 (701 mg, 1.14 mmol) in CH$_3$OH (5 ml) and 5N aqueous HCl (10 ml) was refluxed for 8 h. The reaction mixture was allowed to cool, then partitioned between CH$_2$Cl$_2$ (60 ml) and aqueous NH$_4$OH (20 ml). The aqueous layer was extracted with CH$_2$Cl$_2$ (40 ml) and the combined organic layers were dried (MgSO$_4$), filtered and evaporated. Purification of the residue by flash chromatography (gradient; 5:95 to 8:92 2.0 M NH$_3$ in CH$_3$OH/CH$_2$Cl$_2$) afforded the product (451 mg, 100%). $^1$H NMR (400 MHz, CD$_3$OD) δ 8.14 (1H, s), 8.04 (1H, d, J=7.6 Hz), 7.94 (1H, s), 7.86 (1H, d, J=7.6 Hz), 7.66 (1H, s), 7.57 (2H, m), 7.44 (2H, m), 3.61 (2H, s), 2.87 (4H, t, J=5 Hz), 2.51 (4H, bm). MS m/e 387 (M+H)$^+$.

Step 3:

A mixture of the product of Step 2 (12 mg, 0.031 mmol), 1.0 M acetaldehyde in dichloroethane (33 μL, 0.033 mmol), and sodium triacetoxyborohydride (15 mg, 0.071 mmol) in dichloroethane (2 ml) was stirred overnight. The mixture was evaporated to dryness and the residue was purified by PTLC (5:95 2M NH$_3$ in CH$_3$OH/CH$_2$Cl$_2$) to give the product (8.4 mg, 65%). $^1$H NMR (400 MHz, CD$_3$OD) δ 8.14 (1H, s), 8.04 (1H, d, J=7.6 Hz), 7.93 (1H, s), 7.86 (1H, d, J=7.6 Hz), 7.65 (1H, bs), 7.56 (2H, m), 7.44 (2H, m), 3.62 (2H, s), 2.57 (8H, bm), 2.46 (2H, q, J=7.6 Hz), 1.09 (3H, t, J=7.6 Hz). MS m/e 415 (M+H)$^+$.

By using appropriate starting materials and essentially the same procedure, the following compounds were prepared:

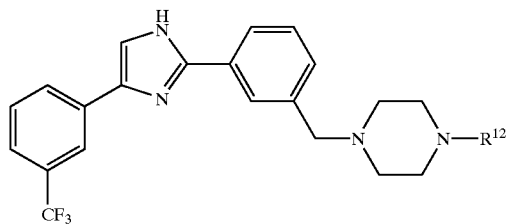

wherein R$^{12}$ is as defined in the following table:

| Ex. | R$^{12}$ | (M + H)$^+$ |
|---|---|---|
| 11A | (isopropyl) | 429 |
| 11B | (cyclopentylmethyl) | 455 |
| 11C | (cyclohexylmethyl) | 469 |
| 11D | (tetrahydropyran-4-ylmethyl) | 471 |
| 11E | (cyclohexylethyl) | 483 |
| 11F | (benzyl-ethyl) | 477 |
| 11G | (pyridin-4-ylethyl) | 478 |

EXAMPLE 12

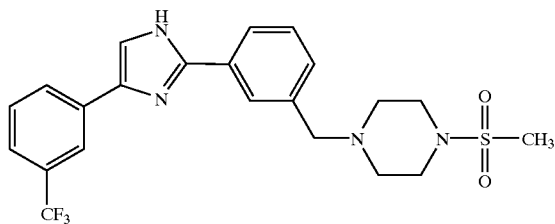

A solution of the product of Example 11, Step 2 (15 mg, 0.039 mmol), CH$_3$SO$_2$Cl (5 mg, 0.04 mmol), and pyridine (6 mg, 0.08 mmol) in CH$_2$Cl$_2$ (2.5 ml) was stirred overnight. The mixture was diluted with CH$_2$Cl$_2$ (30 ml) and washed with aqueous 1N NaOH (10 ml). The organic layer was dried (MgSO$_4$), filtered, and evaporated. Purification of the residue by TLC (5:95 2M NH$_3$ in CH$_3$OH/CH$_2$Cl$_2$) gave the product (14 mg, 79%). $^1$H NMR (400 MHz, CD$_3$OD) δ 8.14 (1H, s), 8.04 (1H, d, J=7.2 Hz), 7.96 (1H, s), 7.85 (1H, d, J=7.2 Hz), 7.66 (1H, s), 7.56 (2H, m), 7.43 (2H, m), 3.66 (2H, s), 3.25 (4H, m), 2.83 (3H, s), 2.61 (4H, m). MS m/e 465 (M+H)$^+$.

By using the appropriate sulfonyl chloride and essentially the same procedure as described in Example 12, the following compounds were prepared:

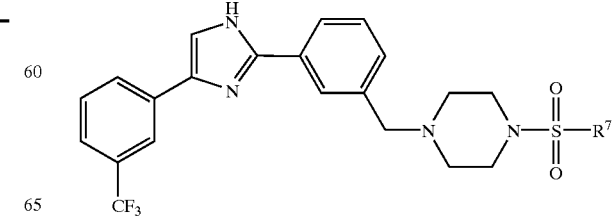

wherein R[7] is as defined in the following table:

| Ex. | R[7] | (M + H)+ |
|---|---|---|
| 12A |  | 479 |
| 12B |  | 493 |
| 12C | 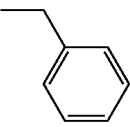 | 541 |
| 12D | 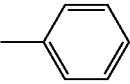 | 527 |
| 12E | 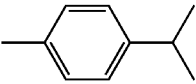 | 569 |

EXAMPLE 13

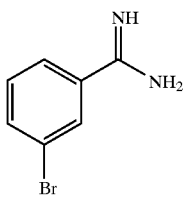

Step 1:

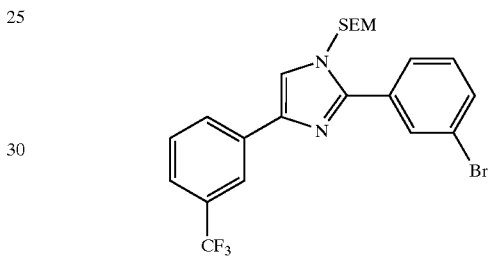

To a stirred, ice-cold solution of 3-bromobenzonitrile (6.0 g, 33 mmol) in THF (20 ml) was added a solution of lithium bistrimethylsilylamide in THF (1.0 M; 34.5 ml, 34.5 mmol). The reaction mixture was allowed to attain R.T., stirred for 16 h, then evaporated to dryness. The residue was partitioned between 9:1 CHCl$_3$/CH$_3$OH (50 ml) and 10% NaOH (50 ml). The organic layer was dried (MgSO$_4$), filtered and concentrated to give the product (7.2 g). $^1$H NMR (400 MHz, CD$_3$OD) δ 7.92 (1H, t, J=2 Hz), 7.72 (2H, m), 7.40 (1H, t, J=8 Hz).

Step 2:

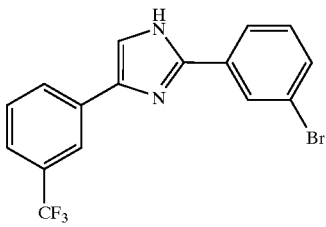

A mixture of Preparation 1 (3.8 g, 14 mmol), the product of Step 1 (7.2 g), and Na$_2$CO$_3$ (2.96 g, 27.9 mmol) in DMF (60 ml) was stirred for 16 h. The reaction mixture was concentrated, the residue was taken up in CH$_2$Cl$_2$ (150 ml), and washed with water (3×100 ml). The organic layer was dried (MgSO$_4$), filtered, and evaporated. The residue was subjected to flash chromatography (3:2 EtOAc/hexanes) to give the product as a solid (4.74 g, 91%).

1H NMR (400 MHz, CDCl$_3$) δ 9.75 (1H, bs), 8.00 (1H, s), 7.93 (2H, m), 7.71 (1H, d, J=8 Hz), 7.43 (4H, m), 7.19 (1H, t, J=8 Hz).

Step 3:

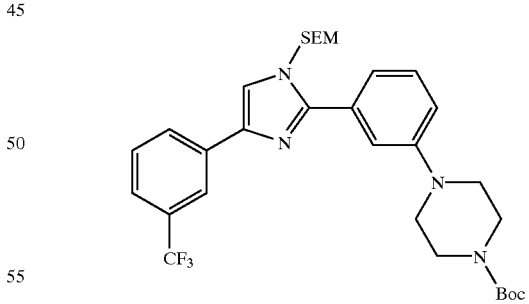

By using the procedure of Preparation 2, Step 2, the product of Step 2 (4.74 g, 12.9 mmol) was reacted with (2-trimethylsilyl)ethoxymethyl chloride (2.7 ml, 15 mmol) to give the product (5.31 g, 82%).

$^1$H NMR (400 MHz, CDCl$_3$) δ 8.07 (1H, s), 8.02 (2H, m), 7.79 (1H, d, J=7.2 Hz), 7.58 (1H, d, J=8.8 Hz), 7.48 (3H, m), 7.35 (1H, t, J=7.8 Hz), 5.29 (2H, s), 3.63 (2H, t, J=8.3 Hz), 0.96 (2H, t, J=8.3 Hz), −0.01 (9H, s). MS m/e 499 (M+H)+.

Step 4:

A mixture of the product of Step 3 (1.275 g, 2.56 mmol), palladium acetate (63 mg, 0.28 mmol), (S)-(−)-2,2'-bis (diphenylphosphino)-1,1'-binaphthyl (328 mg, 0.52 mmol), (N-tert-butoxycarbonyl)piperazine (1.025 g, 5.503 mmol), and Cs$_2$CO$_3$ (2.53 g, 7.75 mmol) in toluene (35 ml) was purged with N$_2$ for 10 min, then heated at 80° C. for 16 h. The reaction mixture was allowed to cool, solids were removed by filtration, and the filtrate was concentrated. The residue was partitioned between H$_2$O (50 ml) and CH$_2$Cl$_2$ (100 ml), and the organic layer was dried (MgSO$_4$), filtered and concentrated. The residue was subjected to flash chromatography (1:9 EtOAc/hexanes) to give the product (1.07 g, 69%).

$^1$H NMR (400 MHz, CDCl$_3$) δ 8.10 (1H, s), 8.02 (1H, bs), 7.47 (3H, m), 7.35 (2H, m), 7.26 (1H, m), 7.00 (1H, m), 5.30 (2H, s), 3.57 (6H, m), 3.20 (4H, m), 1.46 (9H, s), 0.92 (2H, m), −0.03 (9H, s). MS m/e 603 (M+H)$^+$.

Step 5:

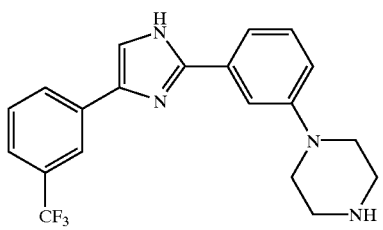

Reaction of the product of Step 4 (1.07 g, 1.78 mmol) with 5 N HCl by the procedure of Example 11, Step 2 gave the product (584 mg, 88%).

$^1$H NMR (400 MHz, CD$_3$OD) δ 8.12 (1H, s), 8.03 (1H, d, J=7.6 Hz), 7.63 (1H, s), 7.56 (3H, m), 7.40 (1H, m), 7.34 (1H, t, J=7.8 Hz), 7.01 (1H, m), 3.23 (4H, m), 3.00 (4H, m). MS m/e 373 (M+H)$^+$.

Step 6:

Reaction of the product of Step 5 (10 mg, 0.027 mmol) with acetaldehyde by the procedure of Example 11, Step 3 gave the product (6.6 mg, 61%). $^1$H NMR (400 MHz, CD$_3$OD) δ 8.13 (1H, s), 8.03 (1H, d, J=7.6 Hz), 7.58 (4H, m), 7.40 (1H, m), 7.35 (1H, t, J=7.8 Hz), 7.03 (1H, m), 3.33 (4H, m), 2.70 (4H, m), 2.53 (2H, q, J=7.2 Hz), 1.17 (3H, t, J=7.2 Hz). MS m/e 401 (M+H)$^+$.

Using a similar procedure, the following compounds were prepared:

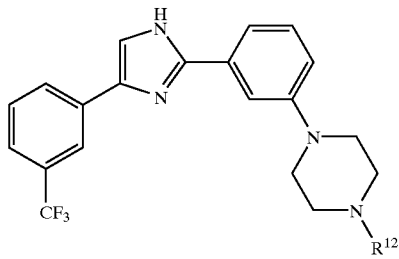

wherein R$^{12}$ is as defined in the table

| Ex | R$^{12}$ | (M + H)$^+$ |
|---|---|---|
| 13A | —CH$_3$ | 387 |
| 13B | isopropyl | 415 |
| 13C | n-propyl | 415 |
| 13D | cyclohexyl | 455 |
| 13E | isobutyl | 429 |
| 13F | cyclohexylmethyl | 469 |
| 13G | benzyl | 463 |
| 13H | 3-pyridylmethyl | 464 |

EXAMPLE 14

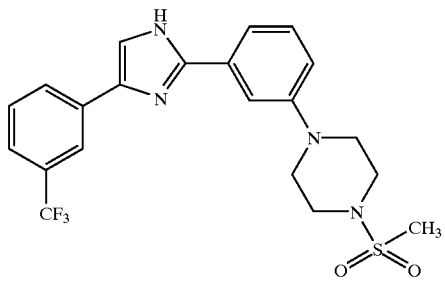

Reaction of the product of Example 13, Step 5 (15 mg, 0.040 mmol) with CH$_3$SO$_2$Cl (7.2 mg, 0.063 mmol) by the procedure of Example 12 afforded the product (15.4 mg, 85%). $^1$H NMR (400 MHz, CDCl$_3$) δ 8.02 (1H, s), 7.95 (1H, m), 7.57 (1H, s), 7.48 (2H, m), 7.41 (1H, s), 7.34 (1H, m), 7.27 (1H, m), 6.87 (1H, m), 3.27 (8H, m), 2.77 (3H, s). MS m/e 451 (M+H)$^+$.

By using the appropriate sulfonyl chloride and essentially the same procedure, the following compounds were prepared:

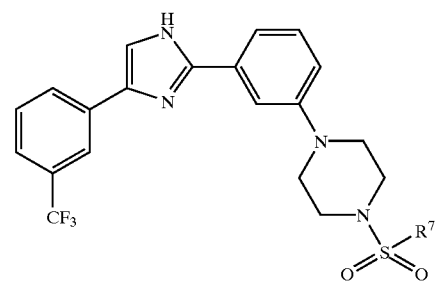

wherein $R^7$ is as defined in the following table:

| Ex. | $R^7$ | $(M + H)^+$ |
|---|---|---|
| 14A | (ethyl) | 465 |
| 14B | (propyl) | 479 |
| 14C | (isopropyl) | 479 |
| 14D | (benzyl) | 527 |
| 14E | (tolyl) | 513 |

EXAMPLE 15

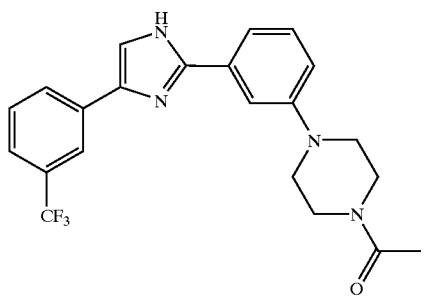

A solution of the product of Example 13, Step 5 (12 mg, 0.032 mmol), acetic anhydride (3.6 mg, 0.035 mmol), and triethylamine (3.4 mg, 0.034 mmol) in $CH_2Cl_2$ (1.5 ml) was stirred overnight. Purification by TLC (1:20 $CH_3OH/CH_2Cl_2$) gave the product (13.4 mg, 100%).

$^1H$ NMR (400 MHz, $CDCl_3$) δ 8.04 (1H, s), 7.97 (1H, m), 7.60 (1H, s), 7.47 (3H, m), 7.43 (1H, s), 7.28 (1H, t, J=8 Hz), 6.89 (1H, m), 3.73 (2H, t, J=5.2 Hz), 3.57 (2H, t, J=5 Hz), 3.19 (2H, t, J=5.2 Hz), 3.11 (2H, t, J=5 Hz), 2.08 (3H, s). MS m/e 415 $(M+H)^+$.

By using the appropriate acid chloride and essentially the same procedure, the following compounds were prepared:

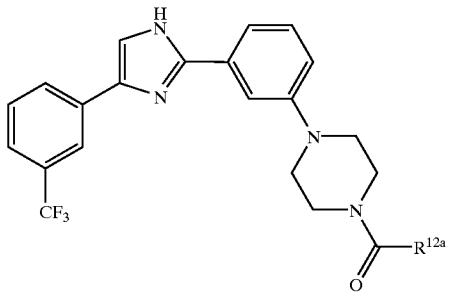

wherein $R^{12a}$ is as defined in the following table:

| Ex. | $R^{12a}$ | $(M + H)^+$ |
|---|---|---|
| 15A | (ethyl) | 429 |
| 15B | (propyl) | 443 |
| 15C | (isopropyl) | 443 |
| 15D | (isobutyl) | 457 |
| 15E | (cyclopropyl) | 441 |
| 15F | (cyclohexylmethyl) | 483 |
| 15G | (benzyl) | 491 |
| 15H | (tolyl) | 477 |
| 15I | (methylpyridyl) | 478 |

EXAMPLE 16

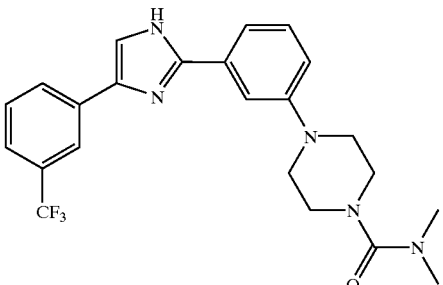

A solution of the product of Example 13, Step 5 (12 mg, 0.032 mmol), 1.0 M dimethylcarbamyl chloride in dichloroethane (0.04 ml, 0.04 mmol), and triethylamine (5 mg, 0.05 mmol) in $CH_2Cl_2$ (1.5 ml) was stirred overnight. Purification by TLC (1:20 $CH_3OH/CH_2Cl_2$) gave the product (10.6 mg, 75%). $^1H$ NMR (400 MHz, $CDCl_3$) δ 8.03 (1H, s), 7.93 (1H, m), 7.52 (1H, s), 7.44 (2H, m), 7.41 (1H, s), 7.37 (1H, d, J=7.6 Hz), 7.24 (1H t, J=7.2 Hz), 6.83 (1H, m), 3.28 (4H, m), 3.06 (4H, m), 2.80 (6H, s). MS m/e 444 $(M+H)^+$.

By using the appropriate carbamyl chloride and essentially the same procedure as described in Example 16, the following compounds were prepared:

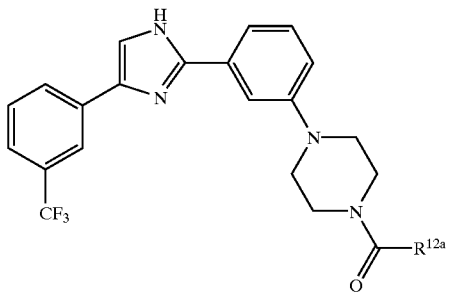

wherein $R^{12a}$ is as defined in the following table:

| Ex. | $R^{12a}$ | $(M + H)^+$ |
|---|---|---|
| 16A | | 500 |
| 16B | | 472 |

EXAMPLE 17

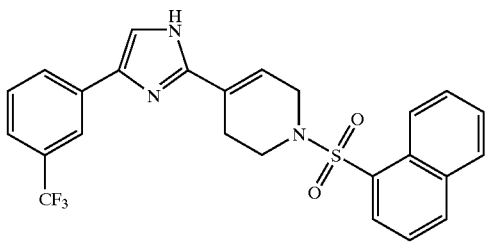

Step 1:

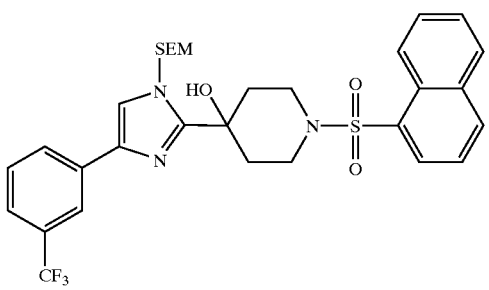

A solution of Preparation 2, Step 2 (0.18 g, 0.51 mmol) in THF (5 ml) under $N_2$ was cooled to −78° C. and n-BuLi (0.48 ml, 0.77 mmol) was added dropwise. The reaction was stirred for 10 min., then N-tert-butoxycarbonyl-4-piperidone (0.11 g, 0.56 mmol) in THF (2 ml) was added dropwise. After stirring for 2.5 h, the reaction was quenched with water, extracted with EtOAc, dried over $K_2CO_3$, filtered and concentrated under vacuum to give a residue (0.28 g, 100%) which was used in the next reaction without further purification.

To solution of the residue (0.28 g, 0.51 mmol) in $CH_2Cl_2$ (7 ml) under $N_2$ was added TFA (0.6 ml). After stirring at R.T. for 40 min., the reaction was washed with water, treated with 1 N NaOH, extracted with $CH_2Cl_2$, dried over $K_2CO_3$, filtered and concentrated under vacuum to give the residue (0.19 g, 80%) which was used in the next reaction without further purification.

The residue (0.13 g, 0.29 mmol) was dissolved in $CH_2Cl_2$ (3 ml) under $N_2$ and $Et_3N$ (80 µL, 0.58 mmol) was added, followed by the dropwise addition of 1-naphthalenesulfonyl chloride (0.079 g, 0.34 mmol) in $CH_2Cl_2$ (1 ml). After stirring at R.T. for 18 h, the reaction was treated with 1 N NaOH, extracted with $CH_2Cl_2$, dried over $K_2CO_3$, filtered and concentrated under vacuum. Purification via PTLC (40:60 EtOAc/hexanes) yielded the product (0.15 g, 84%). MS (Cl) m/e 632 (M+H)$^+$.

Step 2:

To solution of the product of Step 1 (0.15 g, 0.24 mmol) in $CH_3OH$ (4.5 ml) under $N_2$ was added HCl (6 N in $CH_3OH$, 4 ml). The reaction was heated to 80° C. in a sealed tube. After stirring for 15 min., the reaction was treated with 1 N NaOH, extracted with $CH_2Cl_2$, dried over $K_2CO_3$, filtered and concentrated under vacuum to yield the free imidazole (0.092 g, 77%) which was used in the next reaction without further purification.

The imidazole (0.092 g, 0.18 mmol) in AcOH (3 ml) and $Ac_2O$ (90 µL, 0.90 mmol) was heated to 140° C. After 2.25 h, the AcOH was evaporated off and water was added, followed by a few drops of EtOAc. The mixture was stirred for a few minutes, then basified with $K_2CO_3$, extracted with EtOAc, dried over $K_2CO_3$ and concentrated under vacuum. The residue was subjected to PTLC (4:96 2 M $NH_3$ in $CH_3OH/CH_2Cl_2$) to yield the product (0.059 g, 68%). $^1H$ NMR (400 MHz, $CDCl_3$): δ 8.76 (d, 1H, J=8.8 Hz), 8.30 (dd, 1H, J=1.2, 7.4 Hz), 8.14 (d,1H, J=8.2 Hz), 8.03–7.91 (m, 3H), 7.73–7.58 (m, 3H), 7.54–7.46 (m, 2H), 7.35 (s, 1H), 6.41 (bs, 1H), 4.00 (m, 2H), 3.56 (t, 2H, J=5.7 Hz), 2.79 (m, 2H). HRMS: Calc'd for $C_{25}H_{20}N_3O_2SF_3$ (M+H)$^+$: 484.1307. Found: 484.1317.

Using appropriate starting materials and essentially the same procedure, the following compound was prepared:

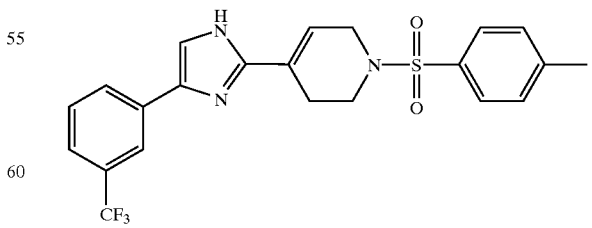

17A

HRMS: Calc'd for $C_{22}H_{20}N_3O_2SF_3$ (M+H)$^+$: 448.1307. Found: 448.1308.

EXAMPLE 18

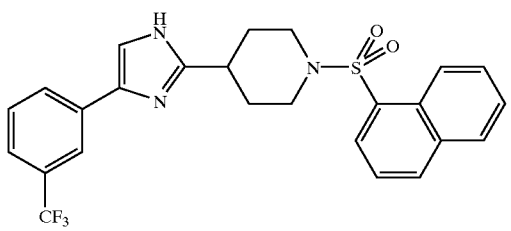

To a solution of Example 17 (0.037 g, 0.077 mmol) in EtOH (2.5 ml) was added 10% Pd/C. The mixture was stirred under a balloon of $H_2$ for 16 h, then filtered through celite, and the filter pad was washed with EtOH. The combined filtrate and washings were concentrated under vacuum. The residue was subjected to PTLC (4:96 2 M $NH_3$ in $CH_3OH/CH_2Cl_2$) to yield the product (0.019 g, 50%). $^1$H NMR (400 MHz, $CDCl_3$): δ 8.77 (d, 1H, J=8.8 Hz), 8.27 (dd, 1H, J=1.2, 7.4 Hz), 8.14 (d, 1H, J=8.2 Hz), 8.03–7.92 (m, 2H), 7.86 (bd, 1H, J=7.0 Hz), 7.74–7.58 (m, 3H), 7.51–7.42 (m, 2H), 7.30 (s, 1H), 4.01 (m, 2H), 2.90 (m, 2H), 2.78 (m, 2H), 2.20–2.08 (m, 2H), 2.01–1.86 (m, 2H). HRMS: Calc'd for $C_{25}H_{22}N_3O_2SF_3$ $(M+H)^+$: 486.1463. Found: 486.1466.

Using appropriate starting materials and essentially the same procedure, the following compound was prepared:

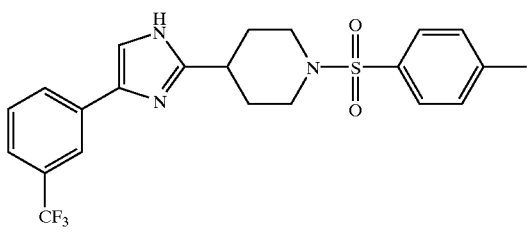

18A

HRMS: Calcd for $C_{22}H_{22}N_3O_2SF_3$ $(M+H)^+$: 450.1463. Found: 450.1457.

EXAMPLE 19

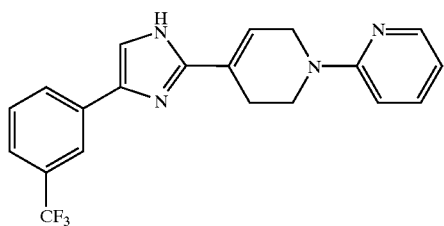

Step 1:

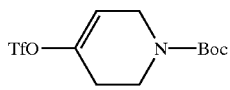

A solution of 1-Boc-4-piperidone (2.629 g, 13.19 mmol) in THF (7.5 ml) was added dropwise to freshly prepared LDA (9.3 ml of 1.6 M butyllithium in hexanes and 1.54 g diisopropylamine) in THF (15 ml) in a dry ice-acetone bath. After 1 h a solution of N-phenyltrifluoromethane-sulfonimide (4.851 g, 13.58 mmol) in THF (10 ml) was added and the solution was allowed to warm up to 0° C. and stirred in an ice-water bath for 4 h. The volatiles were evaporated and the residue was subjected to a flash column (neutral alumina, hexanes, then gradient of increasing EtOAc concentration to 4:96 EtOAc/hexanes) to give the product (1.440 g, 33%). $^1$H-NMR (400 MHz, $CDCl_3$) δ 5.74 (1H, b), 4.02 (2H, m), 3.61 (2H, m), 2.42 (2H, m), 1.45 (9H, s).

Step 2:

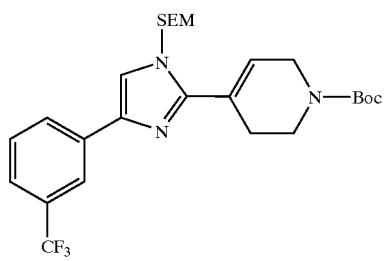

To a solution of the product of Preparation 2, Step 2 (359 mg, 1.05 mmol) in THF (5 ml) in a dry ice-acetone bath was added 1.6 M butyllithium in hexanes (0.80 ml, 1.3 mmol). The solution was stirred for 15 min. then zinc chloride (442 mg, 3.25 mmol) in THF (3 ml) was added. The mixture was stirred at −78° C. for 10 min. and warmed to R.T. over 30 min. 1,1'-Bis(diphenylphosphino)ferrocene-palladium dichloride (68 mg, 0.083 mmol) and the product of Step 1 (480 mg, 1.45 mmol) were added. The mixture was purged with nitrogen for 5 min. and then heated at 90° C. for 16 h. The reaction mixture was cooled down and poured into 10% aqueous $NH_4OH$ (50 ml). The whole was extracted with $CH_2Cl_2$ (2×50 ml), dried ($MgSO_4$), concentrated, and purified by PTLC (1:4 EtOAc/hexanes) to give the product (114 mg, 21%). MS (ES) m/e 524 $(M+H)^+$.

Step 3:

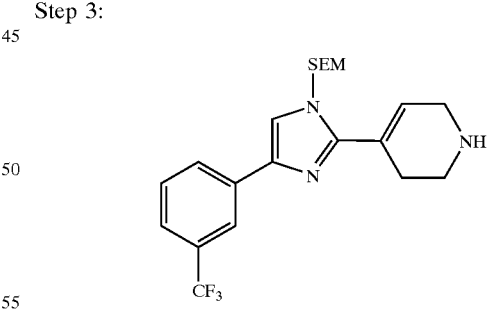

A solution of the product of Step 2 (114 mg, 0.218 mmol) in 10% $TFA/CH_2Cl_2$ (5 ml) was stirred in an ice-water bath for 10 min. then at R.T. for 2 h. The solution was partitioned between $CH_2Cl_2$ (30 ml) and 1N NaOH (20 ml). The aqueous layer was extracted again with $CH_2Cl_2$ (20 ml) and the combined organic layer was dried over $MgSO_4$. The crude mixture after concentration was subjected to PTLC (8:92 2M $NH_3$-MeOH/$CH_2Cl_2$) to give the product (67 mg, 73%). MS (ES) m/e 424 $(M+H)^+$.

Step 4:

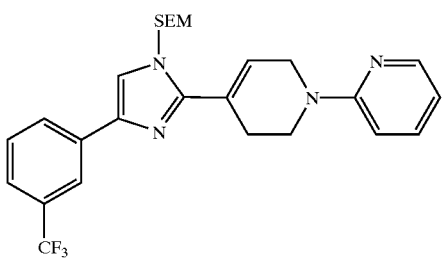

A mixture of the product of Step 3 (67 mg, 0.16 mmol), 2-bromopyridine (61 mg, 0.38 mmol), sodium t-butoxide (53 mg, 0.55 mmol), bis(diphenylphosphino)propane (16 mg, 0.039 mmol), and palladium(II) acetate (7 mg, 0.03 mmol) in toluene (4 ml) was heated at 100° C. in a sealed vessel for 16 h. The mixture was diluted with CH$_2$Cl$_2$ (40 ml) and filtered. The filtrate was evaporated to dryness and subjected to PTLC (3:97 MeOH/CH$_2$Cl$_2$) to give the product (36 mg, 45%). MS (ES) m/e 501 (M+H)$^+$.

Step 5:

Reaction of the product of Step 4 with HCl/MeOH by the procedure of Example 5, Step 4 afforded the product (13 mg, 48%). $^1$H-NMR (400 MHz, CDCl$_3$) δ 8.16 (1H, m), 7.99 (1H, s), 7.90 (1H, m), 7.53 (1H, m), 7.47 (2H, m), 7.34 (1H, s), 6.68 (1H, m), 6.63 (1H, m), 6.51 (1H, m), 4.17 (2H, m), 3.83 (2H, m), 2.79 (2H, m). MS (ES) m/e 371 (M+H)$^+$.

EXAMPLE 20

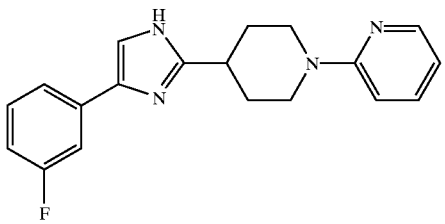

Step 1:

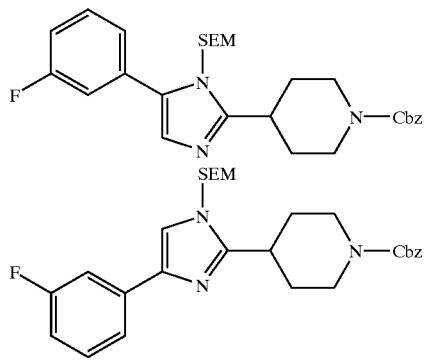

20-1-1

A mixture of Preparation 3 (0.693 g, 1.40 mmol), 3-fluorophenylboronic acid (0.410 g, 2.93 mmol), potassium phosphate (0.650 g, 3.07 mmol), and 1,1'-bis(diphenylphosphino)ferrocene-palladium dichloride (0.064 g, 0.078 mmol) in DME (5 ml) was heated at 80° C. in a sealed vessel for 16 h. The mixture was diluted with CH$_2$Cl$_2$ (50 ml) and filtered. The filtrate was washed with water (30 ml), dried (MgSO$_4$), concentrated, and purified by PTLC (2.5:97.5 MeOH/CH$_2$Cl$_2$) to give isomer A (0.214 g, 30%) and isomer B (0.263 g, 37%). MS (ES) m/e 510 (M+H)$^+$.

Coupling of Preparation 3 with the appropriate boronic acids by essentially the same procedure gave:

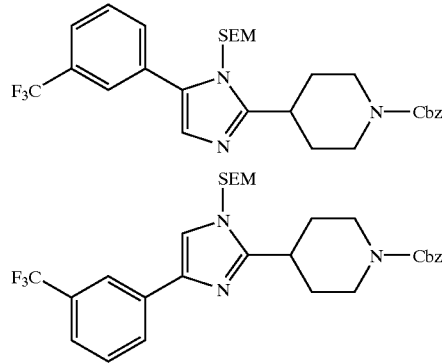

20-1-2  MS (ES) m/e 560 (M + H)$^+$.

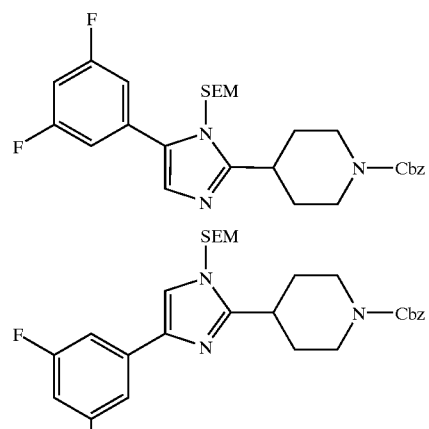

20-1-3  MS (ES) m/e 528 (M + H)$^+$.

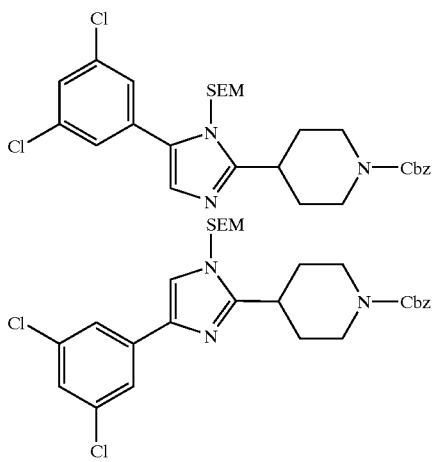

20-1-4  MS (ES) m/e 560 (M + H)$^+$.

Step 2:

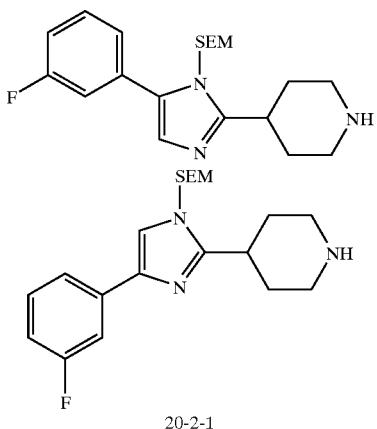

20-2-1

A mixture of 20-1-1 (0.214 g, 0.421 mmol) and 10% Pd/C (0.023 g) in EtOH (8 ml) was stirred under $H_2$ (1 atm) for 16 h. The mixture was filtered and the filtrate was evaporated to dryness to give the product (0.158 g, 100%). MS (ES) m/e 376 $(M+H)^+$.

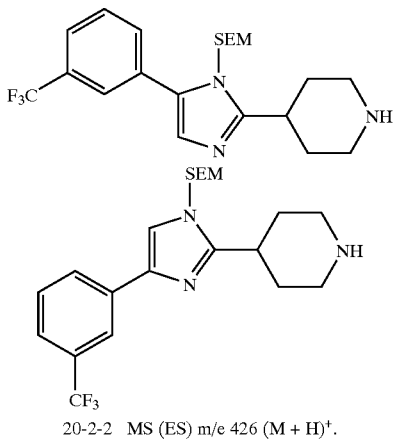

20-2-2  MS (ES) m/e 426 $(M + H)^+$.

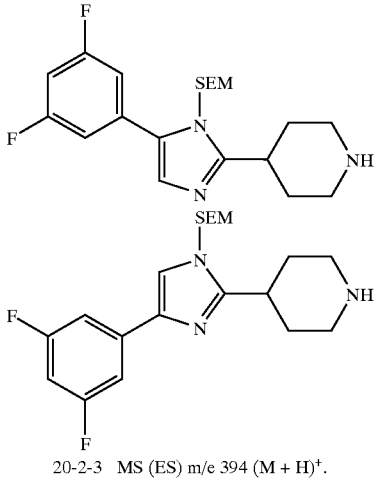

20-2-3  MS (ES) m/e 394 $(M + H)^+$.

Additional piperidine derivatives were prepared from 20-1-4 according to the following procedure.

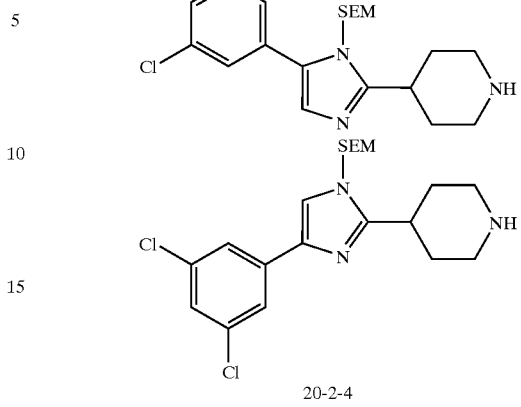

20-2-4

A mixture of 20-1-4 (179 mg, 0.319 mmol), 50% aq. KOH (6 ml), and EtOH (6 ml) was heated at 100° C. for 3 h. The mixture was concentrated and the residue was partitioned between $CH_2Cl_2$ (50 ml) and water (20 ml). The aqueous layer was washed with $CH_2Cl_2$ (20 ml). The combined organic layer was dried ($Na_2SO_4$) and concentrated to give the product (164 mg), which was used without further purification. MS (ES) m/e 426 $(M+H)^+$.

Step 3:

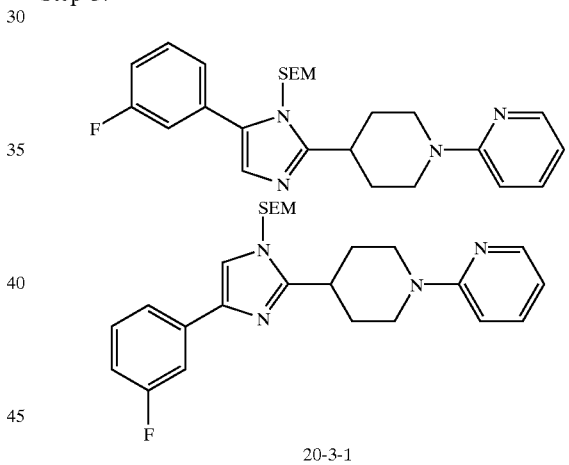

20-3-1

A mixture of 20-2-1 (81 mg, 0.21 mmol), 2-bromopyridine (88 mg, 0.56 mmol), palladium(II) acetate (10 mg, 0.045 mmol), bis(diphenylphosphino)propane (26 mg, 0.063 mmol), and sodium t-butoxide (88 mg, 0.92 mmol) in anhydrous toluene (4 ml) was heated at 110° C. in a sealed vessel for 16 h. The mixture was diluted with $CH_2Cl_2$ (40 ml) and filtered. The filtrate was evaporated to dryness and purified by PTLC (2:98 MeOH/$CH_2Cl_2$) to give the product (58 mg, 61%). MS (ES) m/e 453 $(M+H)^+$.

Step 4:

Reaction of 20-3-1 with HCl/MeOH by the procedure of Example 5, Step 4 afforded the product (43 mg, 100%). $^1$H-NMR (400 MHz, CDCl$_3$) δ 8.16 (1H, m), 7.45 (3H, m), 7.28 (1H, m), 7.19 (1H, s), 6.88 (1H, m), 6.67 (1H, m), 6.59 (1H, m), 4.35 (2H, m), 3.04 (1H, m), 2.95 (2H, m), 2.11 (2H, m), 1.81 (2H, m). MS (ES) m/e 323 $(M+H)^+$.

The following examples were prepared from the corresponding products of Step 2 using essentially the same procedures described in Step 3 and Step 4:

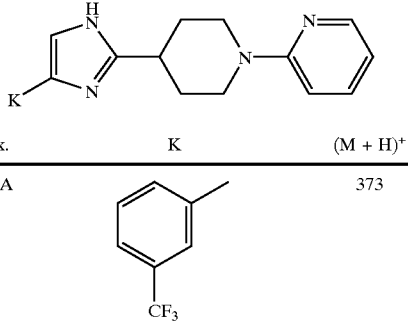

| Ex. | K | (M + H)+ |
|---|---|---|
| 20A | 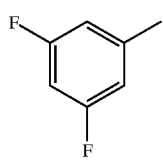 | 373 |
| 20B | 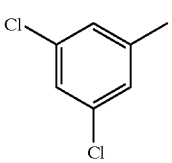 | 341 |
| 20C | 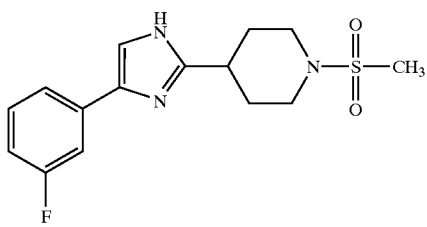 | 373 |

EXAMPLE 21

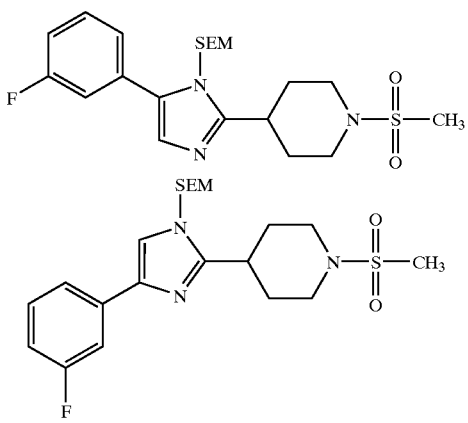

Step 1:

A solution of 20-2-1 (40 mg, 0.11 mmol), methanesulfonyl chloride (14 mg, 0.12 mmol), and triethylamine (20 mg, 0.20 mmol) in $CH_2Cl_2$ (4 ml) was stirred at R.T. for 16 h. The mixture was diluted with $CH_2Cl_2$ (40 ml) and washed with 1N NaOH (10 ml). The organic layer was dried ($MgSO_4$), concentrated, and purified by PTLC (2:98 MeOH/$CH_2Cl_2$) to give the product (34 mg, 68%). MS (ES) m/e 454 $(M+H)^+$.

Step 2:

Reaction of the product of Step 1 with HCl/MeOH by the procedure of Example 5, Step 4 afforded the product (23 mg, 96%). $^1$H-NMR (400 MHz, $CDCl_3$) δ 7.42 (2H, m), 7.29 (1H, m), 7.22 (1H, s), 6.90 (1H, m), 3.86 (2H, m), 2.96 (1H, m), 2.82 (5H, m), 2.14 (2H, m), 1.91 (2H, m). MS (ES) m/e 324 $(M+H)^+$.

The following examples were prepared from the corresponding products of Example 20, Step 2 using essentially the same procedures described in Step 1 and Step 2:

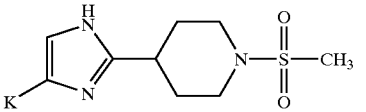

| Ex. | K | (M + H)+ |
|---|---|---|
| 21A | 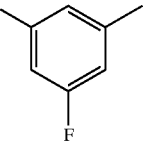 | 374 |
| 21B | 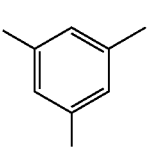 | 342 |
| 21C | 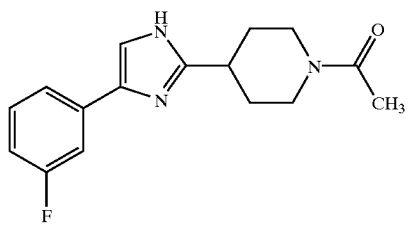 | 374 |

EXAMPLE 22

Step 1:

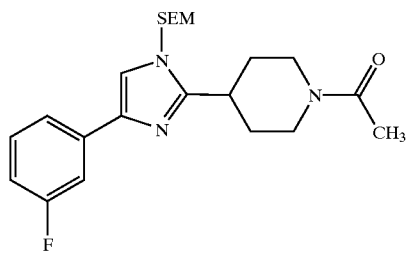

A solution of 20-2-1 (40 mg, 0.11 mmol), acetic anhydride (12 mg, 0.12 mmol), and triethylamine (24 mg, 0.24 mmol) in CH$_2$Cl$_2$ (4 ml) was stirred at R.T. for 16 h. The mixture was diluted with CH$_2$Cl$_2$ (40 ml) and washed with 1N NaOH (10 ml). The organic layer was dried (MgSO$_4$), concentrated, and purified by PTLC (2:98 MeOH/CH$_2$Cl$_2$) to give the product (30 mg, 69%). MS (ES) m/e 418 (M+H)$^+$.

Step 2:

A solution of the product of Step 1 (30 mg, 0.072 mmol) in MeOH (1 ml) and 5N HCl (3 ml) was refluxed for 4 h. The mixture was partitioned between CH$_2$Cl$_2$ (30 ml) and aqueous NH$_4$OH (15 ml). The organic layer was concentrated and the residue was reacted with acetic anhydride (8 mg, 0.08 mmol) in CH$_2$Cl$_2$ (5 ml) at R.T. for 16 h. The mixture was diluted with CH$_2$Cl$_2$ (30 ml) and washed with 1 N NaOH (10 ml). The organic layer was dried (MgSO$_4$), concentrated, and purified by PTLC (5:95 MeOH/CH$_2$Cl$_2$) to give the product (14 mg, 66%). $^1$H-NMR (400 MHz, CDCl$_3$) δ 7.42 (2H, m), 7.29 (1H, m), 7.23 (1H, s), 6.88 (1H, m), 4.66 (1H, m), 3.91 (1H, m), 3.21 (1H, m), 3.09 (1H, m), 2.73 (1H, m), 2.14 (1H, m), 2.11 (3H, s), 2.01 (1H, m), 1.74 (2H, m). MS (ES) m/e 288 (M+H)$^+$.

The following examples were prepared from the corresponding products of Example 20, Step 2 using essentially the same procedures described in Step 1 and Step 2:

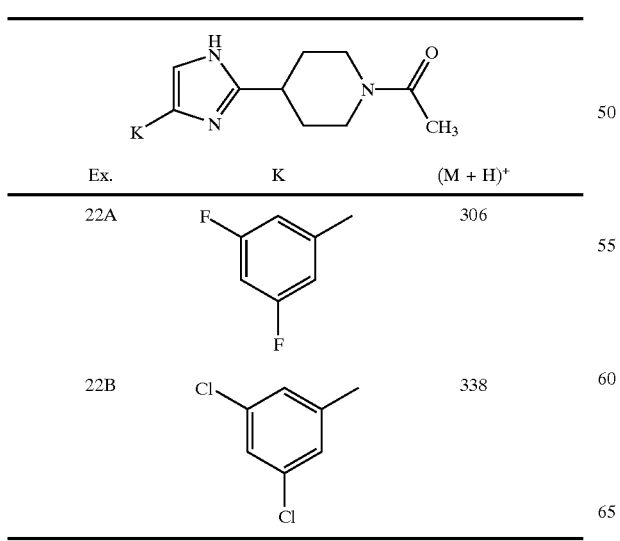

| Ex. | K | (M + H)$^+$ |
|---|---|---|
| 22A | F-phenyl-F | 306 |
| 22B | Cl-phenyl-Cl | 338 |

EXAMPLE 23

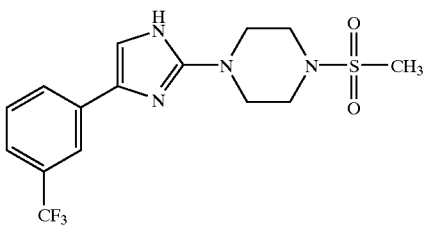

Step 1:

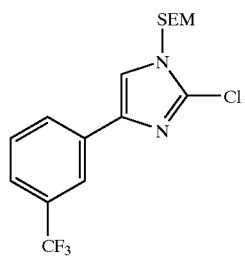

To a solution of Preparation 2 (8.734 g, 18.65 mmol) in anhydrous THF (35 ml) at −78° C. was added 2.5 M butyllithium in hexanes (9.50 ml, 23.8 mmol). The solution was stirred at −78° C. for 40 min and a solution of hexachloroethane (9.69 g, 40.9 mmol) in THF (25 ml) was added through a cannular. The resulting solution was allowed to warm to R.T. and stirred for 16 h. The solution was evaporated to dryness and the residue was partitioned between CH$_2$Cl$_2$ (300 ml) and water (200 ml). The organic layer was dried (MgSO$_4$), concentrated, and purified by column chromatography (hexanes, then gradient of increasing EtOAc concentration to 4:96 EtOAc/hexanes) to give the product (6.189 g, 88%). MS (ES) m/e 377 (M+H)$^+$.

Step 2:

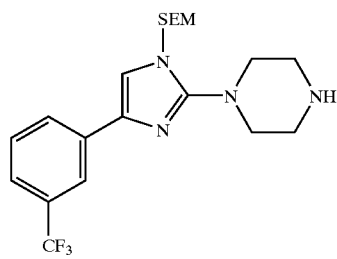

A mixture of the product of Step 1 (5.142 g, 13.64 mmol), piperazine (53.06 g, 615.9 mmol), copper(II) sulfate (9.05 g, 56.7 mmol) in diglyme (10 ml) was heated to 170° C. for 48 h in a sealed vessel. The reaction mixture was cooled to R.T. and treated with CH$_2$Cl$_2$ (600 ml). The mixture was filtered and the filtrate was washed with water (2×350 ml). The organic layer was dried (MgSO$_4$), concentrated, and purified by column chromatography (CH$_2$Cl$_2$, then gradient of increasing MeOH concentration to 1:9 MeOH/CH$_2$Cl$_2$) to give the product (4.116 g, 71%). MS (ES) m/e 427 (M+H)$^+$.

Step 3:

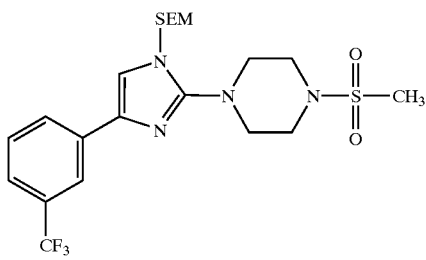

A solution of the product of Step 2 (75 mg, 0.18 mmol), methanesulfonyl chloride (29 mg, 0.26 mmol), and triethylamine (38 mg, 0.38 mmol) in $CH_2Cl_2$ (5 ml) was stirred at R.T. for 16 h. The mixture was diluted with $CH_2Cl_2$ (50 ml) and washed with 1 N NaOH (20 ml), then sat'd aq. $NH_4Cl$ (20 ml). The organic layer was dried ($MgSO_4$), concentrated, and subjected to PTLC (2:98 MeOH/$CH_2Cl_2$) to give the product (73 mg, 81%). MS (ES) m/e 505 $(M+H)^+$.

Step 4:

A solution of the product of Step 3 (73 mg, 0.14 mmol) in MeOH (3 ml) and 5N HCl (7 ml) was refluxed for 4 h. The reaction mixture was partitioned between $CH_2Cl_2$ (40 ml) and aq. $NH_4OH$ (20 ml). The organic layer was dried ($MgSO_4$), concentrated, and subjected to PTLC (5:95 MeOH/$CH_2Cl_2$) to give the product (52 mg, 97%). $^1$H-NMR (400 MHz, $CDCl_3$) δ 7.87 (1H, s), 7.80 (1H, m), 7.42 (2H, m), 7.04 (1H, s), 3.50 (4H, t, J=5 Hz), 3.34 (4H, t, J=5 Hz), 2.80 (3H, s). MS (ES) m/e 375 $(M+H)^+$.

By using appropriate starting materials and essentially the same procedure, the following compounds were prepared:

| Ex. | $R^7$ | $(M + H)^+$ |
| --- | --- | --- |
| 23A | —$CH_2CH_3$ | 389 |
| 23B | —$CH_2CH_2CH_3$ | 403 |
| 23C | isopropyl | 403 |
| 23D | phenyl | 437 |
| 23E | —$CF_3$ | 429 |

EXAMPLE 24

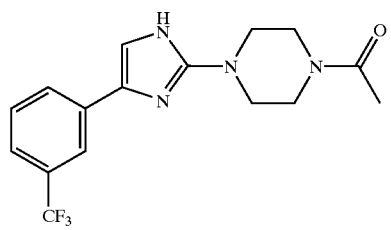

Step 1:

A solution of the product of Example 23, Step 2 (602 mg, 1.41 mmol) in MeOH (5 ml) and 5N HCl (9 ml) was refluxed for 3 h. The reaction mixture was partitioned between $CH_2Cl_2$ (3×60 ml) and aq. $NH_4OH$ (50 ml). The organic layer was dried ($MgSO_4$), concentrated, and subjected to PTLC (16:84 2M $NH_3$ in MeOH/$CH_2Cl_2$) to give the product (343 mg, 82%). MS (ES) m/e 297 $(M+H)^+$.

Step 2:

A solution of the product of Step 1 (31 mg, 0.11 mmol), acetyl chloride (8 mg, 0.1 mmol), and triethylamine (11 mg, 0.11 mmol) in $CH_2Cl_2$ (2 ml) was stirred at R.T. for 16 h. The mixture was diluted with $CH_2Cl_2$ (25 ml) and washed with water (20 ml). The organic layer was dried ($MgSO_4$), concentrated, and subjected to PTLC (5:95 MeOH/$CH_2Cl_2$) to give the product (17 mg, 47%). $^1$H-NMR (400 MHz, $CDCl_3$) δ 8.75 (1H, b), 7.85 (2H, m), 7.41 (2H, m), 7.05 (1H, s), 3.73 (2H, m), 3.60 (2H, m), 3.47 (2H, m), 3.29 (2H, m), 2.13 (3H, s). MS (ES) m/e 339 $(M+H)^+$.

By using appropriate starting materials and essentially the same procedure, the following compounds were prepared:

| Ex. | $R^{8a}$ | $(M + H)^+$ |
| --- | --- | --- |
| 24A | cyclopropyl | 365 |
| 24B | phenyl | 401 |

-continued

| Ex. | R8a | (M + H)+ |
|---|---|---|
| 24C | 2-pyridyl | 402 |
| 24D | 3-pyridyl | 402 |
| 24E | 4-pyridyl | 402 |

EXAMPLE 25

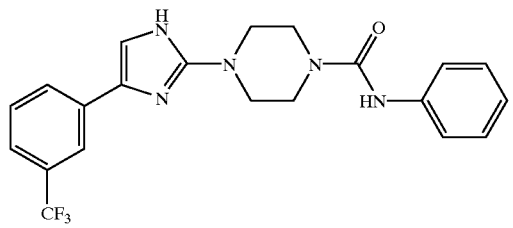

To a solution of the product of Example 24, Step 1 (31 mg, 0.10 mmol) and triethylamine (11 mg, 0.11 mmol) in CH$_2$Cl$_2$ (2 ml) was added phenylisocyanate (13 mg, 0.11 mmol) in CH$_2$Cl$_2$ (1 ml) dropwise. The mixture was stirred at R.T. for 16 h and then evaporated to dryness. The residue was purified by PTLC (5:95 MeOH/CH$_2$Cl$_2$) to give the product (23 mg, 54%). $^1$H-NMR (400 MHz, CDCl$_3$) δ 7.86 (1H, b), 7.75 (1H, b), 7.2–7.4 (6H, m), 7.07 (1H, m), 6.72 (2H, b), 3.53 (4H, m), 3.38 (4H, m). MS (ES) m/e 416 (M+H)$^+$.

By using appropriate starting materials and essentially the same procedure, the following compounds were prepared:

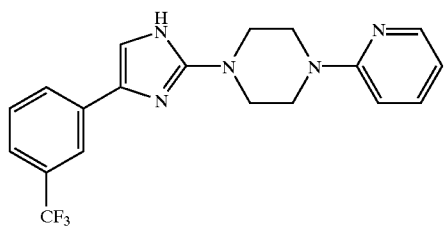

| Ex. | Z | (M + H)+ |
|---|---|---|
| 25A | —H | 340 |
| 25B | t-butyl | 396 |
| 25C | cyclohexyl | 422 |

EXAMPLE 26

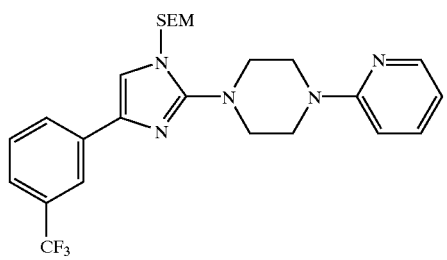

Step 1:

26-1-1

A mixture of the product of Example 23, Step 2 (123 mg, 0.288 mmol), palladium acetate (7 mg, 0.03 mmol), bis(diphenylphosphino)propane (10 mg, 0.024 mmol), sodium t-butoxide (87 mg, 0.91 mmol), and 2-bromopyridine (114 mg, 0.722 mmol) in anhydrous toluene (2.5 ml) was heated to 80° C. in a sealed vessel for 16 h. The mixture was diluted with CH$_2$Cl$_2$ (50 ml) and filtered. The filtrate was evaporated to dryness and purified by PTLC (3:97 MeOH/CH$_2$Cl$_2$) to give the product (120 mg, 83%). MS (ES) m/e 504 (M+H)$^+$.

Coupling of the product of Example 23, Step 2 with the appropriate aryl or heteroaryl halides by essentially the same procedure gave:

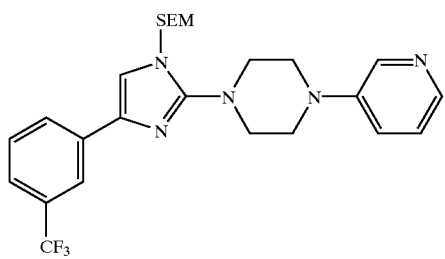

26-1-2  MS (ES) m/e 504 (M + H)⁺.

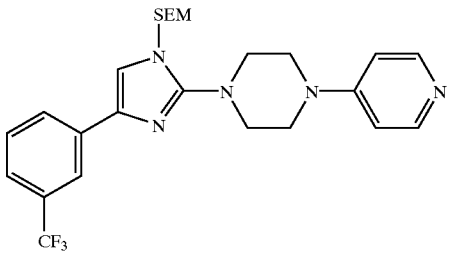

26-1-3  MS (ES) m/e 504 (M + H)⁺.

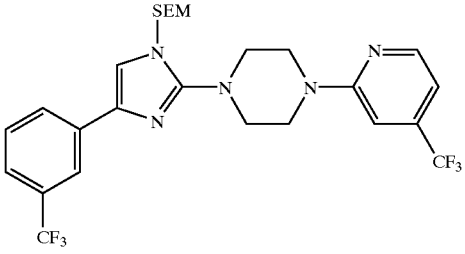

26-1-4  MS (ES) m/e 572 (M + H)⁺.

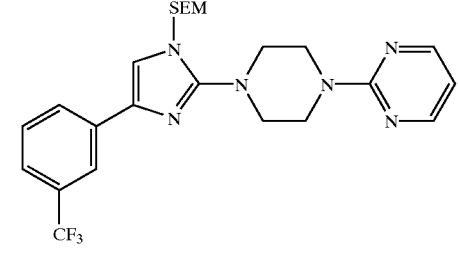

26-1-5  MS (ES) m/e 505 (M + H)⁺.

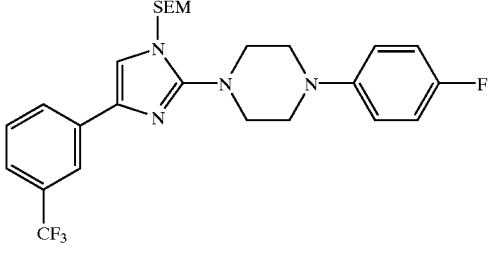

26-1-6  MS (ES) m/e 521 (M + H)⁺.

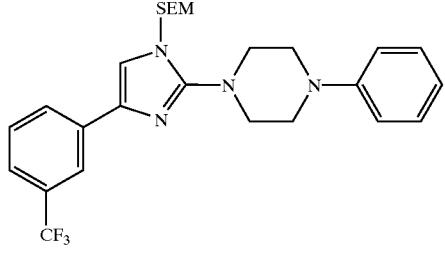

26-1-7  MS (ES) m/e 503 (M + H)⁺.

Additional (4'-aryl or 4'-heteroarylpiperazinyl)imidazoles were prepared according to the following procedure.

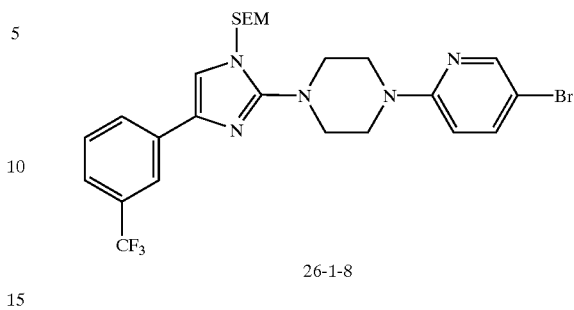

26-1-8

A mixture of the product of Example 23, Step 2 (132 mg, 0.309 mmol), 2,5-dibromopyridine (151 mg, 0.637 mmol), bis(dibenzylideneacetone)palladium (10 mg, 0.017 mmol), (±)-2,2'-bis(diphenylphosphino)-1,1'-binaphthyl (23 mg, 0.037 mmol), and sodium t-butoxide (85 mg, 0.88 mmol) in anhydrous toluene (2.5 ml) was heated to 110° C. in a sealed vessel for 16 h. The mixture was diluted with $CH_2Cl_2$ (40 ml) and filtered. The filtrate was evaporated to dryness and purified by PTLC (1.5:98.5 $MeOH/CH_2Cl_2$) to give the product (118 mg, 65%). MS (ES) m/e 582 (M+H)⁺.

Using the appropriate aryl or heteroaryl halides and essentially the same procedure, the following compounds were prepared.

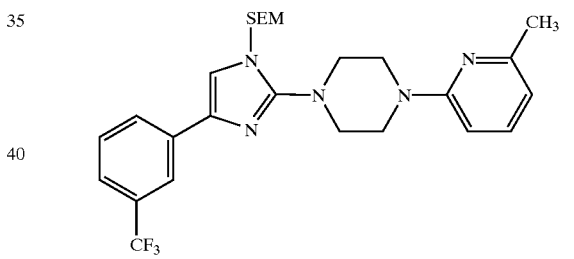

26-1-9  MS (FAB) m/e 518 (M + H)⁺.

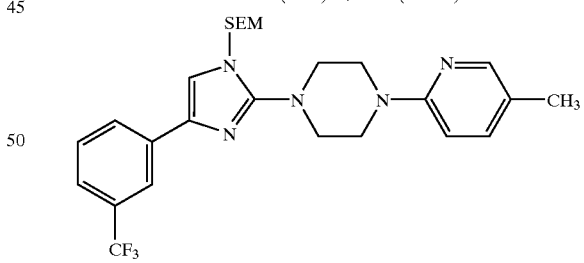

26-1-10  MS (ES) m/e 518 (M + H)⁺.

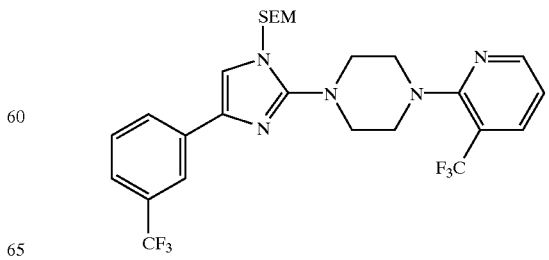

26-1-11  MS (ES) m/e 572 (M + H)⁺.

26-1-12 MS (ES) m/e 505 (M + H)+.

26-1-13 MS (ES) m/e 521 (M + H)+.

26-1-14 MS (ES) m/e 521 (M + H)+.

Step 2:

A solution of 26-1-1 (120 mg, 0.238 mmol) in MeOH (3 ml) and 5N HCl (5 ml) was refluxed for 4 h. The reaction mixture was partitioned between $CH_2Cl_2$ (50 ml) and aq. $NH_4OH$ (20 ml). The organic layer was dried ($MgSO_4$), concentrated, and purified by PTLC (5:95 MeOH/$CH_2Cl_2$) to give the product (89 mg, 100%). $^1$H-NMR (400 MHz, $CDCl_3$) δ 8.18 (1H, m), 7.88 (1H, s), 7.80 (1H, m), 7.49 (1H, m), 7.40 (2H, m), 7.05 (1H, s), 6.66 (2H, m), 3.65 (4H, m), 3.48 (4H, m). MS (ES) m/e 374 (M+H)+.

The following examples were prepared from the corresponding products of Step 1 using essentially the same procedure.

| Ex. | R8 | (M + H)+ |
|---|---|---|
| 26A | 3-pyridyl | 374 |
| 26B | 4-pyridyl | 374 |
| 26C | 2-methyl-4-CF3-pyridyl | 442 |
| 26D | 2-pyrimidinyl | 375 |
| 26E | 4-fluorophenyl | 391 |
| 26F | phenyl | 373 |
| 26G | 2-methyl-5-bromo-pyridyl | 452 |
| 26H | 2,6-dimethyl-pyridyl | 388 |
| 26I | 2,5-dimethyl-pyridyl | 388 |
| 26J | 2-methyl-3-CF3-pyridyl | 442 |
| 26K | 5-pyrimidinyl | 375 |
| 26L | 2-methyl-3-fluoro-phenyl | 391 |

-continued

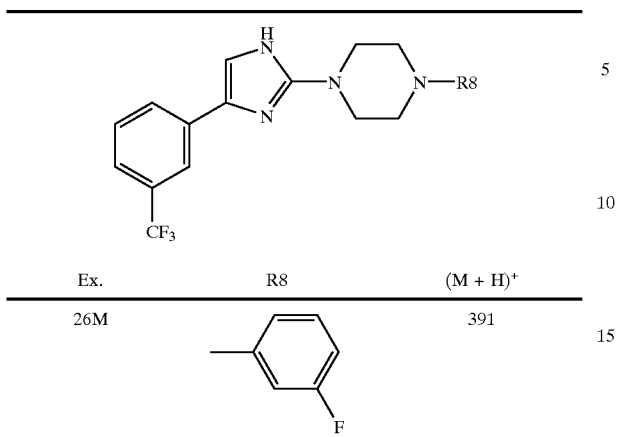

| Ex. | R8 | (M + H)+ |
|---|---|---|
| 26M | 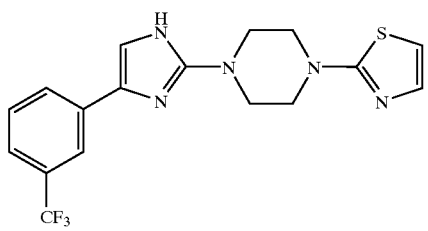 | 391 |

EXAMPLE 27

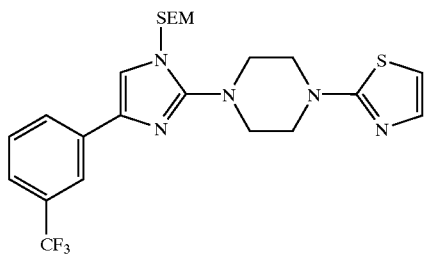

Step 1:

A mixture of the product of Example 23, Step 2 (107 mg, 0.251 mmol), 2-bromothiazole (93 mg, 0.57 mmol), and anhydrous potassium carbonate (98 mg, 0.71 mmol) in anhydrous DMF (2.5 ml) was heated at 160° C. for 16 h. The volatiles were evaporated in vacuo and the residue was partitioned between $CH_2Cl_2$ (50 ml) and 1N NaOH (20 ml). The organic layer was washed with water (30 ml) and brine (20 ml), dried ($MgSO_4$), concentrated, and purified by PTLC (2:98 MeOH/$CH_2Cl_2$) to give the product (71 mg, 55%). MS (ES) m/e 510 (M+H)+.

Step 2:

Reaction of the product of Step 1 with HCl/MeOH by the procedure of Example 5, Step 4 afforded the product (52 mg, 99%). $^1$H-NMR (400 MHz, $CDCl_3$) δ 7.88 (1H, s), 7.81 (1H, m), 7.42 (2H, m), 7.20 (1H, d, J=3.6 Hz), 7.05 (1H, s), 6.62 (1H, d, J=3.6 Hz), 3.61 (4H, m), 3.51 (4H, m). MS (ES) m/e 380 (M+H)+.

EXAMPLE 28

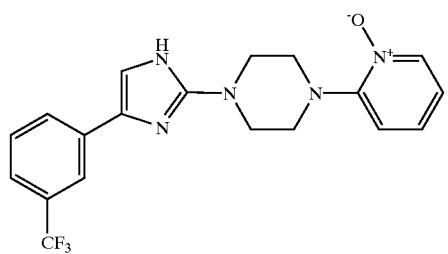

Step 1:

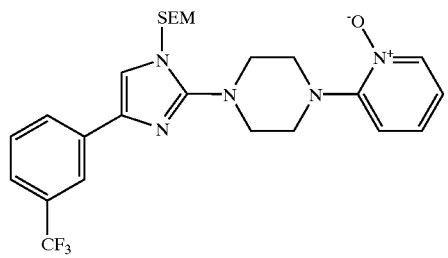

A solution of the product of Example 23, Step 2 (129 mg, 0.303 mmol), 2-chloropyridine N-oxide hydrochloride (77 mg, 0.46 mmol), and triethylamine (282 mg, 2.78 mmol) in EtOH (5 ml) was refluxed for 16 h. The volatiles were evaporated and the residue was partitioned between $CH_2Cl_2$ (40 ml) and water (20 ml). The organic layer was dried ($MgSO_4$), concentrated, and purified by PTLC (6:94 MeOH/$CH_2Cl_2$) to give the product (40 mg, 25%). MS (ES) m/e 520 (M+H)+.

Step 2:

Reaction of the product of Step 1 with HCl/MeOH by the procedure of Example 5, Step 4 afforded the product (28 mg, 94%). $^1$H-NMR (400 MHz, $CD_3OD$) δ 8.22 (1H, m), 7.95 (1H, s), 7.87 (1H, m), 7.4–7.6 (3H, m), 7.22 (2H, m), 7.13 (1H, m), 3.60 (4H, m), 3.55 (4H, m). MS (ES) m/e 390 (M+H)+.

EXAMPLE 29

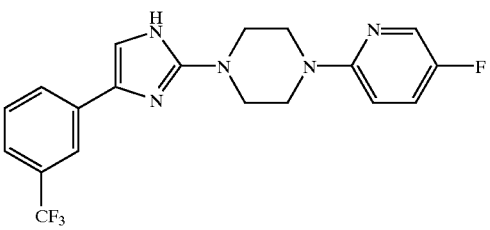

Step 1:

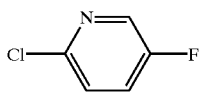

A stirred ice-cold solution of 2-chloro-5-aminopyridine (5.56 g, 43.2 mmol) in EtOH (50 ml) was treated with 50% aqueous $HBF_4$ (16 ml, 90 mmol). The mixture was cooled to −5° C. and isoamyl nitrite (6.1 ml, 45 mmol) was added dropwise over 5 min. The mixture was stirred for another 30 min. at −5° C. and then filtered. The filtercake was washed with absolute EtOH and ether to give a pale yellow solid (6.77 g). The solid in dry heptane (35 ml) was gently refluxed for 3 h. Upon cooling to R.T. the upper layer was decanted, and the residue was stirred with ether (60 ml). After ether was evaporated at 10° C. under reduced pressure, the residue was stirred with concentrated sulfuric acid (1 ml) for 16 h. The supernatant layer was decanted and the lower layer was rinsed with pentane (3×4 ml). Ice was added, followed by 5N NaOH (8 ml). The mixture was extracted with ether (50 ml, then 2×20 ml), dried (MgSO$_4$), and concentrated to give the product (1.5 g). $^1$H-NMR (400 MHz, CDCl$_3$) δ 8.26 (1H, d, J=3.2 Hz), 7.40 (1H, m), 7.32 (1H, dd, J=3.6, 8.8 Hz).

Step 2:

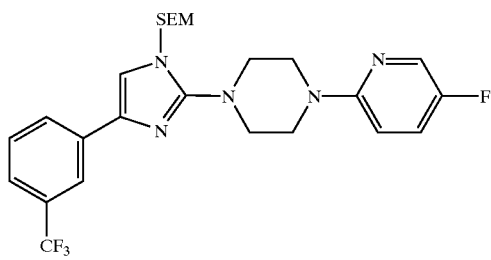

29-2-1

A mixture of the product of Example 23, Step 2 (97 mg, 0.23 mmol), the product of Step 1 (45 mg, 0.34 mmol), palladium(II) acetate (6 mg, 0.03 mmol), 2-(di-t-butylphosphino)biphenyl (7 mg, 0.02 mmol), and sodium t-butoxide (69 mg, 0.72 mmol) in toluene (2 ml) was heated to 100° C. in a sealed vessel for 3 h. The mixture was diluted with CH$_2$Cl$_2$ (40 ml) and filtered. The filtrate was evaporated to dryness and purified by PTLC (2:98 MeOH/CH$_2$Cl$_2$) to give the product (60 mg, 50%). MS (ES) m/e 522 (M+H)$^+$.

Coupling of the product of Example 23, Step 2 with 2-chloropyridine-5-carbonitrile by essentially the same procedure gave:

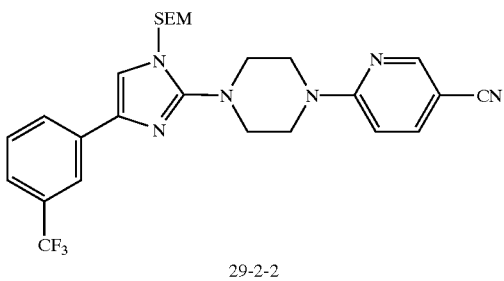

29-2-2

Step 3:

A solution of 29-2-1 (59 mg, 0.11 mmol) in MeOH (2 ml) and 5N HCl (5 ml) was refluxed for 3 h. The reaction mixture was partitioned between CH$_2$Cl$_2$ (50 ml) and aq. NH$_4$OH (25 ml). The organic layer was dried (MgSO$_4$), concentrated, and purified by PTLC (4:96 MeOH/CH$_2$Cl$_2$) to give the product (38 mg, 89%). $^1$H-NMR (400 MHz, CDCl$_3$) δ 8.05 (1H, d, J=3.2 Hz), 7.89 (1H, m), 7.81 (1H, m), 7.41 (2H, m), 7.26 (1H, m), 7.05 (1H, s), 6.66 (1H, dd, J=3.6, 9.2 Hz), 3.58 (4H, m), 3.48 (4H, m). MS (ES) m/e 392 (M+H)$^+$.

Reaction of 29-2-2 with HCl/MeOH by the procedure of Example 5, Step 4 afforded the following compounds:

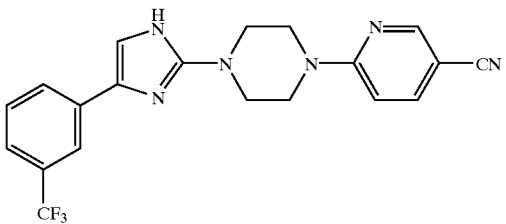

29A  MS (ES) m/e 399 (M + H)$^+$.

EXAMPLE 30

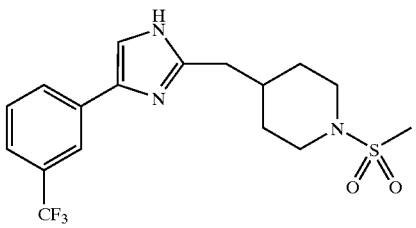

Step 1:

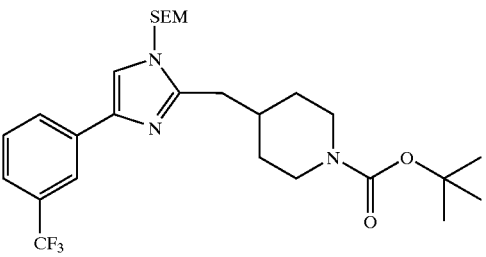

To an ice-cold solution of N-t-butoxycarbonyl-4-methylene-piperidine (*Tetrahedron Letters*, 37 (1996), 5233) (151 mg, 0.77 mmol) in THF (3 ml) was slowly added 9-BBN (0.5N in THF; 1.5 ml, 5.7 mmol). After 5 min. the cold bath was removed and stirring was continued at R.T. for 3 h to give solution A. Preparation 2 (350 mg, 0.75 mmol), CsCO$_3$ (299 mg, 0.92 mmol), triphenylarsine (24 mg, 0.08 mmol), and Pd(dppf)Cl$_2$ (24 mg, 0.03 mmol) in DMF (5 ml) and water (0.2 ml) was purged with N$_2$, and solution A was added via cannula. The reaction mixture was stirred overnight, then poured into ice-water and extracted with EtOAc (50 ml). The aqueous layer was basified to pH 10–11 and extracted with EtOAc (50 ml). The combined EtOAc layers were dried (MgSO$_4$), filtered and evaporated. Purification of the residue by PTLC (1:99 2 M NH$_3$ in CH$_3$OH/CH$_2$Cl$_2$) gave the product (177 mg, 49%).

$^1$H NMR (400 MHz, CD$_3$OD): δ 8.03 (s, 1H), 7.94 (d, 1H, J=8 Hz), 7.65 (s, 1H), 7.53 (m, 2H), 5.35 (s, 2H), 4.06 (m, 2H), 3.62 (t, 2H, J=8.2 Hz), 2.77 (m, 4H), 2.07 (m, 1H), 1.67 (m, 2H), 1.42 (s, 9H), 1.22 (m, 2H), 0.93 (t, 2H, J=8.2 Hz), −0.02 (s, 9H).

Step 2:

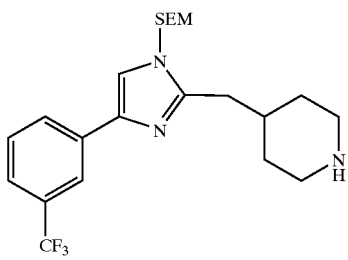

A solution of the product of Step 1 (558 mg, 1.18 mmol) in TFA (1.25 ml) and $CH_2Cl_2$ (10 ml) was stirred in an ice bath for 5 min., then at R.T. for 45 min. The reaction mixture was cooled in ice, then 1 N NaOH (20 ml) and $CH_2Cl_2$ (30 ml) was added. The organic layer was dried ($MgSO_4$), filtered and evaporated. The residue was purified by PTLC (6:94 2 M $NH_3$ in $CH_3OH/CH_2Cl_2$) to give the product (215 mg, 42%).

$^1$H NMR (400 MHz, $CDCl_3$): δ 7.99 (s, 1H), 7.93 (m, 1H), 7.46 (m, 2H), 7.25 (s, 1H), 5.22 (s, 2H), 3.51 (t, 2H, J=8.2 Hz), 3.09 (m, 2H), 2.70 (m, 2H), 2.62 (m, 2H), 2.04 (m, 1H), 1.93 (bs, 1H), 1.75 (m, 2H), 1.27 (m, 2H), 0.93 (t, 2H, J=8.6 Hz), −0.02 (s, 9H).

Step 3:

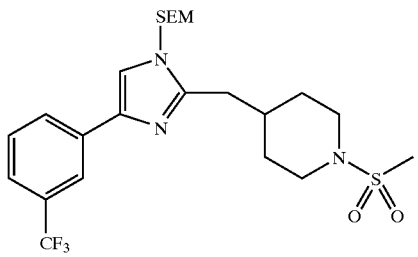

Reaction of the product of Step 2 (51 mg, 0.12 mmol) with $CH_3SO_2Cl$ by the procedure of Example 5, Step 3, gave the product (55 mg, 100%). $^1$H NMR (400 MHz, $CDCl_3$): δ 8.00 (s, 1H), 7.91 (m, 1H), 7.46 (m, 2H), 7.25 (s, 1H), 5.23 (s, 2H), 3.81 (m, 2H), 3.54 (t, 2H, J=8.6 Hz), 2.77 (s, 3H), 2.70 (m, 4H), 2.15 (m, 1H), 1.89 (m, 2H), 1.45 (m, 2H), 0.92 (t, 2H, J=8.6 Hz), −0.02 (s, 9H).

Step 4:

Using the procedure of Example 2, Step 4, reaction of the product of Step 3 (55 mg, 0.12 mmol) with $HCl/CH_3OH$ afforded the product (38 mg, 100%). $^1$H NMR (400 MHz, $CD_3OD$): δ 8.00 (s, 1H), 7.91 (d, J=7.2 Hz, 1H), 7.50 (m, 3H), 3.70 (m, 2H), 2.79 (s, 3H), 2.71 (m, 4H), 1.90 (m, 1H), 1.77 (m, 2H), 1.37 (m, 2H). MS (FAB) m/e 388 (M+H)$^+$.

Using appropriate starting materials and essentially the same procedure, the following compounds were prepared:

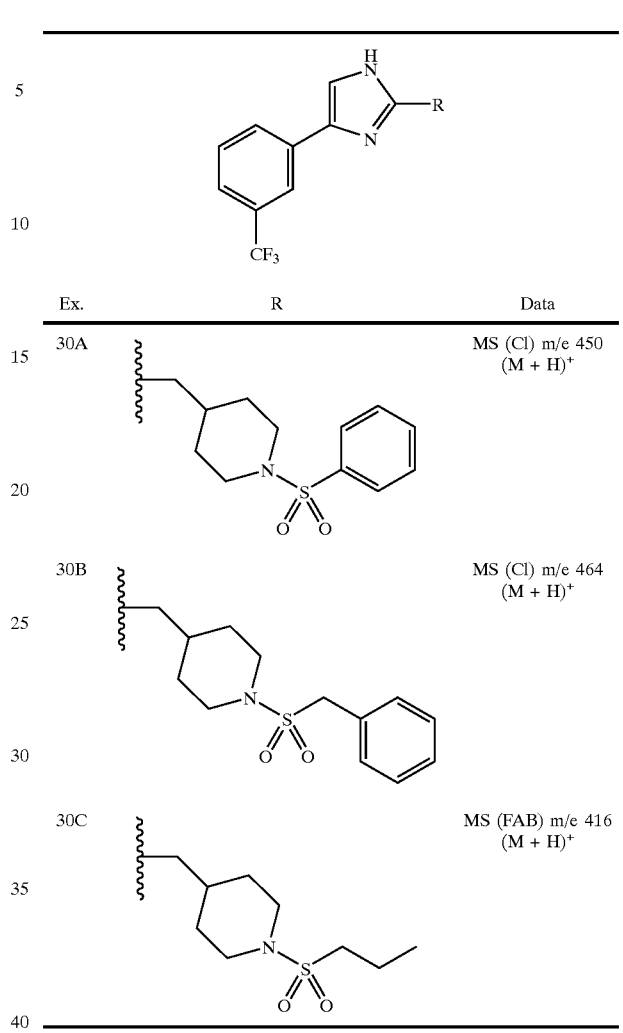

| Ex. | R | Data |
|---|---|---|
| 30A | (4-piperidinylmethyl, N-phenylsulfonyl) | MS (Cl) m/e 450 (M + H)$^+$ |
| 30B | (4-piperidinylmethyl, N-benzylsulfonyl) | MS (Cl) m/e 464 (M + H)$^+$ |
| 30C | (4-piperidinylmethyl, N-propylsulfonyl) | MS (FAB) m/e 416 (M + H)$^+$ |

EXAMPLE 31

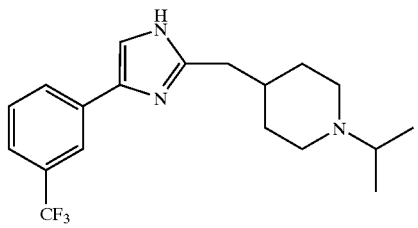

Step 1:

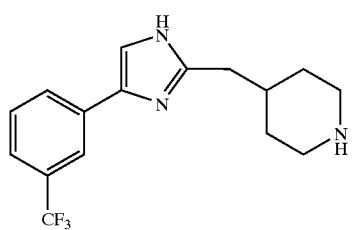

Using the procedure of Example 2, Step 4, reaction of the product of Example 30, Step 2 (177 mg, 0.40 mmol) with 5M HCl/CH$_3$OH afforded the product (74 mg, 60%). MS (Cl) m/e 310 (M+H)$^+$.

Step 2:

Using a procedure analogous to Example 4, Step 2, reductive alkylation of the product of Step 1 (33 mg, 0.11 mmol) with acetone gave the product (25 mg, 65%). $^1$H NMR (400 MHz, CD$_3$OD): δ 7.99 (s, 1H), 7.91 (d, 1H, J=7.6 Hz), 7.51 (m, 2H), 7.43 (s, 1H), 2.91 (m, 2H), 2.69 (m, 3H), 2.20 (m, 2H), 1.79 (m, 1H), 1.70 (m, 2H), 1.35 (m, 2H), 1.06 (d, 6H, J=6.6 Hz). MS (Cl) m/e 352 (M+H)$^+$.

Using appropriate starting materials and procedures, the following compounds were prepared:

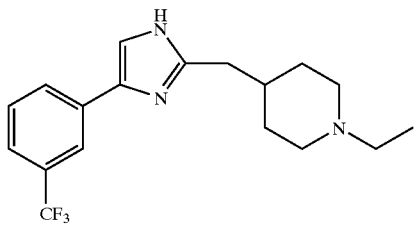

31A  MS (Cl) m/e 338 (M + H)$^+$

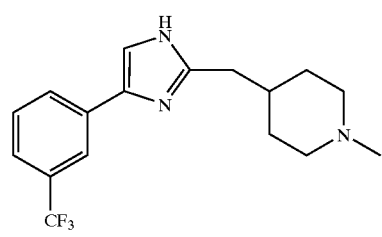

31B  MS (FAB) m/e 324 (M + H)$^+$

EXAMPLE 32

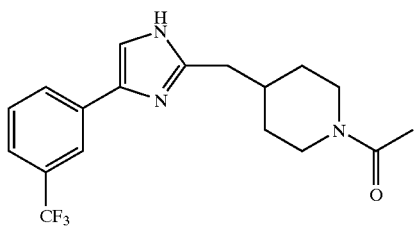

A solution of Example 31, Step 1 (27 mg, 0.087 mmol), acetic anhydride (15 μL, 0.16 mmol), Et$_3$N (45 μL, 0.32 mmol), and a catalytic amount of DMAP in CH$_2$Cl$_2$ (5 ml) was stirred at R.T. overnight. The reaction mixture was diluted with CH$_2$Cl$_2$ (30 ml) and washed with sat'd NH$_4$Cl (20 ml). The organic layer was dried (MgSO$_4$), filtered and evaporated. The residue was purified by PTLC (5:95 CH$_3$OH/CH$_2$Cl$_2$) to give the product (14 mg, 46%). $^1$H NMR (400 MHz, CD$_3$OD): δ 8.00 (s, 1H), 7.93 (m, 1H), 7.65–7.50 (m, 3H), 4.51 (m, 1H), 3.92 (m, 1H), 3.10 (m, 1H), 2.74 (m, 1H), 2.63 (m, 1H), 2.08 (s, 3H), 2.04 (m, 1H), 1.73 (m, 2H), 1.35–1.10 (m, 3H). MS (FAB) m/e 352 (M+H)$^+$.

What is claimed is:

1. A compound having the structural formula

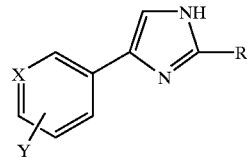

I or a pharmaceutically acceptable salt, solvate or N-oxide thereof, wherein

X is =CH— or =N—;

Y is 1 to 3 substituents independently selected from the group consisting of H, halogen, trihaloalkyl, C$_1$–C$_6$ alkyl, C$_1$–C$_6$ alkenyl, C$_3$–C$_7$-cycloalkyl, C$_1$–C$_6$ alkyl substituted by C$_3$–C$_7$-cycloalkyl, —OH, —O(C$_1$–C$_6$) alkyl, —SH, —S(C$_1$–C$_6$)alkyl, or —CN;

R is

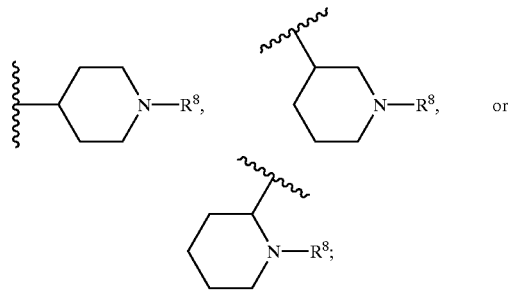

R$^4$ is hydrogen or C$_1$–C$_6$ alkyl;

R$^5$ is C$_1$–C$_6$ alkyl, aryl or heteroaryl; provided R$^4$ and R$^5$ are not both C$_1$–C$_6$ alkyl, and provided that when R$^4$ is hydrogen, R$^5$ is not C$_1$–C$_6$ alkyl; or R$^4$ and R$^5$ together are C$_3$–C$_6$ alkylene and together with the nitrogen to which they are attached form a 4–7 membered ring; or R$^4$ and R$^5$, together with the nitrogen to which they are attached, form a 5, 6 or 7-membered ring, wherein 1 or 2 ring members are independently selected from the group consisting of —O—, —S— and —NR$^{12}$—;

R$^7$ is C$_1$–C$_6$ alkyl, C$_3$–C$_7$ cycloalkyl, benzyl, aryl, or heteroaryl;

R$^8$ is hydrogen, C$_1$–C$_6$ alkyl, —C(O)—(C$_1$–C$_6$ alkyl), —C(O)—(C$_3$–C$_7$ cycloalkyl), —C(O)-aryl, —C(O)-heteroaryl, —SO$_2$—R$^7$, aryl, heteroaryl, —CONR$^4$R$^5$ or —C(O)—O—(C$_1$–C$_6$)alkyl;

R$^9$ is 1 to 3 substituents independently selected from the group consisting of hydrogen, C$_1$–C$_6$ alkyl, C$_1$–C$_6$ alkoxy, halogeno and —CF$_3$; and R$^{12}$ is hydrogen, C$_1$–C$_6$ alkyl, —C(O)—(C$_1$–C$_6$ alkyl), —SO$_2$—R$^7$, R$^9$-phenyl, —CONR$^4$R$^5$, —C(O)—O—(C$_1$–C$_6$)alkyl, —CHO, C$_3$–C$_7$ cycloalkyl, (C$_3$–C$_7$) cycloalkyl-(C$_1$–C$_6$)alkyl, benzyl, benzoyl, —C(O) (C$_3$–C$_7$)cycloalkyl, —C(O)(C$_1$–C$_6$)alkylphenyl, pyridylmethyl, —C(O)pyridyl, —C(O)N(di-(C$_1$–C$_6$)-alkyl) or 4-tetrahydropyranyl.

2. The compound of claim 1 wherein R$^8$ is C(O)—(C$_1$–C$_6$ alkyl), —C(O)—(C$_3$–C$_7$ cycloalkyl), —C(O)-aryl, —C(O)-heteroaryl, —SO$_2$—R$^7$, aryl, heteroaryl, or —CONR$^4$R$^5$.

3. The compound of claim 1 selected from the group consisting of

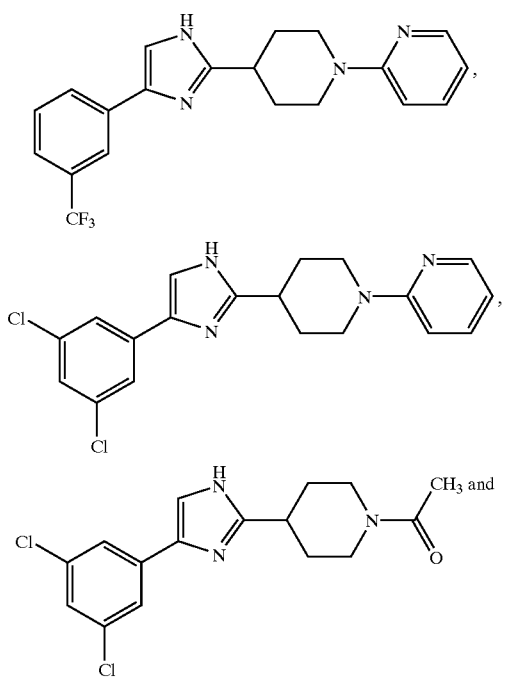

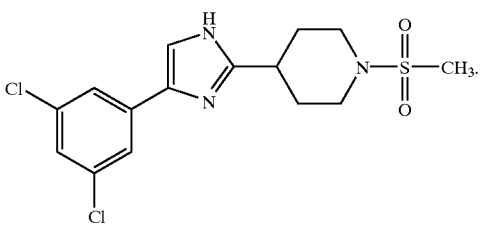

4. A pharmaceutical composition comprising a compound as defined in claim 1 in combination with a pharmaceutically acceptable carrier.

5. A method for treating an eating disorder or diabetes comprising administering to a mammal in need of such treatment an effective amount of a compound of claim 1.

6. A pharmaceutical composition comprising a compound as defined in claim 3 in combination with a pharmaceutically acceptable carrier.

7. A method for treating an eating disorder or diabetes comprising administering to a mammal in need of such treatment an effective amount of a compound of claim 3.

* * * * *